(12) United States Patent
Liu et al.

(10) Patent No.: US 11,180,733 B2
(45) Date of Patent: Nov. 23, 2021

(54) METHOD OF GENERATING MESENCHYMAL STEM CELLS AND USES THEREOF

(71) Applicant: AGENCY FOR SCIENCE, TECHNOLOGY AND RESEARCH, Singapore (SG)

(72) Inventors: Tong Ming Liu, Singapore (SG); Bing Lim, Singapore (SG); Pin Li, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 59 days.

(21) Appl. No.: 16/315,624

(22) PCT Filed: Jul. 4, 2017

(86) PCT No.: PCT/SG2017/050339
§ 371 (c)(1),
(2) Date: Jan. 4, 2019

(87) PCT Pub. No.: WO2018/009147
PCT Pub. Date: Jan. 11, 2018

(65) Prior Publication Data
US 2019/0322987 A1    Oct. 24, 2019

(30) Foreign Application Priority Data
Jul. 4, 2016    (SG) .......................... 10201605481T

(51) Int. Cl.
*C12N 5/0775* (2010.01)
*A61K 35/28* (2015.01)
*C12N 5/074* (2010.01)

(52) U.S. Cl.
CPC ............ *C12N 5/0663* (2013.01); *A61K 35/28* (2013.01); *C12N 5/0696* (2013.01); *C12N 2500/38* (2013.01); *C12N 2501/11* (2013.01); *C12N 2501/115* (2013.01); *C12N 2501/135* (2013.01); *C12N 2501/15* (2013.01); *C12N 2501/155* (2013.01); *C12N 2501/16* (2013.01); *C12N 2501/415* (2013.01); *C12N 2501/602* (2013.01); *C12N 2501/603* (2013.01); *C12N 2501/604* (2013.01); *C12N 2501/606* (2013.01); *C12N 2501/727* (2013.01); *C12N 2501/999* (2013.01); *C12N 2506/02* (2013.01); *C12N 2506/1307* (2013.01); *C12N 2506/45* (2013.01); *C12N 2533/52* (2013.01)

(58) Field of Classification Search
CPC .... A61K 35/28; C12N 5/0663; C12N 5/0696; C12N 5/0662; C12N 2501/11; C12N 2501/999; C12N 2501/603; C12N 2533/52; C12N 2501/16; C12N 2501/415; C12N 2506/02; C12N 2500/38; C12N 2506/1307; C12N 2501/606; C12N 2501/15; C12N 2501/115; C12N 2501/602; C12N 2501/155; C12N 2501/604; C12N 2501/135; C12N 2506/45; C12N 2501/727; A61P 19/04

See application file for complete search history.

(56) References Cited

U.S. PATENT DOCUMENTS

| 2005/0090002 | A1 | 4/2005 | Cancedda et al. | |
|---|---|---|---|---|
| 2010/0166713 | A1* | 7/2010 | Dalton | C12N 5/0603 424/93.7 |
| 2011/0086379 | A1 | 4/2011 | Blak et al. | |

FOREIGN PATENT DOCUMENTS

| WO | 2011116117 A2 | 9/2011 | |
|---|---|---|---|
| WO | WO-2011116117 A2 * | 9/2011 | ........... C12N 5/0692 |
| WO | 2012013969 A1 | 2/2012 | |

OTHER PUBLICATIONS

Gharibi et al. Effects of Medium Supplements on Proliferation, Differentiation Potential, and In Vitro Expansion of Mesenchymal Stem Cells. Stem Cells Translational Medicine (2012), 1,771-782. (Year: 2012).*
Carpenter et al. Properties of Four Human Embryonic Stem Cell Lines Maintained in a Feeder-Free Culture System. Developmental Dynamics (2004), 229, 243-258. (Year: 2004).*
Lai R.C., Choo A., Lim S.K. (2011) Derivation and Characterization of Human ESC-Derived Mesenchymal Stem Cells. In: Vemuri M ., Chase L., Rao M. (eds) Mesenchymal Stem Cell Assays and Applications. Chapter 11 in Methods in Molecular Biology (Methods and Protocols), vol. 698. Humana Press. (Year: 2011).*
Liu et al. One-Step Derivation of Mesenchymal Stem Cell (MSC)-Like Cells from Human Pluripotent Stem Cells on a Fibrillar Collagen Coating. PLoS One (2012), 7(3), e33225. (Year: 2012).*
Hatzopoulos et al. Isolation and characterization of endothelial progenitor cells from mouse embryos. Development (1998), 125, 1457-1468. (Year: 1998).*
Paulkin et al. Mouse pluripotent stem cells at a glance. Journal of Cell Science (2011), 124, 3727-3732. (Year: 2011).*
Fukata et al. Derivation of Mesenchymal Stromal Cells from Pluripotent Stem Cells through a Neural Crest Lineage using Small Molecule Compounds with Defined Media. PLoS One (2014), 9(12), e112291. (Year: 2014).*
Amaya, et al., "FGF signalling in the early specification of mesoderm in Xenopus," Development, 1993, pp. 477-487, vol. 118, The Company of Biologists Limited 1993.
Amaya, et al., "Expression of a Dominant Negative Mutant of the FGF Receptor Disrupts Mesoderm Formation in Xenopus Embryos," Cell, Jul. 26, 1991, pp. 257-270, vol. 66, Cell Press.

(Continued)

*Primary Examiner* — Sean C. Barron
(74) *Attorney, Agent, or Firm* — Womble Bond Dickinson (US) LLP

(57) ABSTRACT

The present disclosure provides a method of generating mature mesenchymal stem cells and the cell culture medium used in such method. Also disclosed herein include a mesenchymal stem cell culture obtained by the method as disclosed herein, and uses thereof.

9 Claims, 34 Drawing Sheets

(56) References Cited

OTHER PUBLICATIONS

Amsalem, et al., "Iron-Oxide Labeling and Outcome of Transplanted Mesenchymal Stem Cells in the Infarcted Myocardium," Circulation, 2007, pp. 138-145, vol. 1161, American Heart Association, Inc.
Arnold, et al., "Brachyury is a target gene of the Wnt/β-catenin signaling pathway," Mechanisms of Development, 2000, pp. 249-258, vol. 91, Elsevier.
Barberi, et al., "Derivation of Multipotent Mesenchymal Precursors from Human Embryonic Stem Cells," PLoS Medicine, Jun. 2005, 7 pgs., vol. 2, No. 6, PLoS Medicine.
Bilousova, et al., "Osteoblasts derived from Induced Pluripotent Stem Cells form Calcified Structures in Scaffolds both in vitro and in vivo," Stem Cells, Feb. 2011, pp. 206-216, vol. 29, No. 2, National Institutes of Health.
Buckley, et al. "Expansion in the presence of FGF-2 enhances the functional development of cartilaginous tissues engineered using infrapatellar fat pad derived MSCs," Journal of the Mechanical Behavior of Biomedical Materials II, 2012, pp. 102-111, Elsevier, Ltd.
Chase, et al., "A novel serum-free medium for the expansion of human mesenchymal stern cells," Stem Cell Research & Therapy, 2010, vol. 1, No. 8, BioMed Central.
Chen, et al., "Stepwise Differentiation of Human Embryonic Stem Cells Promotes Tendon Regeneration by Secreting Fetal Tendon Matrix and Differentiation Factors," Stem Cells, 2009, pp. 1276-1287, vol. 27, Stem Cells.
Ciruna, et al., "FGF Signaling Regulates Mesoderm Cell Fate Specification and Morphogenetic Movement at the Primitive Streak," Developmental Cell, Jul. 2001, pp. 37-49, vol. 1, Cell Press.
De Peppo, et al., "Engineering bone tissue from human induced pluripotent stem cells," PNAS, May 21, 2013, pp. 8680-8685, vol. 110, No, 21, PNAS.
Dravid, et al., "Defining the Role of Wnt/β-Catenin Signaling in the Survival, Proliferation, and Self-Renewal of Human Embryonic Stern Cells," Stem Cells, 2005, pp. 1489-1501, vol. 23, Stem Cells.
Dunty, et al., "Transcriptional Profiling of Wnt3a Mutants Identifies Sp Transcription Factors as Essential Effectors of the Wnt/β-catenin Pathway in Neuromesodermal Stem Cells," PLoS One, Jan. 2014, 9 pages, vol. 9, No. 1, PLoS One.
Evseenko, et al., "Mapping the first stages of mesoderm commitment during differentiation of human embryonic stem cells," PNAS, Aug. 3, 2010, pp. 13742-13747, vol. 107, No. 31, PNAS.
Gadue, et al., "Wnt and TGF-β signaling are required for the induction of an in vitro model of primitive streak formation using embryonic stem cells," PNAS, Nov. 7, 2006, pp. 16806-16811, vol. 103, No. 45, PNAS.
Hall, et al., "All for one and one for all: condensations and the initiation of skeletal development," BioEssays, 2000, pp. 138-147, vol. 22, John Wiley & Sons, Inc.
Handorf, et al., "Fibroblast Growth Factor-2 Primes Human Mesenchymal Stem Cells for Enhanced Chondrogenesis," 2011, 11 pgs., vol. 6, No. 7, PLoS One.
Harrison, et al., "Sp5, a New Member of the Sp1 Family, Is Dynamically Expressed during Development and Genetically Interacts with Brachyury," Developmental Biology, 2000, pp. 358-372, vol. 227, Academic Press.
Hwang, et al., "In vivo commitment and functional tissue regeneration using human embryonic stern cell-derived mesenchymal cells," PNAS, Dec. 30, 2008, pp. 20641-20646, vol. 105, No. 52, PNAS.
Hynes, et al., "Generation of Functional Mesenchymal Stem Cells from Different Induced Pluripotent Stem Cell Lines," Stem Cells and Development, 2014, pp. 1084-1096, vol. 23, No. 10, Mary Ann Liebert, Inc.
Huelsken, et al., "Requirement for β-Catenin in Anterior-Posterior Axis Formation in Mice," The Journal of Cell Biology, Feb. 7, 2000, pp. 567-578, vol. 148, No. 3, Rockefeller University Press.
Johnstone, et al., "In Vitro Chondrogenesis of Bone Marrow-Derived Mesenchymal Progenitor Cells," Experimental Cell Research, 1998, pp. 265-272, vol. 238, Academic Press.
Kelly, et al., "The Wnt co-receptors Lrp5 and Lrp6 are essential for gastrulation in mice," Development, Feb. 2004, pp. 2803-2815, vol. 131, The Company of Biologists.
Kingham, et al., "Distinct roles for isoforms of the catalytic subunit of class-IA PI3K in the regulation of behaviour of murine embryonic stem cells," Journal of Cell Science, Apr. 3, 2009, pp. 2311-2321, vol. 122, No. 13, The Company of Biologists 2009.
Ko, et al., "Osteogenesis from Human Induced Pluripotent Stem Cells: An In Vitro and In Vivo Comparision with Mesenchymal Stem Cells," Stem Cells and Development, 2014, 10 pgs., vol. 23, No. 15, Mary Ann Liebert, Inc.
Koyama, et al., "Human Induced Pluripotent Stern Cells Differentiated into Chondrogenic Lineage Via Generation of Mesenchymal Progenitor Cells," Stem Cells and Development, 2013, 12 pgs., vol. 22, No. 1, Mary Ann Liebert, Inc.
Lai, et al., "Fgf2 Inhibits Differentiation of Mesenchymal Stem Cells by Inducing Twist2 and Spry4, Blocking Extracellular Regulated Kinase Activation and Altering Fgfr Expression Levels," Stem Cells, Jul. 2011, pp. 1102-1111, vol. 29, No. 7, National Institutes of Health.
Laurila, et al., "Human embryonic stem cell derived mesenchymal stromal cell transplantation in rat hind limb injury model," Cytotherapy, 2009, 17 pgs., vol. 11, No. 6, National Institutes of Health.
Liu, et al., "Requirement for Wnt3 in vertebrate axis formation," Nature Genetics, Aug. 1999, pp. 361-365, vol. 22, 1999 Nature America Inc.
Liu, et al., "Identification of Common Pathways Mediating Differentiation of Bone Marrow- and Adipose Tissue-Derived Mesenchymal Stem Cells into Three Mesenchymal Lineages," Stem Cell Genetics and Genomics, 2007, pp. 750-760, vol. 25.
Liu, et al., "Zinc-Finger Protein 145, Acting as an Upstream Regulator of SOX9, Improves the Differentiation Potential of Human Mesenchymal Stem Cells for Cartilage Regeneration and Repair," Arthritis & Rheumatism, Sep. 2011, pp. 2711-2720, vol. 63, No. 9, American College of Rheumatology.
Lian, et al., "Functional Mesenchymal Stem Cells Derived From Human Induced Pluripotent Stem Cells Attenuate Limb Ischemia in Mice," Circulation, 2010, pp. 1113-1123, vol. 121, American Heart Association, Inc.
Lindsley, et al., "Canonical Wnt signaling is requirement for development of embryonic stem cell-derived mesoderm," Development, Jul. 26, 2006, pp. 3787-3896, vol. 133.
Martin, et al., "Brachyury establishes the embryonic mesodermal progenitor niche," Genes & Development, 2010, pp. 2778-2783, vol. 24, Cold Spring Harbor Laboratory Press.
Mathieu, et al., "Nodal and Fgf pathways interact through a positive regulatory loop and synergize to maintain mesodermal cell populations," Development 2004, pp. 629-641, vol. 131, The Company of Biologists.
McLean, et al., "Activin A Efficiently Specifies Definitive Endoderm from Human Embryonic Stem Cells Only When Phosphatidylinositol 3-Kinase Signaling Is Suppressed," Embryonic Stem Cells: Characterization Series, 2007, pp. 29-38, vol. 25, Stem Cells.
Moon, et al., WNT/β-Catenin Signaling in Alzheimer's Disease, CNS & Neurological Disorders—Drug Targets, 2014, 11 pgs., vol. 13, Bentham Science Publishers.
Nakanishi, et al., "Directed induction of anterior and posterior primitive streak by Wnt from embryonic stem cells cultured in a chemically defined serum-free medium." FASEB Journal, Jan. 2009, pp. 114-122, vol. 23, Research Gate.
Nakayama, et al., "From Pluripotent Stem Cells to Lineage-Specific Chondrocytes: Essential Signalling and Cellular Intermediates," Embryonic Stem Cells: The Hormonal Regulation of Pluripotency and Embryogenesis, Apr. 2011, 30 pgs., The Authors.
Ng, et al., "PDGF, TGF-β, and FGF signaling is important for differentiation and growth of mesenchymal stem cells (MSCs): transcriptional profiling can identify markers and signaling pathways important in differentiation of MSCs into adipogenic, chondrogenic, and osteogenic lineages," Blood: Hematopoiesis and

(56) References Cited

OTHER PUBLICATIONS

Stem Cells, Jul. 7-15, 2008, pp. 295-307, vol. 112, No. 2, The American Society of Hematology.

Nostro, et al., "Wnt, Activin, and BMP Signaling Regulate Distinct Stages in the Developmental Pathway from Embryonic Stem Cells to Blood," Cell Stem Cell., Jan. 10, 2008, pp. 60-71, vol. 2, No. 1, National Institutes of Health.

Olivier, et al., "Differentiation of Human Embryonic Stem Cells into Bipotent Mesenchymal Stem Cells," Embryonic Stem Cells, 2006, pp. 1914-1922, vol. 24, Stem Cells.

Paling, et al., "Regulation of Embryonic Stem Cell Self-renewal by Phosphoinositide 3-Kinase-dependent Signaling," The Journal of Biological Chemistry, Nov. 12, 2004, pp. 48063-48070, vol. 279, No. 46, The American Society for Biochemistry and Molecular Biology, Inc.

Ramkumar, et al., "Snapshot: Mouse Primitive Streak," Cell, Aug. 5, 2011, 3 pgs., vol. 146, Elsevier Inc.

Sakurai, et al., "In Vitro Modeling of Paraxial Mesodermal Progenitors Derived from Induced Pluripotent Stem Cells," PLoS ONE, Oct. 2012, 14 pgs., vol. 7, No. 10, PLoS One.

Schulte-Merker, et al., "Mesoderm formation in response to Brachyury requires FGF signalling," Current Biology, 1995, pp. 62-67, No. 5, National Institute for Medical Research.

Slack, et al., "Mesoderm induction in early Xenopus embryos by heparin-binding growth factors," Nature, Mar. 1987, 4 pgs., vol. 326, Nature Publishing Group.

Smith, et al., "Expression of a Xenopus Homolog of Brachyury (T) Is an Immediate-Early Response to Mesoderm Induction," Cell, Oct. 4, 1991, pp. 79-87, vol. 67, Cell Press.

Sumi, et al., "Defining early lineage specification of human embryonic stem cells by the orchestrated balance of canonical Wnt/β-catenin, Activin/Nodal and BMP signaling," Development and Disease, 2008, pp. 2969-2979, vol. 135.

Takahashi, et al., "Induction of Pluripotent Stem Cells from Adult Human Fibroblasts by Defined Factors," Cell, Nov. 30, 2007, pp. 861-872, vol. 131, Elsevier Inc.

Chiang, et al., "Allogeneic Mesenchymal Stem Cells in Combination with Hyaluronic Acid for the Treatment of Osteoarthritis in Rabbits," PLoS One, Feb. 25, 2016,15 pgs., vol. 11, No. 2, PLoS ONE.

Villa-Diaz, et al., "Derivation of functional mesenchymal stem cells from human induced pluripotent stem cells cultured on synthetic polymer substrates," Stem Cells, Jun. 2012, pp. 1174-1181, vol. 30, No. 6, National Institutes of Health.

Gharibi, et al., "Effects of Medium Supplements on Proliferation, Differentiation Potential, and In Vitro Expansion of Mesenchymal Stem Cells," Stem Cells Translational Medicine, 2012, pp. 771-782, vol. 1, AlphaMed Press.

The International Preliminary Report on Patentability for PCT Application No. PCT/SG2017/050339 dated Jan. 8, 2019, 9 pages.

The International Search Report and Written Opinion of the International Searching Authority for PCT/SG2017/050339 dated Sep. 19, 2017, 15 pages.

Lian, et al., "Derivation of Clinically Compliant MSCs from CD105+, CD24-31 Differentiated Human ESCs," Stem Cells: Embryonic Stem Cells, 2007, pp. 425-436, vol. 25, Stem Cells.

Oldershaw, et al., "A chemically-defined protocol for generating chondrocytes from human embryonic stem cells,".

Oldershaw, et al., "Directed differentiation of human embryonic stem cells toward chondrocytes," Nature Biotechnology, Nov. 2010, 10 pgs., vol. 28, No. 11, Nature America, Inc.

Rodrigues, et al., "Growth factor regulation of proliferation and survival of multipotential stromal cells," Stem Cell Research & Therapy, 2010, 13 pgs., vol. 1, No. 32, BioMed Central Ltd.

Tam, et al., "Gene function in mouse embryogenesis: get set for gastrulation," Nature Reviews: Genetics, May 2007,14 pgs., vol. 8, Nature Publishing Group.

Tamama, et al., "Epidermal Growth Factor (EGF) Treatment on Multipotential Stromal Cells (MSCs). Possible Enhancement of Therapeutic Potential of MSC," Journal of Biomedicine and Biotechnology, 2010, 11 pgs., Hindawi Publishing Corporation.

Tran, et al., "Efficient Differentiation of Human Pluripotent Stem Cells into Mesenchymal Stem Cells by Modulating Intracelludar Signaling Pathways in a Feeder/Serum-Free System," Stem Cells and Development, 2012, pp. 1165-1175, vol. 21, No. 7, Mary Ann Liebert, Inc.

Trivedi, et al., "Derivation and immunological characterization of mesenchymal stromal cells from human embryonic stem cells," Experimental Hematology, 2008, pp. 350-359, vol. 36, Elsevier.

Tsutsumi, et al., "Retention of Multilineage Differentiation Potential of Mesenchymal Cells during Proliferation in Response to FGF," Biochemical and Biophysical Research Communications, Sep. 14, 2001, pp. 413-419, vol. 288, Academic Press.

Umeda, et al., "Human chondrogenic paraxial mesoderm, directed specification and prospective isolation from pluripotent stem cells," Scientific Reports, 2012, 11 pgs., vol. 2, No. 455, Nature.

Vallier, et al., "Early Cell Fate Decisions of Human Embryonic Stem Cells and Mouse Epiblast Cells Are Controlled by the Same Signalling Pathways," PLoS One, 2009, 13 pgs., vol. 4, No, 6, PLoS One.

Choi, Kyung-Min et al. "Effect of ascorbic acid on bone marrow-derived mesenchymal stem cell proliferation and differentiation," JLBSBE, vol. 105 No. 6, Feb. 27, 2008, 586-594.

Vodyanik, Maxim A. et al., " a mesoderm-derived precursor for mesenchymal stem and endothelial cells," Cell Stem Cell, 7(6), Dec. 3, 2010, 718-729.

Waese, Elaine Y.L., "One-step generation of murine embryonic stem cell-derived mesoderm progenitors and chondrocytes in a serum-free monolayer differentiation system," Stem Cell Research, 2011, 34-49.

Winnier, Glenn, "Bone morphogenetic protein-4 is required for mesoderm formation and patterning in the mouse," Genes & Developement 9, Cold Spring Harbor Press, Jul. 12, 1995, 2105-2116.

Yang, Lei et al., "Human Cardiovascular progenitor cells develop from a KDR+ embryonic-stem-cell-derived population," Nature, Letters, vol. 453, May 22, 2018, 524-529.

\* cited by examiner

D

C

BJ-iPSCs

A

E

F

G

H

A  B

C

D

Gut-like epithelium

Cartilage

Neural tissue

Epithelium

Adipose tissue

Muscle

METHOD OF GENERATING MESENCHYMAL STEM CELLS AND USES THEREOF

CROSS-REFERENCE TO RELATED APPLICATIONS

This patent application is a U.S. National Phase Application Under 35 U.S.C. § 371 of International Application No. PCT/SG2017/050339, filed on 4 Jul. 2017, entitled METHOD OF GENERATING MESENCHYMAL STEM CELLS AND USES THEREOF, which claims the benefit of priority of Singapore patent application No. 10201605481T, filed 4 Jul. 2016, the contents of which were incorporated by reference in the entirety for all purposes.

FIELD OF THE INVENTION

The present invention relates to cell biology and biochemistry, in particular methods of deriving and maintaining stem cells, in particular mature mesenchymal stem cells.

BACKGROUND OF THE INVENTION

Articular cartilage is the tough but flexible connective tissue that covers the ends of bones to provide lubrication and shock absorption to joints. It is susceptible to damages due to wear, tear, trauma and degenerative conditions. Injured or damaged cartilage can cause symptoms such as joint pain, inflammation, stiffness and even loss of joint function. Due to its avascular nature, articular cartilage has a poor intrinsic capacity for healing. Thus, severe cartilage diseases are often treated by surgical methods, such as the transplantation of autologous articular chondrocytes, which are the articular chondrocytes obtained from the patient himself. Transplantation of articular chondrocytes requires the in vitro expansion of articular chondrocytes prior to transplantation. However, articular chondrocytes tend to de-differentiate into fibroblasts during such in vitro expansion. In addition, limited amount of cells can be obtained from the patient himself, due to limited areas of non-disease-affected cartilage. Mesenchymal stem cells (MSCs) isolated from adult tissues such as bone marrow or adult adipose tissues have also been used for cartilage repair, due to their osteochondral potential, immunomodulatory and engraftment-promoting properties. However, limited life span and loss of differentiation potential during in vitro expansion of MSCs obtained from adult tissues greatly hamper their clinical application. Aging and aging-related disorders also affect the survival and differentiation ability of MSCs isolated from adult tissues. Although there have been reports of methods of deriving MSCs from embryonic stem cells or induced pluripotent stem cells (iPSCs), such methods generally use matrigel, fetal bovine serum (FBS) and/or feeder cells with non-defined components for the derivation of MSCs, which greatly compromise the clinical application of the MSCs derived. Current methods of the differentiation of iPSCs into MSCs are also time-consuming and inefficient. Thus, there is the need for an alternative method of deriving MSCs.

SUMMARY OF THE INVENTION

In a first aspect, there is provided a method of generating mature mesenchymal stem cells from lateral plate mesoderm cells, comprising culturing the lateral plate mesoderm cells on an extracellular matrix in a mesenchymal stem cell culture medium comprising: (i) fibroblast growth factor; (ii) platelet-derived growth factor (PDGF); (iii) epidermal growth factor (EGF) family protein; and (iv) ascorbic acid.

In a second aspect, there is provided a mesenchymal stem cell culture obtained by the method of the present invention.

In a third aspect, there is provided a method of treating cartilage or bone disease or injury in a patient, comprising transplanting a composition of cells comprising mature mesenchymal stem cells into the patient with cartilage defects, wherein the composition is obtained by the method of the present invention.

In a fourth aspect, there is provided a culture medium for deriving primitive streak mesendoderm cells from pluripotent stem cells, comprising: (a) activin; (b) WNT-signaling activator; and (c) fibroblast growth factor.

In a fifth aspect, there is provided a culture medium for deriving lateral plate mesoderm cells from primitive streak mesendoderm cells, comprising: (1) fibroblast growth factor; (2) bone morphogenetic protein; (3) follistatin; and (4) optionally Rho-associated protein kinase (ROCK) inhibitor.

In a sixth aspect, there is provided a culture medium for deriving and maintaining mature mesenchymal stem cells from lateral plate mesoderm cells, comprising: (i) fibroblast growth factor; (ii) platelet-derived growth factor (PDGF); (iii) epidermal growth factor (EGF) family protein; and (iv) ascorbic acid.

BRIEF DESCRIPTION OF THE DRAWINGS

The invention will be better understood with reference to the detailed description when considered in conjunction with the non-limiting examples and the accompanying drawings, in which:

FIG. 9A shows effects of activin concentration (25-100 ng/ml) on the formation of primitive streak-like mesendoderm cells. BJC1-iPSCs were differentiated towards primitive streak-like mesendoderm cells for 2 days with indicated combination of CHIR99021 (3 μM) and FGF (20 ng/ml) in conjunction with the indicated signaling perturbations, qPCR was performed at day 2. FIG. 9B shows the optimization of activin A for differentiation of iPSCs toward primitive streak-like mesendoderm cells based on the expression of PS genes to endodermal gene Sox17. FIG. 9C represents data from FACS analysis showing more than 97% cells at day 2 were positive for primitive streak genes MIXL1, Brachyury (T) and GSC. FIG. 9D represents the immunofluoresence results at day 2 showing the expression of MIXL1, Brachyury (T) and GSC after 2 day of primitive streak induction. FIG. 9E shows ChIP-seq data indicating that Brachyury (T) and Wnt3 were active in cells at day 2.

FIG. 10A shows effects of BMP4 concentration and antagonism of BMP signaling noggin on mesodermal differentiation. BJC1-iPSCs were differentiated towards mesoderm after 8 days of differentiation with indicated combination of FGF (20 ng/ml), Rock inhibitor Y27632 (5 uM) and Follistatin (100 ng/ml) in conjunction with the indicated signaling perturbations, qPCR was performed at day 10. FIG. 10B shows effects of follistatin on mesodermal differentiation. BJC1-iPSCs were differentiated towards mesoderm after 8 days of differentiation with indicated combination of FGF (20 ng/ml), BMP4 (40 ng/ml), and Rock inhibitor Y27632 (5 uM) in conjunction with the indicated signaling perturbations, qPCR was performed at day 10. The results indicate that as compared to the absence of Follistatin, the presence of Follistatin significantly increases the expression of lateral plate mesoderm genes such as Hand1 and FOXF1, as well as mesenchymal stem cell gene CD44 and CD105. FIG. 10C shows the comparison of the effects of ROCK inhibitor Y27632 and neurotrophin-4 (NT4) on the induction of mesoderm. The results indicate that as compared to NT4, ROCK inhibitor Y27632 significantly increases the expression of lateral plate mesoderm genes such as Hand1 and FOXF1. FIG. 10D shows the results obtained from ChIP-seq indicating that Hand1 was active in cells at day 2 of differentiation.

FIG. 11A shows the morphology of cells under different combination of cytokines. FIG. 11B shows the expression of CD73 and CD44 under different combination of FGF, PDGF, TGFβ1, EGF and vitamin C by qPCR. FIG. 11C shows FACS data showing CD73 expression during differentiation. FIG. 11D shows CD44 and EBF1 loci at day 10.

FIG. 12A shows that the cells obtained from differentiation displayed fibroblast morphology of mature mesenchymal stem cells. FIG. 12B shows the correlation coefficient between iPSC-MSC and bone marrow derived MSCs (BMSCs). FIG. 12C shows clustering of gene expression data which demonstrates that the gene expression profile of the iPSC-MSC obtained at day 21 more closely represents the gene expression profiles of the BMSC control, as compared to the differentiating stem cells at day 0, day 2, day 8, day 10 and day 14. FIG. 12D shows the surface antigen profile of iPSC-MSCs. FIG. 12E shows the results of immunostaining of iPSC-MSCs for CD73 and CD105. FIG. 12F shows that the iPSC-MSCs have the normal karyotype of mature mesenchymal stem cells. FIG. 12G shows that the iPSC-MSCs expressed adipogenic, osteogenic and chondrogenic genes when being induced to differentiate towards these three different lineages (*P<0.05). FIG. 12H shows that the iPSC-MSCs have differentiation potential towards three different lineage: adipogenic, osteogenic and chondrogenic lineages, as demonstrated by lineage specific stain. iPSC-MSCs show positive oil red stain for oil droplet in adipogenesis; alizarin red stain for calcium deposits and AP stain for alkaline phosphatase activity in osteogenesis; alcian blue stain for sulphate proteoglycans and type II collagen immunostaining for major collagen in cartilage. The results demonstrate that the iPSC-MSCs obtained using the methods as disclosed herein are able to differentiate into fat, bone and cartilage.

FIG. 13A shows the gene expression profiles of the cells as the iPSCs differentiate towards mature mesenchymal stem cells (MSCs). FIG. 13B shows the analysis of genes expressed during EMT. FIG. 13C shows the analysis of genes expressed in MSCs. The results show the following correlation of gene expressions: IPSC-MSC vs EMT phases [iPSC-MSC/(D8, D10 & D14)]: Ap-1, GATA, IRF, STAT, ETS, FOXD1; EMT vs (iPSC & PS) [D8/(DO & D2)]: IRF, GLI, SMAD3, AP2-alpha, FoxJ2, MEIS1. FIG. 13D shows change of EMT-related genes during differentiation of iPSCs towards MSCs. FIG. 13E shows expression of pro-inflammatory genes in MSCs.

FIG. 14A shows enrichment of functional annotation of proximal genes. FIG. 14B shows results of GREAT analysis of genes related to differentiation. FIG. 14C shows expression of promoters proximal to regions in different classes. FIG. 14D shows the top four motifs enriched in each different class and their p-values.

FIG. 15A shows that iPSC-MSCs partially repaired cartilage defects at week 6 after transplant. iPSC-MSCs were pre-induced into cartilage differentiation under pellet culture for 1 week in vitro and then transplanted into the rats with cartilage defects. After 6 weeks of transplant, iPSC-MSCs partially repaired cartilage defects, similar to BMSCs by the HE stain, alcian blue stain for sulphate proteoglycans, and type II collagen immunostain for major collagen in cartilage. No hyaline cartilage was observed in the control group (empty) without any transplanted mesenchymal stem cells. FIG. 15B shows histological grading score which demonstrates that there was significant difference between iPSC-MSCs and the control group, as well as BMSCs and the control group, while there was no significant difference between iPSC-MSCs and BMSCs. FIG. 15C represents immunostaining results showing that human specific Lamin A/C positive cells were detected in iPSC-MSC and BMSC group, but not in host cartilage at week 6. FIG. 15D shows that the iPS-MSCs fully repaired cartilage defects at week 12 after transplant. iPSC-MSCs were pre-induced into cartilage differentiation under pellet culture for 1 week in vitro and then transplanted into the rats with cartilage defects. After 12 weeks of transplant, iPSC-MSCs and BMSCs almost fully repaired cartilage defects, as shown by the HE stain, alcian blue stain for sulphate proteoglycans, and type II collagen immunostain for major collagen in cartilage. No hyaline cartilage was observed in the control group (empty) without any transplanted mesenchymal stem cells. FIG. 15E shows histological grading score which demonstrates that there was significant difference between iPSC-MSCs and the control group, as well as BMSCs and the control group, while there was no significant difference between iPSC-MSCs and BMSCs. FIG. 15F represents immunostaining results showing that human specific Lamin A/C positive cells were detected in iPSC-MSC and BMSC group, but not in host cartilage at week 12.

FIG. 16A shows that the iPSC colonies displayed typical ES-like morphology on the feeder culture. FIG. 16B shows that the iPSC colonies displayed typical ES-like morphology on the feeder-free culture. FIG. 16C shows that similar to hES cells, the colonies of iPSCs were AP positive, which were different from fibroblasts negative for AP stain. FIG. 16D shows that the generated iPSCs formed teratomas containing all three germ layers of tissues after subcutaneous injection into nude mice, including gut-like epithelial tissues (endoderm), cartilage (mesoderm), adipose tissue (mesoderm) and neural tissue (ectoderm).

FIG. 17 shows that CHIR99021 enhances differentiation of induced pluripotent stem cells to primitive streak/mosendoerm compared with wnt3a. FIG. 17A shows that CHIR99021 promoted the adherence of iPSCs to the dish compared with wnt3a (ACF vs AWF). FIG. 17B shows CHIR99021 promoted differentiation toward PS-like mesendoderm compared with wnt3a.

DETAILED DESCRIPTION OF THE PRESENT INVENTION

Figure 1:
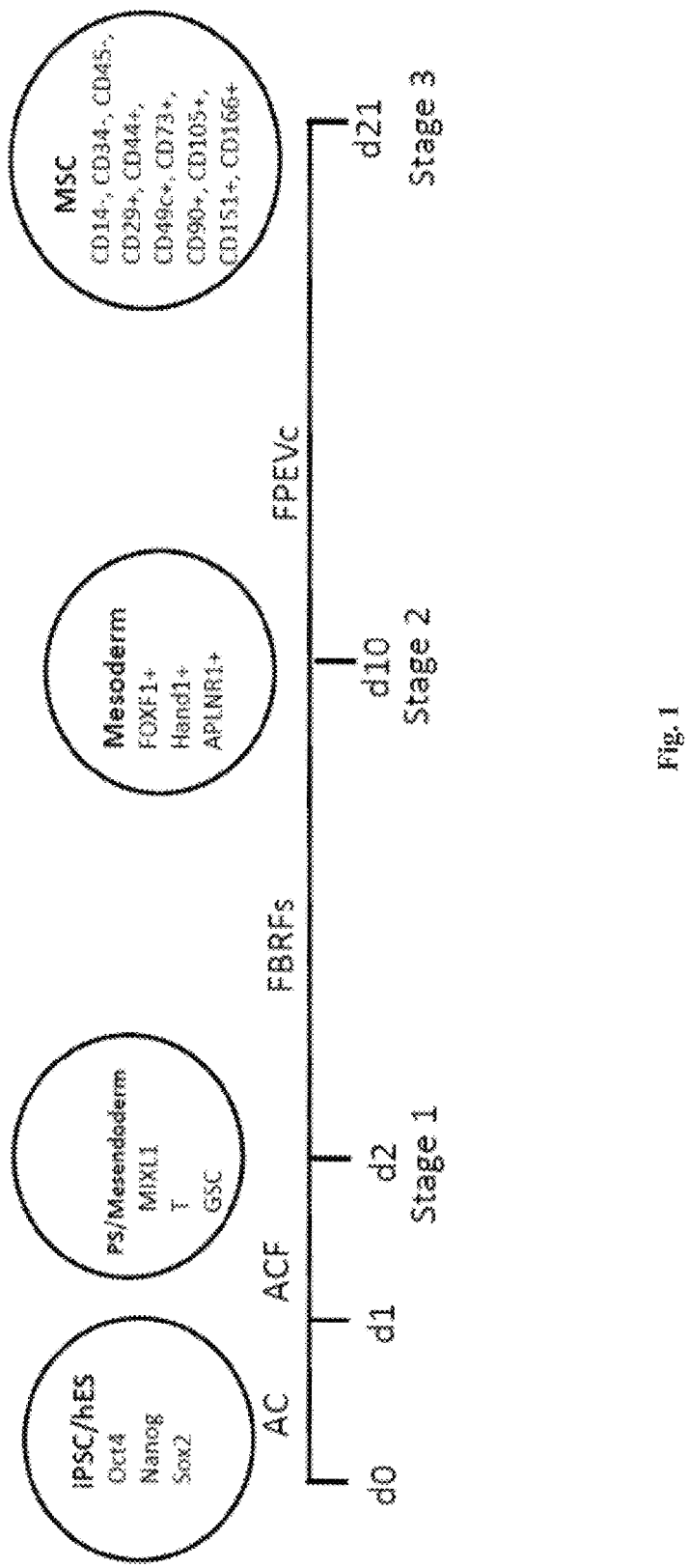
FIG. 1 outlines the method of generating mature mesenchymal stem cells as disclosed herein. Stage 1 represents the process of generating primitive streak or primitive streak-like mesendoderm cells from embryonic stem cells or induced pluripotent stem cells. Stage 2 represents the process of generating lateral plate or lateral plate-like mesoderm cells from primitive streak or primitive streak-like mesendoderm cells. Stage 3 represents the process of generating mature mesenchymal stem cells from lateral plate or lateral plate-like mesoderm cells.
Figure 2:
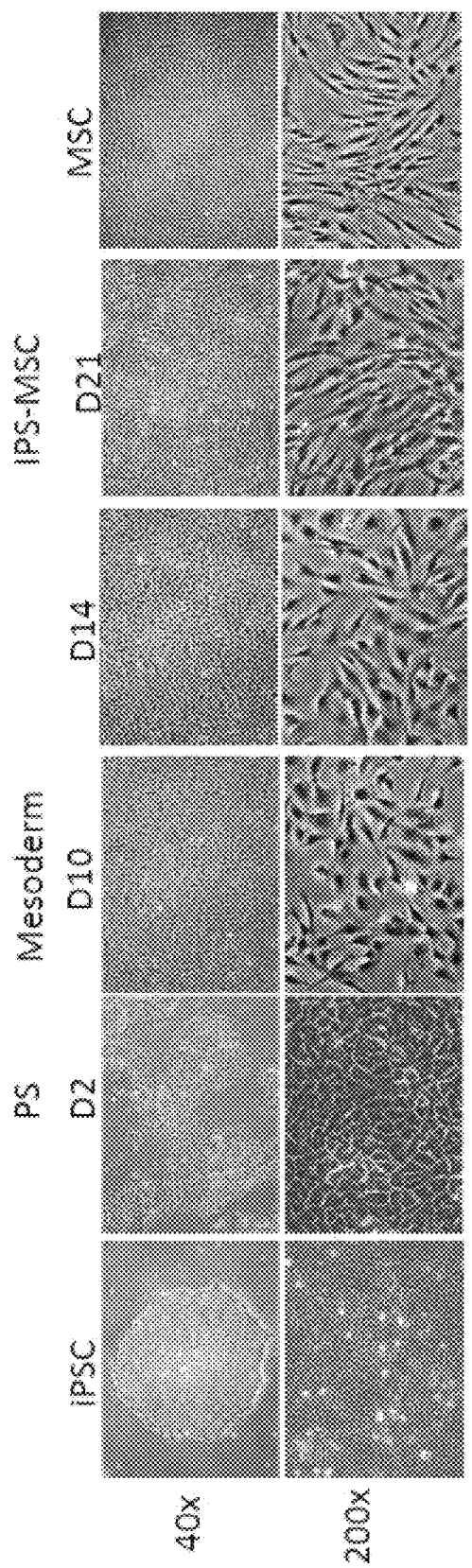
FIG. 2 shows morphological changes during differentiation from induced pluripotent stem cells to mesenchymal stem cells undergoing primitive streak/mesendoderm and mesoderm.
Figure 3:
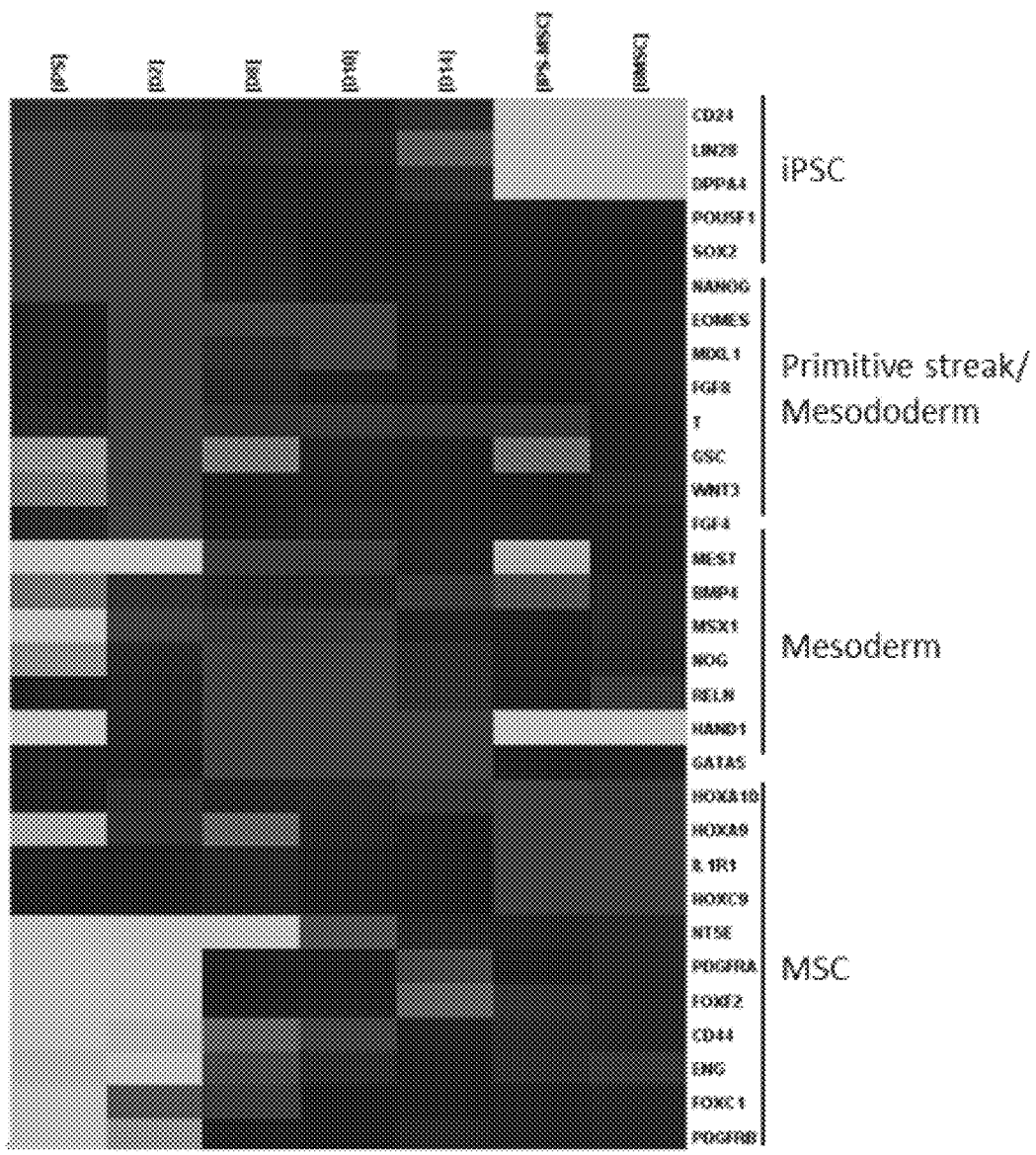
FIG. 3 shows heatmap based on microarray, demonstrating step-wise changes in gene expression during differentiation from induced pluripotent stem cells to mesenchymal stem cells (MSCs) undergoing primitive streak/mesendoderm and mesoderm.

The current differentiation protocols of human embryonic stem cells (hESCs) or induced pluripotent stem cells (iPSCs) towards mesenchymal stem cells (MSCs) involve the use of non-defined matrigel, FBS and feeder cells. Such methods greatly compromise the clinical application of the MSCs obtained, as the MSC cultures yielded using these currently available methods are typically heterogeneous cultures containing undesired cells.

The inventors of the present disclosure have set out to provide alternative method of generating MSCs, which could be used to produce clinically-compliant MSCs.

In a first aspect, there is provided a method of generating mature mesenchymal stem cells from lateral plate mesoderm cells or lateral plate-like mesoderm cells, comprising culturing the lateral plate mesoderm cells or lateral plate-like mesoderm cells on an extracellular matrix in a mesenchymal stem cell culture medium comprising: (i) fibroblast growth factor; (ii) platelet-derived growth factor (PDGF); (iii) epidermal growth factor (EGF) family protein; and (iv) ascorbic acid. For example, referring to FIG. 1, this method is directed to the culturing of the mesoderm cells from day 10 onwards.

The term "mesenchymal stem cells" as used herein refers to the multipotent stromal cells (i.e. connective tissue cells) that can differentiate into a variety of cell types, including, for example, osteoblasts (bone cells), chondrocytes (cartilage cells), myocytes (muscle cells) and adipocytes (fat cells). Mesenchymal stem cells are characterized morphologically by a small cell body which contains a large, round nucleus with a prominent nucleolus, which is surrounded by finely dispersed chromatin particles, giving the nucleus a clear appearance. The remainder of the cell body contains a small amount of Golgi apparatus, rough endoplasmic reticulum, mitochondria and polyribosomes. The shape of the mesenchymal stem cells is generally long and thin.

The mesenchymal stem cells obtained using the method of the first aspect are mature mesenchymal stem cells, which are able to differentiate into all three mesenchymal cell lines: osteoblasts, chondrocytes and adipocytes, under the appropriate differentiation conditions. Mature mesenchymal stem cells can be characterized by the expression of any one or more, or all of the following panel of markers: CD29, CD44, CD49c, CD73, CD90, CD105, CD151 and CD166. In one specific example, the mature mesenchymal stem cells are characterized by the expression of CD73. In another specific example, the mature mesenchymal stem cells are characterized by the expression of CD105.

The term "CD29" (with CD being the abbreviation of "cluster of differentiation"), also known as integrin beta-1, is the protein that in humans is encoded by the ITGB1 gene. Integrins are heterodimeric integral membrane proteins composed of an alpha chain and a beta chain. Integrin family members are membrane receptors involved in cell adhesion and recognition in a variety of processes including embryogenesis, hemostasis, tissue repair, immune response and metastatic diffusion of tumor cells.

The term "CD44" as used herein refers to a cell-surface glycoprotein involved in cell-cell interactions, cell adhesion and migration. It is a receptor for hyaluronic acid (HA) and can also interact with other ligands, such as osteopontin, collagens, and matrix metalloproteinases (MMPs). This protein participates in a wide variety of cellular functions including lymphocyte activation, recirculation and homing, hematopoiesis, and tumor metastasis.

The term "CD49c", also known as integrin alpha-3, is the protein that in humans is encoded by the ITGA3 gene. ITGA3 is an integrin alpha subunit. Together with beta-1 (i.e. CD29) subunit, it makes up half of the α3β1 integrin duplex that plays a role in neural migration and corticogenesis, acted upon by such factors as netrin-1 and reelin.

The term "CD73" as used herein refers to the protein encoded by the NT5E gene. It is a plasma membrane protein that catalyzes the conversion of extracellular nucleotides to membrane-permeable nucleosides.

The term "CD90" as used herein refers to the protein encoded by the THY1 gene. It is a cell surface glycoprotein and member of the immunoglobulin superfamily of proteins. It is involved in cell adhesion and cell communication in numerous cell types, but particularly in cells of the immune and nervous systems.

The term "CD105" as used herein refers to the protein encoded by the ENG gene. It is a homodimeric transmembrane protein which is a major glycoprotein of the vascular endothelium. This protein is a component of the transforming growth factor beta receptor complex.

The term "CD151" as used herein refers to the protein encoded by the CD151 gene. It is a member of the transmembrane 4 superfamily, also known as the tetraspanin family. Most of these members are cell-surface proteins that are characterized by the presence of four hydrophobic domains. The proteins mediate signal transduction events that play a role in the regulation of cell development, activation, growth and motility. CD151 is a cell surface glycoprotein that is known to complex with integrins and other transmembrane 4 superfamily proteins. It is involved in cellular processes including cell adhesion and may regulate integrin trafficking and/or function.

The term "CD166", also known as "activated leukocyte cell adhesion molecule", is the protein encoded by the ALCAM gene. It is a member of a subfamily of immunoglobulin receptors with five immunoglobulin-like domains in the extracellular domain. This protein binds to T-cell differentiation antigene CD6, and is implicated in the processes of cell adhesion and migration.

The mature mesenchymal stem cells can also be characterized by the non-expression of any one or more, or all of the following markers: CD14, CD34, CD45, CD11a, CD19, and HLA-DR.

The term "CD14" as used herein refers to the protein encoded by the CD14 gene, which is a surface antigen that is preferentially expressed on monocytes/macrophages. It cooperates with other proteins to mediate the innate immune response to bacterial lipopolysaccharide.

The term "CD34" as used herein refers to the protein encoded by the CD34 gene. It may play a role in the attachment of stem cells to the bone marrow extracellular matrix or to stromal cells. This single-pass membrane protein is highly glycosylated and phosphorylated by protein kinase C.

The term "CD45" as used herein refers to the protein encoded by the PTPRC gene. It is a member of the protein tyrosine phosphatase (PTP) family. PTPs are known to be signaling molecules that regulate a variety of cellular processes including cell growth, differentiation, mitosis, and oncogenic transformation. CD45 contains an extracellular domain, a single transmembrane segment and two tandem intracytoplasmic catalytic domains, and thus is classified as a receptor type PTP. CD45 has been shown to be an essential regulator of T- and B-cell antigen receptor signaling. It functions through either direct interaction with components of the antigen receptor complexes, or by activating various Src family kinases required for the antigen receptor signaling. CD45 also suppresses JAK kinases, and thus functions as a regulator of cytokine receptor signaling.

The term "CD11a" as used herein refers to the protein encoded by the CDK11A gene. It is a member of the serine/threonine protein kinase family, and may plan a roll in cell apoptosis. Members of this kinase family are known to be essential for eukaryotic cell cycle control.

The term "CD19", as known as "B-lymphocyte antigen CD19", is the protein encoded by the CD19 gene. Lymphocytes proliferate and differentiate in response to various concentrations of different antigens. The ability of the B cell to respond in a specific, yet sensitive manner to the various antigens is achieved with the use of low-affinity antigen receptors. CD19 is a cell surface molecule that assembles with the antigen receptor of B lymphocytes and thus decreases the threshold for antigen receptor-dependent stimulation.

The term "HLA-DR" (Human Leukocyte Antigen—antigen D Related) as used herein refers to an MHC class II cell surface receptor encoded by the human leukocyte antigen complex on chromosome 6 region 6p21.31. The complex of HLA-DR and its ligand, a peptide of 9 amino acids in length or longer, constitutes a ligand for the T-cell receptor (TCR). HLA (human leukocyte antigens) were originally defined as cell surface antigens that mediate graft-versus-host disease, which resulted in the rejection of tissue transplants in HLA-mismatched donors.

The term "mesoderm" as used herein refers to one of the three primary germ layers in the very early embryo. The other two layers are the ectoderm (outside layer) and endoderm (inside layer), with the mesoderm as the middle layer between them. It is formed through a process called gastrulation. There are three important components, the paraxial mesoderm, the intermediate mesoderm and the lateral plate mesoderm. The paraxial mesoderm forms the somitomeres, which give rise to mesenchyme of the head and organize into somites in occipital and caudal segments, forming sclerotome (cartilage and bone), and dermatome (subcutaneous tissue of the skin). Signals for somite differentiation are derived from surroundings structures, including the notochord, neural tube and epidermis. The intermediate mesoderm connects the paraxial mesoderm with the lateral plate, eventually it differentiates into urogenital structures consisting of the kidneys, gonads, their associated ducts, and the adrenal glands.

The term "lateral plate mesoderm" as used herein refers to a type of mesoderm that is found at the periphery of the embryo, it is a precursor tissue of vascular lineages that could give rise to the heart, blood vessels and blood cells of the circulatory system as well as to the mesodermal component of the limbs. The lateral plate mesoderm is split into two layers, the somatic lateral plate mesoderm, which forms the future body wall, and the splanchnic lateral plate mesoderm, which forms the circulatory system.

In some examples, the lateral plate mesoderm cells to be cultured in the mesenchymal stem cell culture medium can be obtained using controlled differentiation of embryonic stem cells. In some other examples, the lateral plate mesoderm cells to be cultured in the mesenchymal stem cell culture medium can be obtained using controlled differentiation of induced pluripotent stem cells (iPSCs). When lateral plate mesoderm cells are obtained using controlled differentiation of iPSCs, such mesoderm cells are referred to as "lateral plate mesoderm-like cells".

The lateral plate mesoderm cells or lateral plate mesoderm-like cells to be cultured in the mesenchymal stem cell culture medium are characterized by the expression of any one or more, or all of the following panel of markers: FOXF1, Hand1, APLNR1, PDGFRa and PDGFRβ. A subset of these markers may also be used to characterize the lateral plate mesoderm cells or lateral plate mesoderm-like cells to be cultured. Thus, in some examples, the lateral plate mesoderm cells cells or lateral plate mesoderm-like cells to be cultured in the mesenchymal stem cell culture medium are characterized by any one or more, or all of the following markers: FOXF1, Hand1 and APLNR1.

The term "FOXF1" as used herein refers to the protein encoded by the FOXF1 gene. This gene belongs to the forkhead family of transcription factors which is characterized by a distinct forkhead domain. Diseases associated with FOXF1 include alveolar capillary dysplasia with misalignment of pulmonary veins and alveolar capillary dysplasia. Among its related pathways are embryonic and induced pluripotent stem cell differentiation pathways and lineage-specific markers and FOXA2 and FOXA3 transcription factor networks.

The term "Hand1" as used herein refers to the protein encoded by the HAND1 gene. This protein belongs to the basic helix-loop-helix family of transcription factors. Hand1 is one of two closely related family members, the HAND proteins, which are asymmetrically expressed in the developing ventricular chambers and play an essential role in cardiac morphogenesis. It has been suggested that this transcription factor may be required for early trophoblast differentiation. Diseases associated with Hand1 include hypoplastic left heart syndrome and tetralogy of fallot. Among its related pathways are transcriptional regulatory network in embryonic stem cell and heart development.

The term "APLNR1" or "Apelin Receptor 1" as used interchangeably herein refers to one transcript variant (resulting from alternative splicing) of the protein encoded by the APLNR gene. This protein is an apelin receptor that inhibits adenylate cyclase activity and plays a counter-regulatory role against the pressure action of angiotensin II by exerting hypertensive effect. It functions in the cardiovascular and central nervous systems, in glucose metabolism, in embryonic and tumor angiogenesis and as a human immunodeficiency virus (HIV-1) co-receptor.

The term "PDGFRα" as used herein refers to platelet-derived growth factor receptor α. The molecular mass of the mature, glycosylated PDGFRα protein is approximately 170 kDA.

The term "PDGFRβ" as used herein refers to platelet-derived growth factor receptor β. The molecular mass of the mature, glycosylated PDGFRβ protein is approximately 180 kDA.

Both PDGFRα and PDGFRβ are receptor tyrosine kinases, which are transmembrane proteins consisting of an extracellular ligand binding domain, a transmembrane domain and an intracellular tyrosine kinase domain. These receptors bind to platelet-derived growth factors (PDGFs) and thereby become active in stimulating cell signaling pathways that elicit responses such as cellular growth and differentiation.

As used herein, the term "extracellular matrix" or "ECM" refers to a collection of extracellular molecules secreted by cells that provides structural and biochemical support to the surrounding cells. Because multi-cellularity evolved independently in different multicellular lineages, the composition of ECM varies between multicellular structures. However, cell adhesion, cell-to-cell communication and differentiation are common functions of the ECM.

The ECM is generally composed of an interlocking mesh of fibrous proteins and glycosaminoglycans (GAGs). GAGs are carbohydrate polymers and are usually attached to extracellular matrix proteins to form proteoglycans. Proteoglycans have a net negative charge that attracts positively charged sodium ions (Na+), which attracts water molecules via osmosis, keeping the ECM and resident cells hydrated. Proteoglycans may also help to trap and store growth factors within the ECM. Examples of proteoglycans found within the extracellular matrix include but are not limited to, heparan sulphate, chondroitin sulphate and keratan sulphate.

Heparan sulfate (HS) is a linear polysaccharide found in all animal tissues. It occurs as a proteoglycan in which two or three HS chains are attached in close proximity to cell surface or ECM proteins. It is in this form that HS binds to a variety of protein ligands and regulates a wide variety of biological activities, including developmental processes, angiogenesis, blood coagulation, and tumour metastasis. In the extracellular matrix, especially basement membranes, the multi-domain proteins perlecan, agrin, and collagen XVIII are the main proteins to which heparan sulfate is attached.

Chondroitin sulfates contribute to the tensile strength of cartilage, tendons, ligaments, and walls of the aorta. They have also been known to affect neuroplasticity.

Keratan sulfates have a variable sulfate content and, unlike many other GAGs, do not contain uronic acid. They are present in the cornea, cartilage, bones, and the horns of animals.

Hyaluronic acid (or "hyaluronan") is a polysaccharide consisting of alternating residues of D-glucuronic acid and N-acetylglucosamine, and unlike other GAGs, is not found as a proteoglycan. Hyaluronic acid in the extracellular space confers upon tissues the ability to resist compression by providing a counteracting turgor (swelling) force by absorbing significant amounts of water. Hyaluronic acid is thus found in abundance in the ECM of load-bearing joints. It is also a chief component of the interstitial gel. Hyaluronic acid is found on the inner surface of the cell membrane and is translocated out of the cell during biosynthesis. Hyaluronic acid acts as an environmental cue that regulates cell behavior during embryonic development, healing processes, inflammation, and tumor development. It interacts with a specific transmembrane receptor, CD44.

Collagens are the most abundant protein in the ECM. Collagens are present in the ECM as fibrillar proteins and give structural support to resident cells. Collagen is exocytosed in precursor form (procollagen), which is then cleaved by procollagen proteases to allow extracellular assembly.

Elastins, in contrast to collagens, give elasticity to tissues, allowing them to stretch when needed and then return to their original state. This is useful in blood vessels, the lungs, in skin, and the ligamentum nuchae, and these tissues contain high amounts of elastins. Elastins are synthesized by fibroblasts and smooth muscle cells. Elastins are highly insoluble, and tropoelastins are secreted inside a chaperone molecule, which releases the precursor molecule upon contact with a fiber of mature elastin. Tropoelastins are then deaminated to become incorporated into the elastin strand.

Fibronectins are glycoproteins that connect cells with collagen fibers in the ECM, allowing cells to move through the ECM. Fibronectins bind collagen and cell-surface integrins, causing a reorganization of the cell's cytoskeleton to facilitate cell movement. Fibronectins are secreted by cells in an unfolded, inactive form. Binding to integrins unfolds fibronectin molecules, allowing them to form dimers so that they can function properly. Fibronectins also help at the site of tissue injury by binding to platelets during blood clotting and facilitating cell movement to the affected area during wound healing.

Laminins are proteins found in the basal laminae of virtually all animals. Rather than forming collagen-like fibers, laminins form networks of web-like structures that resist tensile forces in the basal lamina. They also assist in cell adhesion. Laminins bind other ECM components such as collagens and nidogens.

In one specific example, the ECM used in the method of the present disclosure is fibronectin.

The term "fibroblast growth factor" or the short form "FGF" as used herein refers to a family of growth factors, with members involved in angiogenesis, wound healing, embryonic development and various endocrine signaling pathways. The fibroblast growth factors are heparin-binding proteins and interactions with cell-surface-associated heparan sulfate proteoglycans have been shown to be essential for fibroblast growth factor signal transduction. Fibroblast growth factors are key players in the processes of proliferation and differentiation of wide variety of cells and tissues. Fibroblast growth factors are multifunctional proteins with a wide variety of effects; they are most commonly mitogens but also have regulatory, morphological, and endocrine effects. They have been alternately referred to as "pluripotent" growth factors and as "promiscuous" growth factors due to their multiple actions on multiple cell types. Promiscuous refers to the biochemistry and pharmacology concept of how a variety of molecules can bind to and elicit a response from single receptor. In the case of fibroblast growth factor, four receptor subtypes can be activated by more than twenty different fibroblast growth factor ligands. Thus the functions of FGFs in developmental processes include mesoderm induction, antero-posterior patterning, limb development, neural induction and neural development, and in mature tissues/systems angiogenesis, keratinocyte organization, and wound healing processes.

Fibroblast growth factors are critical during normal development of both vertebrates and invertebrates and any irregularities in their function leads to a range of developmental defects. One important function of FGF1 and FGF2 is the promotion of endothelial cell proliferation and the physical organization of endothelial cells into tube-like structures. They thus promote angiogenesis, the growth of new blood vessels from the pre-existing vasculature. FGF1 can be used to induce angiogenesis in the heart, as well as stimulating blood vessel growth. FGF1 and FGF2 stimulate angiogenesis and the proliferation of fibroblasts that give rise to granulation tissue, which fills up a wound space/cavity early in the wound-healing process. FGF7 and FGF10 (also known as keratinocyte growth factors KGF and KGF2, respectively) stimulate the repair of injured skin and mucosal tissues by stimulating the proliferation, migration and differentiation of epithelial cells, and they have direct chemotactic effects on tissue re-modelling. Another fibroblast growth factor family member, FGF8, regulates the size and positioning of the functional areas of the cerebral cortex (Brodmann's Areas). FGFs are also important for maintenance of the adult brain.

Members of the FGF19 subfamily (FGF15, FGF19, FGF21, and FGF23) can act in an endocrine fashion on far-away tissues, such as intestine, liver, kidney, adipose, and bone. For example, FGF15 and FGF19 (FGF15/19) are produced by intestinal cells but act on FGFR4-expressing liver cells to down-regulate the key gene (CYP7A1) in the bile acid synthesis pathway. FGF23 is produced by bone but acts on FGFR1-expressing kidney cells to regulate the synthesis of vitamin D and phosphate homeostasis. In humans, 22 members of the FGF family have been identified, all of which are structurally related signaling molecules. FGF1 through to FGF10 are known to all bind fibroblast growth factor receptors (FGFRs). FGF1 is also known as acidic, and FGF2 is also known as basic fibroblast growth factor. FGF11, FGF12, FGF13, and FGF14, also known as FGF homologous factors 1 to 4 (FHF1-FHF4), have been shown to have distinct functions compared to the FGFs. Although these factors possess remarkably similar sequence homology, they do not bind FGFRs and are involved in intracellular processes unrelated to the FGFs. This group is also known as "iFGF". Human FGF18 is involved in cell development and morphogenesis in various tissues including cartilage. Human FGF20 was identified based on its homology to *Xenopus* FGF-20 (XFGF-20). FGF15 through FGF23 were described later and functions are still being characterized. FGF15 is the mouse ortholog of human FGF19 (there is no human FGF15) and, where their functions are shared, they are often described as FGF15/19. In contrast to the local activity of the other FGFs, FGF15/19, FGF21 and FGF23 have systemic effects. The crystal structures of FGF1 have been solved and found to be related to interleukin 1-beta. Both families have the same beta trefoil fold consisting of 12-stranded beta-sheet structure, with the beta-sheets are arranged in 3 similar lobes around a central axis, 6 strands forming an anti-parallel beta-barrel. In general, the beta-sheets are well-preserved and the crystal structures superimpose in these areas. The intervening loops are less well-conserved—the loop between beta-strands 6 and 7 is slightly longer in interleukin-1 beta.

In one example, the fibroblast growth factor (FGF) used in the mesenchymal stem cell culture medium is capable of binding to fibroblast growth factor receptors (FGFRs). The FGF can be, for example, FGF1, FGF2, FGF3, FGF4, FGF5, FGF6, FGF7, FGF8, FGF9 and FGF10. In one specific example, the FGF is FGF2.

In some examples, the fibroblast growth factor in the mesenchymal stem cell culture medium is at a concentration of between about 0.5 to about 100 ng/ml, or between about 1 to about 90 ng/ml, or between about 1.5 to about 80 ng/ml, or between about 2 to about 70 ng/ml, or between about 2.5 to about 60 ng/ml, or between about 3 to about 50 ng/ml, or between about 3.5 to about 45 ng/ml, or between about 4 to about 40 ng/ml, or between about 4.5 to about 35 ng/ml, or between about 5 to about 30 ng/ml, or between about 5 to about 25 ng/ml, or between about 5 to about 20 ng/ml, or between about 5 to about 15 ng/ml, or between about 5 to about 10 ng/ml, or between about 5 to about 7.5 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 ng/ml. In some specific examples, the fibroblast growth factor in the mesenchymal stem cell culture medium is at a concentration of between about 1 to about 100 ng/ml. In one specific example, the fibroblast growth factor in the mesenchymal stem cell culture medium is at a concentration of 5 ng/ml. In another specific example, the fibroblast growth factor in the mesenchymal stem cell culture medium is at a concentration of 10 ng/ml.

The term "platelet-derived growth factor" or the short form "PDGF" as used herein refers to growth factors that play a significant role in blood vessel formation (angiogenesis). PDGF is a potent mitogen for cells of mesenchymal origin, including fibroblasts, smooth muscle cells and glial cells.

There are four types of PDGF subunits—PDGFA, PDGFB, PDGFC and PDGFD. PDGF is usually present as a dimeric glycoprotein of two subunits, and subunits PDGFA and PDGFB are the only subunits that can form heterodimers. Examples of the dimeric isoforms include PDGFAA, PDGFBB, PDGFCC, PDGFDD and PDGFAB. In one specific example, the PDGF used in the mesenchymal stem cell culture medium is PDGFAB.

In some examples, the PDGF in the mesenchymal stem cell culture medium is at a concentration of between about 0.5 to about 100 ng/ml, or between about 1 to about 90 ng/ml, or between about 1.5 to about 80 ng/ml, or between about 2 to about 70 ng/ml, or between about 2.5 to about 60 ng/ml, or between about 3 to about 50 ng/ml, or between about 3.5 to about 45 ng/ml, or between about 4 to about 40 ng/ml, or between about 4.5 to about 35 ng/ml, or between about 5 to about 30 ng/ml, or between about 5 to about 25 ng/ml, or between about 5 to about 20 ng/ml, or between about 5 to about 15 ng/ml, or between about 5 to about 10 ng/ml, or between about 5 to about 7.5 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 ng/ml. In some specific examples, the PDGF in the mesenchymal stem cell culture medium is at a concentration of between about 1 to about 50 ng/ml. In one specific example, the PDGF in the mesenchymal stem cell culture medium is at a concentration of 5 ng/ml.

The term "epidermal growth factor family protein" or the short form "(EGF) family protein" as used herein refers to the family of proteins that stimulate cell growth, proliferation and differentiation by binding to the epidermal growth factor receptor (EGFR). An EGF family protein acts by binding with high affinity to EGFR on the cell surface. This stimulates ligand-induced dimerization and activates the intrinsic protein-tyrosine kinase activity of the receptor. The tyrosine kinase activity, in turn, initiates a signal transduction cascade that results in a variety of biochemical changes within the cell that ultimately lead to DNA synthesis and cell proliferation.

Examples of EGF family protein include but are not limited to, EGF, Heparin-binding EGF-like growth factor (HB-EGF), transforming growth factor-α (TGF-α), Amphiregulin (AR), Epiregulin (EPR), Epigen, Betacellulin (BTC), neuregulin-1 (NRG1), neuregulin-2 (NRG2), neuregulin-3 (NRG3) and neuregulin-4 (NRG4). In one specific example, the EGF family protein is EGF.

In some examples, the EGF family protein in the mesenchymal stem cell culture medium is at a concentration of between about 0.5 to about 100 ng/ml, or between about 1 to about 90 ng/ml, or between about 1.5 to about 80 ng/ml, or between about 2 to about 70 ng/ml, or between about 2.5 to about 60 ng/ml, or between about 3 to about 50 ng/ml, or between about 3.5 to about 45 ng/ml, or between about 4 to about 40 ng/ml, or between about 4.5 to about 35 ng/ml, or between about 5 to about 30 ng/ml, or between about 7.5 to about 25 ng/ml, or between about 10 to about 20 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 ng/ml. In one specific example, the EGF in the mesenchymal stem cell culture medium is at a concentration of 10 ng/ml.

The term "ascorbic acid" as used herein is also known as Vitamin C, the IUPAC name of which is 2-oxo-L-threo-hexono-1,4-lactone-2,3-enediol or (R)-3,4-dihydroxy-5-((S)-1,2-dihydroxyethyl)furan-2(5H)-one.

In some examples, the ascorbic acid in the mesenchymal stem cell culture medium is at a concentration of between about 1 to about 500 µg/ml, or between about 5 to about 450 µg/ml, or between about 10 to about 400 µg/ml, or between about 20 to about 350 µg/ml, or between about 25 to about 300 µg/ml, or between about 30 to about 250 µg/ml, or between about 35 to about 200 µg/ml, or between about 40 to about 180 µg/ml, or between about 45 to about 160 µg/ml, or between about 50 to about 140 µg/ml, or between about 50 to about 120 µg/ml, or between about 50 to about 110 µg/ml, or between about 50 to about 100 µg/ml, or between about 50 to about 90 µg/ml, or between about 50 to about 80 µg/ml, or between about 50 to about 70 µg/ml, or between about 50 to about 60 µg/ml, or at about 1, 5, 10, 15, 20, 25, 30, 35, 40, 45, 50, 60, 70, 80, 90, 100, 150, 200, 250, 300, 350, 400, 450 or 500 µg/ml. In some specific examples, the ascorbic acid in the mesenchymal stem cell culture medium is at a concentration of between about 5 to about 100 µg/ml. In one specific example, the ascorbic acid in the mesenchymal stem cell culture medium is at a concentration of 50 µg/ml.

In some examples, the method of the first aspect can further comprise the use of transforming growth factor beta (TGF-β) in the mesenchymal stem cell culture medium.

The term "transforming growth factor beta" or the short form "TGF-β" as used herein refers to a polypeptide member of the transforming growth factor beta superfamily of cytokines. It is a secreted protein that performs many cellular functions, including, but not limited to, the control of cell growth, cell proliferation, cell differentiation and apoptosis. In humans, TGF-β1 is encoded by the TGFB1 gene. Other members of this superfamily include, but are not limited to, bone morphogenetic proteins (BMPs), growth and differentiation factors (GDFs), anti-müllerian hormone (AMH), Activin (for example, Activin A, B and AB), Nodal and different TGF-β's (for example, TGFβ-1, TGFβ-2, TGFβ-3). In some examples, the TGF-β in the mesenchymal stem cell culture medium as disclosed herein is TGFβ-1, TGFβ-2 or TGFβ-3. In one specific example, the TGF-β used is TGFβ-1.

TGF-β and the related proteins of said transforming growth factor beta superfamily of cytokines are involved in the so-called TGF-β signaling pathway. This pathway is involved in many cellular processes in both the adult organism and the developing embryo, including, but not limited to, cell growth, cell differentiation, apoptosis, cellular homeostasis and other cellular functions. In spite of the wide range of cellular processes that the TGF-β signaling pathway regulates, the process is relatively straightforward. TGF-β superfamily ligands bind to a type II receptor (usually a serine/threonine receptor kinase), which recruits and phosphorylates a type I receptor. The type I receptor then phosphorylates receptor regulated SMADs (R-SMADs) which can now bind the co-SMAD SMAD4 (also known as SMAD family member n° 4, Mothers against decapentaplegic homolog 4, JIP, MADH4, MYHRS, or DPC4 (Deleted in Pancreatic Cancer-4)). R-SMAD/co-SMAD complexes accumulate in the nucleus where they act as transcription factors and participate in the regulation of target gene expression.

In some examples, the transforming growth factor beta (TGF-β) in the mesenchymal stem cell culture medium is at a concentration of between about 1 ng/ml to about 100 µg/ml, or between about 5 ng/ml to about 90 µg/ml, or between about 10 ng/ml to about 80 µg/ml, or between about 15 ng/ml to about 70 µg/ml, or between about 20 ng/ml to about 60 µg/ml, or between about 30 ng/ml to about 50 µg/ml, or between about 40 ng/ml to about 45 µg/ml, or between about 50 ng/ml to about 40 µg/ml, or between about 60 ng/ml to about 35 µg/ml, or between about 70 ng/ml to about 30 µg/ml, or between about 80 ng/ml to about 25 µg/ml, or between about 90 ng/ml to about 20 µg/ml, or between about 100 ng/ml to about 15 µg/ml, or between about 150 ng/ml to about 10 µg/ml, or between about 200 ng/ml to about 5 µg/ml, or between about 300 ng/ml to about 2 µg/ml, or between about 400 ng/ml to about 1 µg/ml, or between about 500 ng/ml to about 900 ng/ml, or between about 600 ng/ml to about 800 ng/ml, or at about 0.5, 1, 2, 3, 4, 5, 6, 7, 8, 9, 10, 12, 14, 16, 18, 20, 25, 30, 40 or 50 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 µg/ml. In some examples, the TGF-β in the mesenchymal stem cell culture medium is at a concentration of between about 1 to about 20 ng/ml. In one specific example, the TGF-β in the mesenchymal stem cell culture medium is at a concentration of 10 ng/ml.

In some examples of the method of the first aspect, the lateral plate or lateral plate-like mesoderm cells are cultured on an extracellular matrix in the mesenchymal stem cell culture medium for about 1 to 20 days, or for about 1 to 18 days, or for about 1 to 16 days, or for about 1 to 14 days, or for about 1 to 12 days, or for about 3 to 12 days, or for about 5 to 12 days, or for about 6 to 12 days, or for about 8 to 12 days, or for about 10 to 12 days, or for about 1, 2, 3, 4, 5, 6, 7, 8, 9, 10, 11, 12, 13, 14, 15, 16, 17, 18, 19, 20 days, in order to obtain the mesenchymal stem cells. In one specific example, the lateral plate or lateral plate-like mesoderm cells are cultured on an extracellular matrix in the mesenchymal stem cell culture medium for about 11 days to obtain the mature mesenchymal stem cells.

In one example of the method of the first aspect, the lateral plate or lateral plate-like mesoderm cells are cultured under a serum-free condition. Advantages of using a serum-free condition include but are not limited to, avoiding the non-defined nature of serum which may result in batch-to-batch variability in composition, and reducing the risk of contamination. These advantages allow the mature mesenchymal stem cells obtained using the methods as disclosed herein to be used for clinical applications.

In one example of the method of the first aspect, the lateral plate or lateral plate-like mesoderm cells are cultured without using any feeder cells.

The term "feeder cell" as used herein refers to a layer of cells which provides extracellular secretions to facilitate the growth of the stem cells. Feeder cells are unable to divide, thus it differs from a co-culture system because only one type of cells (i.e. the stem cells) are capable of proliferating. Typical examples of feeder cells are fibroblasts, which are the most common cells in connective tissues.

One advantage of a feeder-free cell culture system with defined components is that it eliminates the undefined bio-active molecules secreted by feeders.

The lateral plate or lateral plate-like mesoderm cells to be cultured in the mesenchymal stem cell culture medium can be obtained, for example, from primitive streak mesendoderm cells (or from primitive streak-like mesendoderm cells). For example, referring to FIG. 1, this is directed to the culturing of the primitive streak (PS)/mesendoderm cells from day 2 to day 10. Thus, in one example, the method of the first aspect further comprises, before culturing the lateral plate mesoderm cells or lateral plate-like mesoderm cells:

culturing primitive streak mesendoderm cells to obtain lateral plate mesoderm cells or culturing primitive streak-like mesendoderm cells to obtain lateral plate-like mesoderm cells.

In some examples, culturing the primitive streak or primitive streak-like mesendoderm cells to obtain lateral plate or lateral plate-like mesoderm cells comprises culturing the primitive streak or primitive streak-like mesendoderm cells on an extracellular matrix in a lateral plate mesoderm cell culture medium comprising:
(1) fibroblast growth factor;
(2) bone morphogenetic protein;
(3) Rho-associated protein kinase (ROCK) inhibitor; and
(4) follistatin.

The term "primitive streak" as used herein refers to a structure that forms in the blastula during the early stages of embryonic development. It forms on the dorsal face of the developing embryo, toward the caudal or posterior end. During mammalian embryonic development, the primitive streak initiates the differentiation of pluripotent epiblast cells into germ layers. The term "mesendoderm" as used herein refers to an embryonic tissue layer which differentiates into mesoderm and endoderm.

The term "primitive streak-like mesendoderm" as used herein refers to intermediate cells formed during induced pluripotency (e.g. of human somatic cells), which transiently show gene expression profiles resembling primitive streak mesendoderm.

In some example, the primitive streak or the primitive streak-like mesendoderm cells are characterized by any one or more, or all of the following markers: MIXL1, T, GSC and Wnt3.

The term "MIXL1" as used herein refers to the protein endoed by the MIXL1 gene. It is a transcription factor that plays a central role in proper axial mesendoderm morphogenesis and endoderm formation. It is required for efficient differentiation of cells from the primitive streak stage to blood, by acting early in the recruitment and/or expansion of mesodermal progenitors to the hemangioblastic and hematopoietic lineages. It is also involved in the morphogenesis of the heart and the gut during embryogenesis.

The term "T" when as used herein in the context of a marker for the primitive streak mesendoderm cells (or the primitive streak-like mesendoderm cells), refers to the protein encoded by the T (T Brachyury Transcription Factor) gene. It is an embryonic nuclear transcription factor that binds to a specific DNA element, the palindromic T-site, through a region in its N-terminus, called the T-box. It effects transcription of genes required for mesoderm formation and differentiation.

The term "Goosecoid Homeobox" or the short form "GSC" as used herein refers to the protein encoded by the GSC gene. It is a member of the bicoid subfamily of the paired (PRD) homeobox family of proteins. GSC acts as a transcription factor and may be auto-regulatory. A similar protein in mice plays a role in craniofacial and rib cage development during embryogenesis.

The term "Wnt3" as used herein refers to the protein encoded by the WNT3 gene. It is a member of the Wnt protein family of secreted signaling proteins. The Wnt family proteins have been implicated in oncogenesis and in several developmental processes, including regulation of cell fate and patterning during embryogenesis.

In some examples, the primitive streak or the primitive streak-like mesendoderm cells are cultured on an extracellular matrix in the lateral plate mesoderm cell culture medium as mentioned above for about 1 to 12 days, or for about 2 to 12 days, or for about 4 to 12 days, or for about 6 to 12 days, or for about 8 to 12 days, or for about 8 to 10 days, or for about 1, 2, 3, 4, 5, 6, 7, 8, 9, 11 or 12 days. In one specific example, the primitive streak or the primitive streak-like mesendoderm cells are cultured on an extracellular matrix in the lateral plate mesoderm cell culture medium for 8 days.

In some examples, culturing primitive streak or primitive streak-like mesendoderm cells to obtain lateral plate or lateral plate-like mesoderm cells comprises two steps, wherein some of the components of the lateral plate mesoderm cell culture medium used in the two steps are different. Accordingly, in some examples, culturing primitive streak or primitive streak-like mesendoderm cells to obtain lateral plate or lateral plate-like mesoderm cells comprises the following:
(i) culturing the primitive streak or primitive streak-like mesendoderm cells on an extracellular matrix in a first lateral plate mesoderm cell culture medium; and
(ii) subsequently culturing the primitive streak or primitive streak-like mesendoderm cells from (i) on an extracellular matrix in a second lateral plate mesoderm cell culture medium, wherein the first lateral plate mesoderm cell culture medium comprises:
(1) fibroblast growth factor;
(2) bone morphogenetic protein;
(3) Rho-associated protein kinase (ROCK) inhibitor; and
(4) follistatin.
and wherein the second lateral plate mesoderm cell culture medium comprises:
(5) fibroblast growth factor;
(6) bone morphogenetic protein; and
(7) follistatin.

In one example, in step (i) above, the primitive streak or primitive streak-like mesendoderm cells are cultured on an extracellular matrix in the first lateral plate mesoderm cell culture medium for a short period of time, for example, during the time of passaging and overnight after the passaging, which lasts for about 1 to 6 hours, or for about 1 to 12 hours, or for about 1 to 18 hours, or for about 1 to 24 hours, or for about 1, 3, 6, 9, 12, 15, 18 or 24 hours. Subsequently, in step (ii) above, the primitive streak or primitive streak-like mesendoderm cells are cultured on an extracellular matrix in the second lateral plate mesoderm cell culture medium for a longer period of time, for example, for about 1 to 4 days, or for about 1 to 6 days, or for about 1 to 8 days, or for about 1 to 10 days, or for about 1 to 12 days, or for about 1, 2, 3, 4, 5, 6, 7, 8, 9, 11 or 12 days.

The fibroblast growth factor (FGF) used in the lateral plate mesoderm cell culture medium can be, for example, FGF1, FGF2, FGF3, FGF4, FGF5, FGF6, FGF7, FGF8, FGF9 and FGF10. In one specific example, the FGF is FGF2. In some examples, the FGF in the lateral plate mesoderm cell culture medium is at a concentration of between about 0.5 to about 100 ng/ml, or between about 1 to about 90 ng/ml, or between about 2 to about 80 ng/ml, or between about 3 to about 70 ng/ml, or between about 4 to about 60 ng/ml, or between about 5 to about 50 ng/ml, or between about 6 to about 45 ng/ml, or between about 7 to about 40 ng/ml, or between about 8 to about 35 ng/ml, or between about 9 to about 30 ng/ml, or between about 10 to about 25 ng/ml, or between about 15 to about 20 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 ng/ml. In some specific examples, the FGF in the lateral plate mesoderm cell culture medium is at a concentration of between about 1 to about 100 ng/ml. In one specific example, the fibroblast growth factor in the lateral plate mesoderm cell culture medium is at a concentration of 20 ng/ml.

The term "bone morphogenetic protein" or the short term "BMP" as used herein refers to a group of proteins which interact with specific receptors on the cell surface, referred to as bone morphogenetic protein receptors (BMPRs). Signal transduction through BMPRs results in mobilization of members of the SMAD family of proteins. The signaling pathways involving BMPs, BMPRs and SMADs are important in the development of the heart, central nervous system, and cartilage, as well as post-natal bone development.

Examples of BMPs which could be used in the lateral plate mesoderm cell culture medium include but are not limited to, BMP1, BMP2, BMP3, BMP4, BMP5, BMP6, BMP7, BMP8a, BMP8b, BMP10 and BMP15. In one specific example, the BMP used is BMP4. In some examples, the BMP in the lateral plate mesoderm cell culture medium is at a concentration of between about 1 to about 200 ng/ml, or between about 5 to about 180 ng/ml, or between about 10 to about 160 ng/ml, or between about 15 to about 140 ng/ml, or between about 20 to about 120 ng/ml, or between about 25 to about 100 ng/ml, or between about 30 to about 90 ng/ml, or between about 35 to about 80 ng/ml, or between about 40 to about 70 ng/ml, or between about 40 to about 60 ng/ml, or between about 40 to about 55 ng/ml, or between about 40 to about 50 ng/ml, or between about 40 to about 45 ng/ml, or at about 1, 2, 3, 4, 5, 6, 7, 8, 9, 10, 12.5, 15, 17.5, 20, 22.5, 25, 27.5, 30, 35, 40, 45, 50, 55, 60, 65, 70, 75, 80, 85, 90, 95, 100, 110, 120, 130, 140, 150, 160, 170, 180, 190 or 200 ng/ml. In some specific examples, the BMP in the lateral plate mesoderm cell culture medium is at a concentration of between about 1 to about 80 ng/ml. In one specific example, the BMP in the lateral plate mesoderm cell culture medium is at a concentration of 40 ng/ml.

The term "Rho-associated protein kinase" or the short form "ROCK" as used herein refers to kinase of the AGC (PKA/PKG/PKC) family of serine-threonine kinases. It is involved mainly in regulating the shape and movement of cells by acting on the cytoskeleton. ROCKs (ROCK1 and ROCK2) occur in mammals (human, rat, mouse, cow), zebrafish, *Xenopus*, invertebrates and chicken. Human ROCK1 has a molecular mass of 158 kDa and is a major downstream effector of the small GTPase RhoA. Mammalian ROCK consists of a kinase domain, a coiled-coil region and a Pleckstrin homology (PH) domain, which reduces the kinase activity of ROCKs by an autoinhibitory intramolecular fold if RhoA-GTP is not present.

The term "Rho-associated protein kinase inhibitor" or the short form "ROCK inhibitor" thus refers to a compound that inhibits the activity of ROCK. Examples of ROCK inhibitors include but are not limited to Y-27632 (i.e. (R)-(+)-trans-4-(1-Aminoethyl)-N-(4-Pyridyl)cyclohexanecarboxamide dihydrochloride, IUPAC name (1R,4r)-4-((R)-1-aminoethyl)-N-(pyridin-4-yl)cyclohexanecarboxamide) and fasudil (i.e. IUPAC name 5-(1,4-Diazepane-1-sulfonyl)isoquinoline). In one specific example, the ROCK inhibitor used in the lateral plate mesoderm cell culture medium is Y-27632. In some examples, the ROCK inhibitor in the lateral plate mesoderm cell culture medium is at a concentration of between about 1 to about 100 μM, or between about 1.5 to about 90 μM, or between about 2 to about 80 μM, or between about 2.5 to about 70 μM, or between about 3 to about 60 μM, or between about 3.5 to about 50 μM, or between about 4 to about 40 μM, or between about 4.5 to about 30 μM, or between about 5 to about 2504, or between about 5 to about 20 μM, or between about 5 to about 15 μM, or between about 5 to about 10 μM, or at about 1, 2, 3, 4, 5, 6, 7, 8, 9, 10, 12.5, 15, 17.5, 20, 22.5, 25, 27.5, 30, 35, 40, 45, 50, 55, 60, 65, 70, 75, 80, 85, 90, 95 or 100 μM. In one specific example, the ROCK inhibitor in the lateral plate mesoderm cell culture medium is at a concentration of 504.

The term "follistatin" as used herein refers to the protein encoded by the FST gene. Follistatin is a single-chain gonadal protein that specifically inhibits follicle-stimulating hormone release. In some examples, the follistatin in the lateral plate mesoderm cell culture medium is at a concentration of between about 1 ng/ml to about 600 ng/ml, or between about 5 ng/ml to about 550 ng/ml, or between about 10 ng/ml to about 500 ng/ml, or between about 20 to about 450 ng/ml, or between about 30 to about 400 ng/ml, or between about 40 to about 350 ng/ml, or between about 50 to about 300 ng/ml, or between about 60 to about 250 ng/ml, or between about 70 to about 200 ng/ml, or between about 80 to about 180 ng/ml, or between about 90 to about 160 ng/ml, or between about 100 to about 140 ng/ml, or between about 100 to about 120 ng/ml, or at about 1, 2.5, 5, 7.5, 10, 20, 30, 40, 50, 60, 70, 80, 90, 100, 110, 120, 130, 140, 150, 160, 170, 180, 190, 200, 220, 240, 260, 280, 300, 350, 400, 450, 500, 550 or 600 ng/ml. In some specific examples, the follistatin in the lateral plate mesoderm cell culture medium is at a concentration of between about 1 ng/ml to about 200 ng/ml. In one specific example, the follistatin in the lateral plate mesoderm cell culture medium is at a concentration of 100 ng/ml.

In one example, culturing the primitive streak or primitive streak-like mesendoderm cells to obtain lateral plate or lateral plate-like mesoderm cells is carried out under a serum-free condition. In another example, the primitive streak or primitive streak-like mesendoderm cells are cultured without using any feeder cells.

The primitive streak or primitive streak-like mesendoderm cells to be cultured in the lateral plate mesoderm cell culture medium can be obtained, for example, from pluripotent stem cells. For example, referring to FIG. 1, this is directed to the culturing of the iPSC/hESC from day 0 to day 2. Thus, in one example, the method of the first aspect further comprises, before culturing the primitive streak or primitive streak-like mesendoderm cells: culturing pluripotent stem cells on an extracellular matrix to obtain primitive streak or primitive streak-like mesendoderm cells.

The term "stem cell" as used herein refers to undifferentiated biological cells that are capable of differentiating into more specialized cells and that are capable of dividing (through mitosis) to produce more stem cells. Stem cells are found in multicellular organisms. In mammals, there are two broad types of stem cells: embryonic stem cells, which are isolated, for example, from the inner cell mass of blastocysts, and adult stem cells, which are found in various tissues. In adult organisms, stem cells and progenitor cells function as a repair system for the body by replenishing adult tissues. In a developing embryo, stem cells can differentiate into all the specialized cells derived from any one of the three primary germ layers, namely ectoderm, endoderm and mesoderm, present in the early stages of embryonic development. Stem cells can also maintain the normal turnover of regenerative organs, such as blood, skin, or intestinal tissues in a developing embryo.

The three commonly known, accessible sources of autologous adult stem cells in humans are the bone marrow, which requires extraction by harvesting cells, usually from the femur or iliac crest; adipose tissue (lipid cells), which requires extraction by liposuction, and blood, which requires extraction, usually through a apheresis machine. Stem cells can also be taken from umbilical cord blood just after birth. Of all stem cell types, autologous harvesting involves the least risk. By definition, autologous cells are obtained from one's own body.

The stem cells may be isolated from any mammalian species, for example, but not limited to, mouse, rat, rabbit, guinea pig, dog, cat, pig, sheep, cow, horse, monkey and human. In one example, the stem cells are obtained from a human.

As used herein, the term "pluripotent stem cell" or "pluripotent cell" refers to a stem cell that has the potential to differentiate into any of the three germ layers: the endoderm, from which, for example, the interior stomach lining, gastrointestinal tract and the lungs develop; the mesoderm, from which, for example, muscle, bone, blood and urogenital structures develop; or the ectoderm, from which, for example, epidermal tissues and nervous system develop. The pluripotent stem cells that could be used to obtain primitive streak mesendoderm cells are embryonic stem cells, and the pluripotent stem cells that could be used to obtain primitive streak-like mesendoderm cells are induced pluripotent stem cells.

The term "embryonic stem cells" as used herein refers to the pluripotent stem cells derived from the inner cell mass of a blastocyst, an early-stage pre-implantation embryo. In one example, the method as disclosed herein is performed without the use of human embryonic stem cells. In yet another example, the method as disclosed herein is performed using embryonic stem cells that are not of human origin. In yet another example, the method as disclosed herein is performed using human embryonic stem cells harvested no later than 14 days after fertilization. An example of human embryonic stem cell line is the H1 cell line.

The term "induced pluripotent stem cells" or the short form "iPSCs" or "iPS cells" as used herein refers to pluripotent stem cells that can be generated directly from adult cells. iPSCs are typically derived by introducing products of specific sets of pluripotency-associated genes, or "reprogramming factors", into a given cell type. Upon introduction of reprogramming factors, cells begin to form colonies that resemble pluripotent stem cells, which can be isolated based on their morphology, conditions that select for their growth, or through expression of surface markers or reporter genes. Examples of pluripotency-associated genes, or "reprogramming factors" include but are not limited to, OCT4, SOX2, NANOG, LIN28, KLF4 and c-Myc, which can be used alone or in combination. Examples of induced pluripotent stem cells include but are not limited to, induced pluripotent stem cells generated from the human fibroblast cell lines BJ and MRC-5.

As used herein, the term "OCT4", also known as octamer-binding transcription factor 4 or POU5F1 (POU domain, class 5, transcription factor 1), refers to a protein that in humans is encoded by the POU5F1 gene. OCT4 is a homeodomain transcription factor of the POU family. This protein is critically involved in the self-renewal of undifferentiated embryonic stem cells. As such, it is frequently used as a marker for undifferentiated cells. OCT4 expression must be closely regulated; too much or too little will cause differentiation of the cells.

The term "SOX2" as used herein refers to SRY (sex determining region Y)-box 2, which is a transcription factor that is essential for maintaining self-renewal, or pluripotency, of undifferentiated embryonic stem cells. SOX2 has a critical role in maintenance of embryonic and neural stem cells. SOX2 is a member of the SOX family of transcription factors, which have been shown to play key roles in many stages of mammalian development. This protein family shares highly conserved DNA binding domains known as HMG (High-mobility group) box domains containing approximately 80 amino acids.

The term "NANOG" as used herein refers to a transcription factor critically involved with self-renewal of undifferentiated embryonic stem cells. In humans, this protein is encoded by the NANOG gene.

The term "LIN28" as used herein refers to a protein that in human is encoded by the LIN28 gene. It is an RNA-binding protein that binds to and enhances the translation of the IGF-2 (insulin-like growth factor 2) mRNA. LIN28 binds to the let-7 pre-microRNA and blocks production of the mature let-7 microRNA in mouse embryonic stem cells. In pluripotent embryonal carcinoma cells, LIN28 is localized in the ribosomes, P-bodies and stress granules. LIN28 is thought to regulate the self-renewal of stem cells. In vertebrates, there are two paralogs present, LIN28A and LIN28B. In mice, LIN28 is highly expressed in mouse embryonic stem cells and during early embryogenesis. LIN28 is highly expressed in human embryonic stem cell and can enhance the efficiency of the formation of induced pluripotent stem cells (iPSCs) from human fibroblasts.

The term "KLF4" as used herein refers to Kruppel-like factor 4, which is a zinc-finger transcription factor of the KLF family of transcription factors, which belongs to the relatively large family of SP1-like transcription factors. KLF4 is involved in the regulation of proliferation, differentiation, apoptosis and somatic cell reprogramming. KLF4 has three C2H2-zinc fingers at its carboxyl terminus that are closely related to another KLF, KLF2. It has two nuclear localization sequences that signals it to localize to the nucleus. In embryonic stem cells, KLF4 has been demonstrated to be a good indicator of stem-like capacity.

The term "c-Myc", also known as "Myc", is a regulator gene that codes for a transcription factor. The protein encoded by this gene is a multifunctional, nuclear phosphoprotein that plays a role in cell cycle progression, apoptosis and cellular transformation. In the human genome, Myc is located on chromosome 8 and is believed to regulate expression of 15% of all genes through binding on enhancer box sequences (E-boxes) and recruiting histone acetyltransferases (HATs). This means that in addition to its role as a classical transcription factor, Myc also functions to regulate global chromatin structure by regulating histone acetylation both in gene-rich regions and at sites far from any known gene.

In some examples, culturing pluripotent stem cells on an extracellular matrix to obtain primitive streak or primitive streak-like mesendoderm cells comprises the following:
(i) culturing the pluripotent stem cells on an extracellular matrix in a first primitive streak mesendoderm cell culture medium; and
(ii) subsequently culturing the pluripotent stem cells from (i) on an extracellular matrix in a second primitive streak mesendoderm cell culture medium, wherein the first primitive streak mesendoderm cell culture medium comprises:
(a) activin; and
(b) Wnt-signaling activator;
and wherein the second primitive streak mesendoderm cell culture medium comprises:
(c) activin;
(d) Wnt-signaling activator; and
(e) fibroblast growth factor.

In some examples, in step (i) above, the pluripotent stem cells are cultured on an extracellular matrix in the first primitive streak mesendoderm cell culture medium for about 1 to 24 hours, or for about 6 to 24 hours, or for about 12 to 24 hours, or for about 18 to 24 hours, or for about 1 to 36 hours, or for about 1 to 48 hours, or for about 1, 3, 6, 9, 12, 15, 18, 24, 30, 36 or 48 hours. In one specific example, the pluripotent stem cells are cultured on an extracellular matrix in the first primitive streak mesendoderm cell culture medium for about 1 day.

In some examples, in step (i) above, the pluripotent stem cells to be cultured in the first primitive streak mesendoderm cell culture medium are at a confluency of between about 5% to about 80% confluent, or between about 10% to about 70% confluent, or between about 15% to about 60% confluent, or between about 20% to about 50% confluent, or between about 20% to about 40% confluent, or between about 20% to about 30% confluent, or of about 5%, 10%, 15%, 20%, 25%, 30%, 40%, 50%, 60%, 70% or 80% confluent. In some specific examples, the pluripotent stem cells to be cultured in the first primitive streak mesendoderm cell culture medium are at a confluency of between about 15% to about 30% confluent, or between about 20% to about 25% confluent, or of about 15%, 20%, 25% or 30% confluent. In one specific example, the pluripotent stem cells to be cultured in the first primitive streak mesendoderm cell culture medium are at a confluency of about 20%. Such a low confluency of pluripotent stem cells is used to ensure high efficiency of differentiation towards primitive streak or primitive streak-like mesendoderm cells.

The term "confluency" or its grammatical variant as used herein refers to an estimate of the number of adherent cells in a culture dish or a flask, referring to the proportion of the surface which is covered by cells. For example, a 50 percent confluency means that about half of the surface of the cell culture dish or flask is covered and there is still room for cells to grow. A 100 percent confluency means that the surface is completely covered by the cells, and no more room is left for the cells to grow as a monolayer. Many cell lines exhibit differences in growth rate or gene expression depending on the degree of confluency. Cells are typically passaged before becoming fully confluent in order to maintain their proliferation phenotype.

In some examples, in step (ii) above, the pluripotent stem cells are cultured on an extracellular matrix in the second primitive streak mesendoderm cell culture medium for about 1 to 24 hours, or for about 6 to 24 hours, or for about 12 to 24 hours, or for about 18 to 24 hours, or for about 1 to 36 hours, or for about 1 to 48 hours, or for about 1, 3, 6, 9, 12, 15, 18, 24, 30, 36 or 48 hours. In one specific example, the pluripotent stem cells are cultured on an extracellular matrix in the second primitive streak mesendoderm cell culture medium for about 1 day.

The term "activin" as used herein refers to a member of the TGF-β superfamily, which was discovered by virtue of its ability to stimulate the secretion of follicle-stimulating hormone (FSH). Activin exerts a broad range of effects on the differentiation, proliferation and functions of numerous cell types. Activin is a dimeric protein complex having two monomeric subunits linked to one another by a single disulfide bond. Examples of subunits include but are not limited to, activin $\beta_A$, activin $\beta_B$, activin $\beta_C$ and activin $\beta_E$. The common dimeric activin complexes, which can be used in the primitive streak mesendoderm cell culture medium, include but are not limited to: Activin A formed by two activin $\beta_A$ subunits, Activin B formed by two activin $\beta_B$ subunits, and Activin AB formed by one activin $\beta_A$ and one activin $\beta_B$ subunit. In one specific example, the activin used in the primitive streak mesendoderm cell culture medium is Activin A. In some examples, the activin in the primitive streak mesendoderm cell culture medium is at a concentration of between about 1 to about 250 ng/ml, or between about 5 to about 200 ng/ml, or between about 10 to about 150 ng/ml, or between about 15 to about 100 ng/ml, or between about 20 to about 90 ng/ml, or between about 25 to about 80 ng/ml, or between about 25 to about 70 ng/ml, or between about 25 to about 60 ng/ml, or between about 25 to about 50 ng/ml, or between about 25 to about 40 ng/ml, or between about 25 to about 30 ng/ml, or at about 1, 2, 3, 4, 5, 6, 7, 8, 9, 10, 12.5, 15, 17.5, 20, 22.5, 25, 27.5, 30, 40, 50, 60, 70, 80, 90, 100, 125, 150, 175, 200, 225, 250, 275 or 300 ng/ml. In some specific examples, the activin in the primitive streak mesendoderm cell culture medium is at a concentration of between about 1 to about 100 ng/ml. In one specific example, the activin in the primitive streak mesendoderm cell culture medium is at a concentration of about 25 ng/ml.

The term "Wnt-signaling activator" as used herein refers to a molecule or compound which activates or up-regulates genes involved in the Wnt-signaling pathways. The term "Wnt-signaling pathways" as used herein refers to a group of signal transduction pathways made of proteins that pass signals into a cell through cell surface receptors. Three Wnt-signaling pathways are currently known: the canonical Wnt pathway, the noncanonical planar cell polarity pathway, and the noncanonical Wnt/calcium pathway. All three pathways are activated by binding a Wnt-protein ligand to a Frizzled family receptor, which passes the biological signal to the Dishevelled protein inside the cell. The canonical Wnt pathway leads to regulation of gene transcription. The noncanonical planar cell polarity pathway regulates the cytoskeleton that is responsible for the shape of the cell. The noncanonical Wnt/calcium pathway regulates calcium inside the cell. Wnt signaling pathways use either nearby cell-cell communication (paracrine) or same-cell communication (autocrine). They are highly evolutionarily conserved in animals.

Wnt signaling was first identified for its role in carcinogenesis, then for its function in embryonic development. The embryonic processes it controls include body axis patterning, cell fate specification, cell proliferation and cell migration. These processes are necessary for proper formation of important tissues including bone, heart and muscle. Its role in embryonic development was discovered when genetic mutations in Wnt pathway proteins produced abnormal fruit fly embryos. Wnt signaling also controls tissue regeneration in adult bone marrow, skin and intestine.

Examples of Wnt-signaling activator include, but are not limited to, 2-Amino-4-[3,4-(methylenedioxy)benzylamino]-6-(3-methoxyphenyl)pyrimidine (CAS no. 853220-52-7), (1-(4-(Naphthalen-2-yl)pyrimidin-2-yl)piperidin-4-yl)methanamine (WAY 262611 or DKK1 inhibitor), WAY-316606 (5-(Phenylsulfonyl)-N-4-piperidinyl-2-(trifluoromethyl) benzene sulfonamide hydrochloride), heteroarylpyrimidines, arylpyrimidines, IQ1 (2-[2-(4-Acetylphenyl)diazenyl]-2-(3,4-dihydro-3,3-dimethyl-1(2H)-isoquinolinylidene)acetamide; CAS no. 331001-62-8), QS11 ((2S)-2-[2-(Indan-5-yloxy)-9-(1,1'-biphenyl-4-yl) methyl)-9H-purin-6-ylamino]-3-phenyl-propan-1-ol; CAS no. 944328-88-5), SB-216763 (3-(2,4-dichlorophenyl)-4-(1-methylindol-3-yl)pyrrole-2,5-dione), BIO(6-bromoindirubin-3'-oxime), deoxycholic acid (DCA), 2-amino-4-[3,4-(methylenedioxy)benzyl-amino]-6-(3-methoxyphenyl) pyrimidine, or derivatives thereof. In one example, the Wnt-signaling activator is a GS K3 inhibitor.

Examples of GSK3 inhibitor include, but are not limited to, CHIR-99021 6-[2-[[4-(2,4-dichlorophenyl)-5-(5-methyl-1H-imidazol-2-yl)pyrimidin-2-yl]amino]ethylamino]pyridine-3-carbonitrile, BIO 6-bromoindirubin-3 '-oxime, MeBIO (2'Z,3'E)-6-Bromo-1-methylindirubin-3'-oxime, AceBIO (2'Z,3'E)-6-Bromoindirubin-3'-acetoxime, SB 216763 3-(2,4-dichlorophenyl)-4-(1-methylindol-3-yl)pyrrole-2,5-dione, CHM-98014 6-N-[2-[[4-(2,4-dichlorophenyl)-5-imidazol-1-ylpyrimidin-2-yl]amino]ethyl]-3-nitropyridine-2,6-diamine, TWS 119 3-[[6-(3-aminophenyl)-7H-pyrrolo [2,3-d]pyrimidin-4-yl]oxy]phenol, IM-12 3-[2-(4-fluorophenyl)ethylamino]-1-methyl-4-(2-methyl-1H-indol-3-yl)pyrrole-2,5-dione, 1-Azakenpaullone 9-bromo-7,12-dihydropyrido [3',2':2,3]azepino [4,5-b]indol-6(5H)-one, AR-A014418 1-[(4-methoxyphenyl)methyl]-3-(5-nitro-1,3-thiazol-2-yl)urea, SB415286 3-(3-chloro-4-hydroxyanilino)-4-(2-nitrophenyl)pyrrole-2,5-dione, AZD1080 (3E)-3-[5-(morpholin-4-ylmethyl)-1H-pyridin-2-ylidene]-2-oxo-1H-indole-5-carbonitrile, AZD2858 3-amino-6-[4-(4-methylpiperazin-1-yl)sulfonylphenyl]-N-pyridin-3-ylpyrazine-2-carboxamide, Indirubin (3E)-3-(3-oxo-1H-indol-2-ylidene)-1H-indol-2-one and derivatives thereof. In one specific example, the GSK3 inhibitor is CHIR-99021 6-[2-[[4-(2,4-dichlorophenyl)-5-(5-methyl-1H-imidazol-2-yl)pyrimidin-2-yl]amino]ethylamino]pyridine-3-carbonitrile.

In some examples, the Wnt-signaling activator in the primitive streak mesendoderm cell culture medium is at a concentration of between about 0.5 to about 100 μM, or between about 1 to about 90 μM, or between about 1.5 to about 80 μM, or between about 2 to about 70 μM, or between about 2.5 to about 60 μM, or between about 3 to about 50 μM, or between about 3 to about 45 μM, or between about 3 to about 40 μM, or between about 3 to about 35 μM, or between about 3 to about 30 μM, or between about 3 to about 25 μM, or between about 3 to about 20 μM, or between about 3 to about 15 μM, or between about 3 to about 10 μM, or at about 0.5, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90 or 100 μM. In some specific examples, the Wnt-signaling activator in the primitive streak mesendoderm cell culture medium is at a concentration of between about 1 to about 20 μM. In one specific example, the Wnt-signaling activator in the primitive streak mesendoderm cell culture medium is at a concentration of about 3 μM.

The fibroblast growth factor (FGF) used in the primitive streak mesendoderm cell culture medium can be, for example, FGF1, FGF2, FGF3, FGF4, FGF5, FGF6, FGF7, FGF8, FGF9 and FGF10. In one specific example, the FGF is FGF2. In some examples, the FGF in the primitive streak mesendoderm cell culture medium is at a concentration of between about 0.5 to about 300 ng/ml, or between about 1 to about 250 ng/ml, or between about 2 to about 200 ng/ml, or between about 3 to about 150 ng/ml, or between about 4 to about 100 ng/ml, or between about 5 to about 90 ng/ml, or between about 6 to about 80 ng/ml, or between about 7 to about 70 ng/ml, or between about 8 to about 60 ng/ml, or between about 9 to about 50 ng/ml, or between about 10 to about 45 ng/ml, or between about 15 to about 40 ng/ml, or between about 20 to about 35 ng/ml, or between about 25 to about 30 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90, 100, 120, 140, 160, 180, 200, 250 or 300 ng/ml. In some specific examples, the FGF in the primitive streak mesendoderm cell culture medium is at a concentration of between about 1 to about 100 ng/ml. In one specific example, the FGF in the primitive streak mesendoderm cell culture medium is at a concentration of about 20 ng/ml.

In one example, culturing the pluripotent stem cells to obtain the primitive streak or primitive streak-like mesendoderm cells is carried out under a serum-free condition. In another example, the pluripotent stem cells are cultured without using any feeder cells.

In some examples, the pluripotent stem cells to be cultured in the first primitive streak mesendoderm cell culture medium are characterized by any one or more, or all of the following markers: OCT4, NANOG, SOX2, SSEA4, Tra-1-60, Tra-1-81 and Lin28.

The term "SSEA4", which is the short form of "Stage-specific embryonic antigen 4", is a glycoprotein expressed early in embryonic development and in pluripotent stem cells.

The term "Tra-1-60" as used herein refers to a cell surface antigen expressed in human embryonic stem cells and induced pluripotent stem cells. The term "Tra-1-81" as used herein refers to another cell surface antigen expressed in human embryonic stem cells and induced pluripotent stem cells. These surface antigens are down-regulated or even lost during the stem cell differentiation process.

Overall, a combination of the different stages of the method of the first aspect provides a step-wise, reproducible protocol of efficiently generating mature mesenchymal stem cells using chemically defined cell culture medium.

In a second aspect, there is provided a mesenchymal stem cell culture obtained by the method of the first aspect. In one example, there is also provided the mesenchymal stem cells obtained by the method of the first aspect.

Since the method of the first aspect uses a step-wise, well defined protocol which does not involve the use of serum and feeder cells, the mesenchymal stem cell culture obtained by the method of the first aspect has a higher purity of mesenchymal stem cells as compared to mesenchymal stem cell culture obtained from currently known methods. In some examples, the purity of the mature mesenchymal stem cells in the culture is at least 50%, or at least 60%, or at least 70%, or at least 80%, or at least 85%, or at least 90%, or at least 95%, or at least 97%, or at least 99%, or about 50%, about 55%, about 60%, about 65%, about 70%, about 75%, about 80%, about 83%, about 86%, about 89%, about 90%, about 92%, about 94%, about 96%, about 97%, about 98% or about 99%. Such a cell culture with a high purity of mesenchymal stem cells is clinically compliant and can be readily used in the treatment of a subject in need thereof. In some examples, a cell culture obtained using the method of the first aspect can be used for transplantation without the need of undergoing further processing, such as sorting or expansion of the mesenchymal stem cells in the cell culture.

Thus, in the third aspect, there is provided a method of treating cartilage or bone disease or injury in a patient, comprising transplanting a composition of cells comprising mature mesenchymal stem cells into the patient with cartilage defects, wherein the composition is obtained by the method of the first aspect.

In some examples, the mature mesenchymal stem cells to be transplanted into the patient are derived from the induced pluripotent stem cells obtained from the same patient, using the method as disclosed herein. This will reduce the risk of immune rejection.

As used herein, the terms "cartilage disease" and "cartilage injury" refer to disease or injury of the cartilage in a subject. Cartilage, by definition, is a resilient and smooth elastic tissue, rubber-like padding that covers and protects the ends of long bones at the joints, and is a structural component of the rib cage, the ear, the nose, the bronchial tubes, the intervertebral discs, and many other body components. It is not as hard and rigid as bone, but it is much stiffer and much less flexible than muscle. Cartilage is composed of specialized cells called chondrocytes that produce a large amount of collagenous extracellular matrix, abundant ground substance that is rich in proteoglycan and elastin fibers. Cartilage is classified in three types, elastic cartilage, hyaline cartilage and fibrocartilage, which differ in relative amounts of collagen and proteoglycan. As used herein, the terms "bone diseases" and "bone injury" refer to diseases and injury of the bones in a subject. A bone is a rigid organ that constitutes part of the vertebrate skeleton. Bones support and protect the various organs of the body, produce red and white blood cells, store minerals, provide structure and support for the body, and enable mobility. Bones come in a variety of shapes and sizes and have a complex internal and external structure. They are lightweight yet strong and hard, and serve multiple functions. Bone tissue is a hard tissue, a type of dense connective tissue. It has a honeycomb-like matrix internally, which helps to give the bone rigidity. Bone tissue is made up of different types of bone cells. Osteoblasts and osteocytes are involved in the formation and mineralization of bone, and osteoclasts are involved in the resorption of bone tissue. Modified (flattened) osteoblasts become the lining cells that form a protective layer on the bone surface. The mineralised matrix of bone tissue has an organic component of mainly collagen called ossein and an inorganic component of bone mineral made up of various salts. Bone tissue is a mineralized tissue of two types, cortical and cancellous bone. Other types of tissue found in bones include bone marrow, endosteum, periosteum, nerves, blood vessels and cartilage.

Examples of cartilage or bone diseases or injury include but are not limited to, osteoarthritis (OA), rheumatoid arthritis (RA), osteoporosis, osteogenesis imperfecta, osteochondroma, osteonecrosis and bone fracture.

The term "osteoarthritis" as used herein refers to a type of joint disease that results from breakdown of joint cartilage and underlying bone. The most common symptoms are joint pain and stiffness. Initially, symptoms may occur only following exercise, but over time may become constant. Other symptoms may include joint swelling, decreased range of motion, and weakness or numbness of the arms and legs. The most commonly involved joints are those near the ends of the fingers, at the base of the thumb, neck, lower back, knee, and hips. Joints on one side of the body are often more affected than those on the other. Causes of osteoarthritis include previous joint injury, abnormal joint or limb development, and inherited factors. Osteoarthritis is believed to be caused by mechanical stress on the joint and low grade inflammatory processes. It develops as cartilage is lost and the underlying bone becomes affected. As pain may make it difficult to exercise, muscle loss may occur. Diagnosis of osteoarthritis is typically based on signs and symptoms, with medical imaging and other tests occasionally used to either support or rule out other problems.

The term "rheumatoid arthritis" as used herein refers to a chronic systemic disease characterized by inflammatory changes occurring throughout the body's connective tissues. This form of arthritis strikes during the most productive years of adulthood, with onset in the majority of cases between the ages of 20 and 40. The disease affects men and women about equally in number, but three times as many women as men develop symptoms severe enough to require medical attention. The cause of rheumatoid arthritis is unknown and it is doubtful that there is one specific cause. It is regarded by some researchers as an autoimmune disease, in which the body produces abnormal antibodies against its own cells and tissues. Evidence to support this theory is found in the fact that there is an abnormally high level of certain types of immunoglobulins in the blood of patients suffering from rheumatoid arthritis. Other researchers contend that the disease may be due to infection, perhaps from an undefined virus or some other microorganism (e.g., *Mycoplasma*). There also is the possibility that rheumatoid arthritis is a genetic disorder in which one inherits a predisposition to the disease. Physical and emotional stresses also play some part in the onset of acute attacks. In about 75 percent of patients the onset of rheumatoid arthritis is gradual, with only mild symptoms at the beginning. Early symptoms include malaise, fever, weight loss, and morning stiffness of the joints. One or more joints may become swollen, painful, and inflamed. Some patients may experience only mild episodes of acute symptoms with lengthy remissions. The more typical patient, however, experiences increasingly severe and frequent attacks with subsequent joint damage and deformity. The pattern of remissions and exacerbations continues throughout the course of the disease. If untreated, and sometimes in spite of treatment, the joint pathology goes through four stages: (1) proliferative inflammation of the synovium with increased exudate, which eventually leads to thickening of the synovium; (2) formation of a layer of granulation tissue (pannus) that erodes and destroys the cartilage and eventually spreads to contiguous areas, causing destruction of the bone capsule and parts of the muscles that control the joint; (3) fibrous ankylosis resulting from invasion of the pannus by tough fibrous tissue; and (4) bony ankylosis as the fibrous tissue becomes calcified. In addition to the joint changes there is atrophy of muscles, bones, and skin adjacent to the affected joint. The most characteristic lesions of rheumatoid arthritis are subcutaneous nodules, which may be present for weeks or months and are most commonly found over bony prominences, especially near the elbow. Because rheumatoid arthritis is a systemic disease, there is involvement of connective tissues other than those in the musculoskeletal system. Degenerative lesions may be found in the collagen in the lungs, heart, blood vessels, and pleura.

The term "osteoporosis" as used herein refers to a disease where increased bone weakness increases the risk of a broken bone. It is the most common reason for a broken bone among the elderly. Bones that commonly break include the vertebrae in the spine, the bones of the forearm, and the hip. Until a broken bone occurs there are typically no symptoms. Bones may weaken to such a degree that a break may occur with minor stress or spontaneously. Chronic pain and a decreased ability to carry out normal activities may occur following a broken bone. Osteoporosis may be due to lower than normal bone mass and greater than normal bone loss. Bone loss increases after menopause due to lower levels of estrogen. Osteoporosis may also occur due to a number of diseases or treatments including alcoholism, anorexia, hyperthyroidism, kidney disease, and surgical removal of the ovaries. Certain medications increase the rate of bone loss including some antiseizure medications, chemotherapy, proton pump inhibitors, selective serotonin reuptake inhibitors, and glucocorticosteroids. Not enough exercise and smoking are also risk factors. Osteoporosis is defined as a bone density of 2.5 standard deviations below that of a young adult. This is typically measured by dual-energy X-ray absorptiometry at the hip.

The term "osteogenesis imperfecta" as used herein refers to a disease that is also known as brittle bone disease. It is caused by a group of genetic disorders that mainly affect the bones. It results in bones that break easily. The severity may be mild to severe. Other symptoms may include a blue tinge to the whites of the eye, short height, loose joints, hearing loss, breathing problems, and problems with the teeth. The underlying mechanism is usually a problem with connective tissue due to a lack of type I collagen. This occurs in more than 90% of cases due to mutations in the COL1A1 or COL1A2 gene. These genetic problems are often inherited from a person's parents in an autosomal dominant manner or occur via a new mutation. There are eight types of osteogenesis imperfect, with type I being the least severe and type II the most severe. Diagnosis is often based on symptoms and may be confirmed by collagen or DNA testing.

The term "osteochondroma" as used herein refers to a benign tumor of the bones. The tumor takes the form of cartilage-capped bony projections or outgrowth on the surface of bones (exostoses). It is characterized as a type of overgrowth that can occur in any bone where cartilage forms bone. Tumor most commonly affects long bones in the leg, pelvis, or scapula (shoulder blade). Development of osteochondromas takes place during skeletal growth between the ages of 13 and 15 and ceases when the growth plate fuses at puberty. They arise within the first three decades of life affecting children and adolescents. Osteochondromas occur in 3% of the general population and represent 35% of all benign tumors and 8% of all bone tumors. Majority of these tumors are solitary non-hereditary lesions and approximately 15% of osteochondromas occur as hereditary multiple osteochondromas (HMOs). They can occur as a solitary lesion (solitary osteochondroma) or multiple lesions within the context of the same bone (Multiple Osteochondroma). Osteochondromas do not result from injury and the exact cause remains unknown. Recent research has indicated that multiple osteochondromas is an autosomal dominant inherited disease. Germ line Mutations in EXT1 and EXT2 genes located on chromosomes 8 and 11 have been associated with the cause of the disease. The treatment choice for osteochondroma is surgical removal of solitary lesion or partial excision of the outgrowth, when symptoms cause motion limitations or nerve and blood vessel impingements.

The term "osteonecrosis" as used herein refers to a disease caused by reduced blood flow to bones in the joints. With too little blood, the bone starts to die and may break down. Osteonecrosis is also known as avascular necrosis, aseptic necrosis or ischemic necrosis. Osteonecrosis is most often found in the hips, knees, shoulders, and ankles. In people with healthy bones, new bone is always replacing old bone. This process keeps bones strong and also happens when children grow or if a bone is injured. In osteonecrosis, bone breaks down faster than the body can make enough strong, new bone. If not treated, the disease worsens and the bones in the joints break down. The patient may not be able to bend or move the affected joint very well, and may have pain in the joint.

The term "bone fracture" as used herein refers to a medical condition in which there is damage in the continuity of the bone. A bone fracture may be the result of high force impact or stress, or a minimal trauma injury as a result of certain medical conditions that weaken the bones, such as osteoporosis, bone cancer, or osteogenesis imperfecta, where the fracture is then properly termed a pathologic fracture.

When a composition of cells comprising mature mesenchymal stem cells is transplanted into a subject to treat cartilage or bone disease or injury in the subject, the composition should have a high percentage of mature mesenchymal stem cells to ensure the proper differentiation of the mature mesenchymal stem cells into the desired mesenchymal tissue such as cartilage and bone. Thus, in some examples, the composition comprises at least 80%, or at least 85%, or at least 90%, or at least 95%, or at least 97%, or at least 99%, or about 80%, about 83%, about 86%, about 89%, about 90%, about 92%, about 94%, about 96%, about 97%, about 98% or about 99% of mature mesenchymal stem cells. Such compositions comprising high percentage of mature mesenchymal stem cells can be obtained directly using the method of the first aspect.

The present disclosure also provided a culture medium for deriving primitive streak mesendoderm cells or primitive streak-like mesendoderm cells from pluripotent stem cells. Thus, in the fourth aspect, there is provided a culture medium for deriving primitive streak mesendoderm cells or primitive streak-like mesendoderm cells from pluripotent stem cells, comprising: (a) activin; (b) WNT-signaling activator; and (c) fibroblast growth factor.

The activin, WNT-signaling activator and fibroblast growth factor used in the culture medium of the fourth aspect are as defined above.

In one example, the culture medium of the fourth aspect comprises activin A, WNT-signaling activator as described herein and fibroblast growth factor as described herein. In another example, the culture medium of the fourth aspect comprises activin as described herein, CHIR-99021 6-[2-[[4-(2,4-dichlorophenyl)-5-(5-methyl-1H-imidazol-2-yl)pyrimidin-2-yl]amino]ethylamino]pyridine-3-carbonitrile and fibroblast growth factor as described herein. In yet another example, the culture medium of the fourth aspect comprises activin as described herein, WNT-signaling activator as described herein and FGF2. In yet another example, the culture medium of the fourth aspect comprises activin A, CHIR-99021 6-[2-[[4-(2,4-dichlorophenyl)-5-(5-methyl-1H-imidazol-2-yl)pyrimidin-2-yl]amino]ethylamino]pyridine-3-carbonitrile and fibroblast growth factor as described herein.

In yet another example, the culture medium of the fourth aspect comprises activin as described herein, CHIR-99021 6-[2-[[4-(2,4-dichlorophenyl)-5-(5-methyl-1H-imidazol-2-yl)pyrimidin-2-yl]amino]ethylamino]pyridine-3-carbonitrile and FGF2. In yet another example, the culture medium of the fourth aspect comprises activin A, WNT-signaling activator as described herein and FGF2. In a further example, the culture medium of the fourth aspect comprises activin A, CHIR-99021 6-[2-[[4-(2,4-dichlorophenyl)-5-(5-methyl-1H-imidazol-2-yl)pyrimidin-2-yl]amino]ethylamino]pyridine-3-carbonitrile and FGF2. The culture medium of the fourth aspect can be used in all the method as described and/or claimed herein.

In some examples, the activin in the culture medium of the fourth aspect is at a concentration of between about 1 to about 250 ng/ml, or between about 5 to about 200 ng/ml, or between about 10 to about 150 ng/ml, or between about 15 to about 100 ng/ml, or between about 20 to about 90 ng/ml, or between about 25 to about 80 ng/ml, or between about 25 to about 70 ng/ml, or between about 25 to about 60 ng/ml, or between about 25 to about 50 ng/ml, or between about 25 to about 40 ng/ml, or between about 25 to about 30 ng/ml, or at about 1, 2, 3, 4, 5, 6, 7, 8, 9, 10, 12.5, 15, 17.5, 20, 22.5, 25, 27.5, 30, 40, 50, 60, 70, 80, 90, 100, 125, 150, 175, 200, 225, 250, 275 or 300 ng/ml. In some specific examples, the activin in the culture medium of the fourth aspect is at a concentration of between about 1 to about 100 ng/ml. In one specific example, the activin in the culture medium of the fourth aspect is at a concentration of about 25 ng/ml.

In some examples, the Wnt-signaling activator in the culture medium of the fourth aspect is at a concentration of between about 0.5 to about 100 µM, or between about 1 to about 90 µM, or between about 1.5 to about 80 µM, or between about 2 to about 70 µM, or between about 2.5 to about 60 µM, or between about 3 to about 50 µM, or between about 3 to about 45 µM, or between about 3 to about 40 µM, or between about 3 to about 35 µM, or between about 3 to about 30 µM, or between about 3 to about 25 µM, or between about 3 to about 20 µM, or between about 3 to about 15 µM, or between about 3 to about 10 µM, or at about 0.5, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90 or 100 µM. In some specific examples, the Wnt-signaling activator in the culture medium of the fourth aspect is at a concentration of between about 1 to about 20 µM. In one specific example, the Wnt-signaling activator in the culture medium of the fourth aspect is at a concentration of about 3 µM.

In some examples, the FGF in the culture medium of the fourth aspect is at a concentration of between about 0.5 to about 300 ng/ml, or between about 1 to about 250 ng/ml, or between about 2 to about 200 ng/ml, or between about 3 to about 150 ng/ml, or between about 4 to about 100 ng/ml, or between about 5 to about 90 ng/ml, or between about 6 to about 80 ng/ml, or between about 7 to about 70 ng/ml, or between about 8 to about 60 ng/ml, or between about 9 to about 50 ng/ml, or between about 10 to about 45 ng/ml, or between about 15 to about 40 ng/ml, or between about 20 to about 35 ng/ml, or between about 25 to about 30 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90, 100, 120, 140, 160, 180, 200, 250 or 300 ng/ml. In some specific examples, the FGF in the culture medium of the fourth aspect is at a concentration of between about 1 to about 100 ng/ml. In one specific example, the FGF in the culture medium of the fourth aspect is at a concentration of about 20 ng/ml.

In the fifth aspect, there is provided a culture medium for deriving lateral plate mesoderm cells from primitive streak mesendoderm cells or deriving lateral plate-like mesoderm cells from primitive streak-like mesendoderm cells, comprising: (1) fibroblast growth factor; (2) bone morphogenetic protein; (3) follistatin; and (4) optionally Rho-associated protein kinase (ROCK) inhibitor.

The fibroblast growth factor, bone morphogenetic protein, follistatin and ROCK inhibitor used in the culture medium of the fifth aspect are as defined above.

In one example, the culture medium of the fifth aspect comprises FGF2, bone morphogenetic protein as described herein, follistatin and optionally Rho-associated protein kinase (ROCK) inhibitor as described herein. In another example, the culture medium of the fifth aspect comprises fibroblast growth factor as described herein, BMP4, follistatin and optionally Rho-associated protein kinase (ROCK) inhibitor as described herein. In yet another example, the culture medium of the fifth aspect comprises fibroblast growth factor as described herein, bone morphogenetic protein as described herein, follistatin and optionally Y27632 (R)-(+)-trans-4-(1-Aminoethyl)-N-(4-Pyridyl)cyclohexanecarboxamide dihydrochloride as described herein. In yet another example, the culture medium of the fifth aspect comprises FGF2, BMP4, follistatin and optionally Rho-associated protein kinase (ROCK) inhibitor as described herein. In yet another example, the culture medium of the fifth aspect comprises fibroblast growth factor as described herein, BMP4, follistatin and optionally Y27632 (R)-(+)-trans-4-(1-Aminoethyl)-N-(4-Pyridyl)cyclohexanecarboxamide dihydrochloride as described herein. In yet another example, the culture medium of the fifth aspect comprises FGF2, bone morphogenetic protein as described herein, follistatin and optionally Y27632 (R)-(+)-trans-4-(1-Aminoethyl)-N-(4-Pyridyl)cyclohexanecarboxamide dihydrochloride as described herein. In yet another example, the culture medium of the fifth aspect comprises FGF2, BMP4, follistatin and optionally Y27632 (R)-(+)-trans-4-(1-Aminoethyl)-N-(4-Pyridyl)cyclohexanecarboxamide dihydrochloride. The culture medium of the fifth aspect can be used in all the method as described and/or claimed herein.

In some examples, the fibroblast growth factor in the culture medium of the fifth aspect is at a concentration of between about 0.5 to about 100 ng/ml, or between about 1 to about 90 ng/ml, or between about 2 to about 80 ng/ml, or between about 3 to about 70 ng/ml, or between about 4 to about 60 ng/ml, or between about 5 to about 50 ng/ml, or between about 6 to about 45 ng/ml, or between about 7 to about 40 ng/ml, or between about 8 to about 35 ng/ml, or between about 9 to about 30 ng/ml, or between about 10 to about 25 ng/ml, or between about 15 to about 20 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 ng/ml. In some specific examples, the FGF in the culture medium of the fifth aspect is at a concentration of between about 1 to about 100 ng/ml. In one specific example, the fibroblast growth factor in the culture medium of the fifth aspect is at a concentration of 20 ng/ml.

In some examples, the bone morphogenetic protein in the culture medium of the fifth aspect is at a concentration of between about 1 to about 200 ng/ml, or between about 5 to about 180 ng/ml, or between about 10 to about 160 ng/ml, or between about 15 to about 140 ng/ml, or between about 20 to about 120 ng/ml, or between about 25 to about 100 ng/ml, or between about 30 to about 90 ng/ml, or between about 35 to about 80 ng/ml, or between about 40 to about 70 ng/ml, or between about 40 to about 60 ng/ml, or between about 40 to about 55 ng/ml, or between about 40 to about 50 ng/ml, or between about 40 to about 45 ng/ml, or at about 1, 2, 3, 4, 5, 6, 7, 8, 9, 10, 12.5, 15, 17.5, 20, 22.5, 25, 27.5, 30, 35, 40, 45, 50, 55, 60, 65, 70, 75, 80, 85, 90, 95, 100, 110, 120, 130, 140, 150, 160, 170, 180, 190 or 200 ng/ml. In some specific examples, the BMP in the culture medium of the fifth aspect is at a concentration of between about 1 to about 80 ng/ml. In one specific example, the bone morphogenetic protein in the culture medium of the fifth aspect is at a concentration of 40 ng/ml.

In some examples, the ROCK inhibitor in the culture medium of the fifth aspect is at a concentration of between about 1 to about 100 µM, or between about 1.5 to about 90 µM, or between about 2 to about 80 µM, or between about 2.5 to about 70 µM, or between about 3 to about 60 µM, or between about 3.5 to about 50 µM, or between about 4 to about 40 µM, or between about 4.5 to about 30 µM, or between about 5 to about 2504, or between about 5 to about 20 µM, or between about 5 to about 1504, or between about 5 to about 10 µM, or at about 1, 2, 3, 4, 5, 6, 7, 8, 9, 10, 12.5, 15, 17.5, 20, 22.5, 25, 27.5, 30, 35, 40, 45, 50, 55, 60, 65, 70, 75, 80, 85, 90, 95 or 100 µM. In one specific example, the ROCK inhibitor in the culture medium of the fifth aspect is at a concentration of 504.

In some examples, the follistatin in the culture medium of the fifth aspect is at a concentration of between about 1 ng/ml to about 600 ng/ml, between about 5 ng/ml to about 550 ng/ml, between about 10 ng/ml to about 500 ng/ml, between about 20 to about 450 ng/ml, or between about 30 to about 400 ng/ml, or between about 40 to about 350 ng/ml, or between about 50 to about 300 ng/ml, or between about 60 to about 250 ng/ml, or between about 70 to about 200 ng/ml, or between about 80 to about 180 ng/ml, or between about 90 to about 160 ng/ml, or between about 100 to about 140 ng/ml, or between about 100 to about 120 ng/ml, or at about 1, 2.5, 5, 7.5, 10, 20, 30, 40, 50, 60, 70, 80, 90, 100, 110, 120, 130, 140, 150, 160, 170, 180, 190, 200, 220, 240, 260, 280, 300, 350, 400, 450, 500, 550 or 600 ng/ml. In one specific example, the follistatin in the culture medium of the fifth aspect is at a concentration of 100 ng/ml.

In the sixth aspect, there is provided a culture medium for deriving and maintaining mature mesenchymal stem cells from lateral plate mesoderm cells or lateral plate-like mesoderm cells, comprising: (i) fibroblast growth factor; (ii) platelet-derived growth factor (PDGF); (iii) epidermal growth factor (EGF) family protein; and (iv) ascorbic acid.

The culture medium of the sixth aspect may further comprise transforming growth factor beta (TGF-β).

The fibroblast growth factor, PDGF, EGF family protein, ascorbic acid and TGF-β used in the culture medium of the sixth aspect are as defined above.

In one example, the culture medium of the sixth aspect comprises FGF2, PDGF as described herein, EGF family protein as described herein and ascorbic acid. In another example, the culture medium of the sixth aspect comprises fibroblast growth factor as described herein, PDGFAB, EGF family protein as described herein and ascorbic acid. In yet another example, the culture medium of the sixth aspect comprises fibroblast growth factor as described herein, PDGF as described herein, EGF and ascorbic acid. In yet another example, the culture medium of the sixth aspect comprises FGF2, PDGFAB, EGF family protein as described herein and ascorbic acid. In yet another example, the culture medium of the sixth aspect comprises fibroblast growth factor as described herein, PDGFAB, EGF and ascorbic acid. In yet another example, the culture medium of the sixth aspect comprises FGF2, PDGF as described herein, EGF and ascorbic acid. In yet another example, the culture medium of the sixth aspect comprises FGF2, PDGFAB, EGF and ascorbic acid.

In one example, the culture medium of the sixth aspect comprises FGF2, PDGF as described herein, EGF family protein as described herein, ascorbic acid and TGF-β as described herein. In another example, the culture medium of the sixth aspect comprises fibroblast growth factor as described herein, PDGFAB, EGF family protein as described herein, ascorbic acid and TGF-β as described herein. In yet another example, the culture medium of the sixth aspect comprises fibroblast growth factor as described herein, PDGF as described herein, EGF, ascorbic acid and TGF-β as described herein. In yet another example, the culture medium of the sixth aspect comprises fibroblast growth factor as described herein, PDGF as described herein, EGF family protein as described herein, ascorbic acid and TGF-µ1. In yet another example, the culture medium of the sixth aspect comprises FGF2, PDGFAB, EGF family protein as described herein, ascorbic acid and TGF-β as described herein. In yet another example, the culture medium of the sixth aspect comprises FGF2, PDGF as described herein, EGF, ascorbic acid and TGF-β as described herein. In yet another example, the culture medium of the sixth aspect comprises FGF2, PDGF as described herein, EGF family protein as described herein, ascorbic acid and TGF-β1. In yet another example, the culture medium of the sixth aspect comprises fibroblast growth factor as described herein, PDGFAB, EGF, ascorbic acid and TGF-β as described herein. In yet another example, the culture medium of the sixth aspect comprises fibroblast growth factor as described herein, PDGFAB, EGF family protein as described herein, ascorbic acid and TGF-β1. In yet another example, the culture medium of the sixth aspect comprises fibroblast growth factor as described herein, PDGF as described herein, EGF, ascorbic acid and TGF-β1. In yet another example, the culture medium of the sixth aspect comprises FGF2, PDGFAB, EGF, ascorbic acid and TGF-β as described herein. In yet another example, the culture medium of the sixth aspect comprises FGF2, PDGFAB, EGF family protein as described herein, ascorbic acid and TGF-β1. In yet another example, the culture medium of the sixth aspect comprises FGF2, PDGF as described herein, EGF, ascorbic acid and TGF-β1. In yet another example, the culture medium of the sixth aspect comprises fibroblast growth factor as described herein, PDGFAB, EGF, ascorbic acid and TGF-β1. In yet another example, the culture medium of the sixth aspect comprises FGF2, PDGFAB, EGF, ascorbic acid and TGF-β1. The culture medium of the sixth aspect can be used in all the method as described and/or claimed herein.

In some examples, the fibroblast growth factor used in the culture medium of the sixth aspect is at a concentration of between about 0.5 to about 100 ng/ml, or between about 1 to about 90 ng/ml, or between about 1.5 to about 80 ng/ml, or between about 2 to about 70 ng/ml, or between about 2.5 to about 60 ng/ml, or between about 3 to about 50 ng/ml, or between about 3.5 to about 45 ng/ml, or between about 4 to about 40 ng/ml, or between about 4.5 to about 35 ng/ml, or between about 5 to about 30 ng/ml, or between about 5 to about 25 ng/ml, or between about 5 to about 20 ng/ml, or between about 5 to about 15 ng/ml, or between about 5 to about 10 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 ng/ml. In some specific examples, the fibroblast growth factor in the culture medium of the sixth aspect is at a concentration of between about 1 to about 100 ng/ml. In one specific example, the fibroblast growth factor in the culture medium of the sixth aspect is at a concentration of 5 ng/ml. In another specific example, the fibroblast growth factor in the culture medium of the sixth aspect is at a concentration of 10 ng/ml.

In some examples, the PDGF used in the culture medium of the sixth aspect is at a concentration of between about 0.5 to about 100 ng/ml, or between about 1 to about 90 ng/ml, or between about 1.5 to about 80 ng/ml, or between about 2 to about 70 ng/ml, or between about 2.5 to about 60 ng/ml, or between about 3 to about 50 ng/ml, or between about 3.5 to about 45 ng/ml, or between about 4 to about 40 ng/ml, or between about 4.5 to about 35 ng/ml, or between about 5 to about 30 ng/ml, or between about 5 to about 25 ng/ml, or between about 5 to about 20 ng/ml, or between about 5 to about 15 ng/ml, or between about 5 to about 10 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 ng/ml. In some specific examples, the PDGF in the culture medium of the sixth aspect is at a concentration of between about 1 to about 50 ng/ml.

In one specific example, the PDGF in the culture medium of the sixth aspect is at a concentration of 5 ng/ml.

In some examples, the EGF family protein used in the culture medium of the sixth aspect is at a concentration of between about 0.5 to about 100 ng/ml, or between about 1 to about 90 ng/ml, or between about 1.5 to about 80 ng/ml, or between about 2 to about 70 ng/ml, or between about 2.5 to about 60 ng/ml, or between about 3 to about 50 ng/ml, or between about 3.5 to about 45 ng/ml, or between about 4 to about 40 ng/ml, or between about 4.5 to about 35 ng/ml, or between about 5 to about 30 ng/ml, or between about 7.5 to about 25 ng/ml, or between about 10 to about 20 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 ng/ml. In one specific example, the EGF family protein used in the culture medium of the sixth aspect is at a concentration of 10 ng/ml.

In some examples, the ascorbic acid used in the culture medium of the sixth aspect is at a concentration of between about 1 to about 500 µg/ml, or between about 5 to about 450 µg/ml, or between about 10 to about 400 µg/ml, or between about 20 to about 350 µg/ml, or between about 25 to about 300 µg/ml, or between about 30 to about 250 µg/ml, or between about 35 to about 200 µg/ml, or between about 40 to about 180 µg/ml, or between about 45 to about 160 µg/ml, or between about 50 to about 140 µg/ml, or between about 50 to about 120 µg/ml, or between about 50 to about 110 µg/ml, or between about 50 to about 100 µg/ml, or between about 50 to about 90 µg/ml, or between about 50 to about 80 µg/ml, or between about 50 to about 70 µg/ml, or between about 50 to about 60 µg/ml, or at about 1, 5, 10, 15, 20, 25, 30, 35, 40, 45, 50, 60, 70, 80, 90, 100, 150, 200, 250, 300, 350, 400, 450 or 500 µg/ml. In some specific examples, the ascorbic acid in the culture medium of the sixth aspect is at a concentration of between about 5 to about 100 µg/ml. In one specific example, the ascorbic acid in the culture medium of the sixth aspect is at a concentration of 50 µg/ml.

In some examples, the TGF-β used in the culture medium of the sixth aspect is at a concentration of between about 1 ng/ml to about 100 µg/ml, or between about 5 ng/ml to about 90 µg/ml, or between about 10 ng/ml to about 80 µg/ml, or between about 15 ng/ml to about 70 µg/ml, or between about 20 ng/ml to about 60 µg/ml, or between about 30 ng/ml to about 50 µg/ml, or between about 40 ng/ml to about 45 µg/ml, or between about 50 ng/ml to about 40 µg/ml, or between about 60 ng/ml to about 35 µg/ml, or between about 70 ng/ml to about 30 µg/ml, or between about 80 ng/ml to about 25 µg/ml, or between about 90 ng/ml to about 20 µg/ml, or between about 100 ng/ml to about 15 µg/ml, or between about 150 ng/ml to about 10 µg/ml, or between about 200 ng/ml to about 5 µg/ml, or between about 300 ng/ml to about 2 µg/ml, or between about 400 ng/ml to about 1 µg/ml, or between about 500 ng/ml to about 900 ng/ml, or between about 600 ng/ml to about 800 ng/ml, or at about 0.5, 1, 2, 3, 4, 5, 6, 7, 8, 9, 10, 12, 14, 16, 18, 20, 25, 30, 40 or 50 ng/ml, or at about 1, 2, 3, 4, 5, 6, 7, 8, 9, 10, 12.5, 15, 17.5, 20, 22.5, 25, 27.5, 30, 35, 40, 45, 50, 60, 70, 80, 90 or 100 µg/ml. In some examples, the TGF-β used in the culture medium of the sixth aspect is at a concentration of between about 1 to about 20 ng/ml. In one specific example, the TGF-β used in the culture medium of the sixth aspect is at a concentration of 10 ng/ml.

Any cell culture medium may also be supplemented with further components, as and when required based on the experiment to be performed, the cell type in questions, as well as the required status of the cell (starved or otherwise). Cell culture supplements are, but are not limited to, amino acids, chemical compounds, salts, buffering salts or agents, antibiotics, antimycotics, cytokines, growth factors, hormones, lipids, and derivatives thereof.

In one example, the amino acid is, but is not limited to, isoleucine, leucine, lysine, methionine, phenylalanine, threonine, tryptophan, valine, arginine, cysteine, cystine, histidine, tyrosine, alanine, aspartic acid, asparagine, glutamine, glutamic acid, glycine, hydroxproline, proline, serine, combinations and derivatives thereof. In one example, the amino acid is glutamine. The amino acids listed herein may be provided in either the L- or the D-stereoisomer, as required. In one example, the glutamine supplement is L-alanyl-L-glutamine dipeptide.

In one example, the antimycotic is, but is not limited to, amphotericin B, clotimazol, nystatin and combinations thereof.

In a further example, the antibiotic is, but is not limited to, ampicillin, penicillin, chloramphenicol, gentamycin, kanamycin, neomycin, streptomycin, tetracycline, polymyxin B, actinomycin, bleomycin, cyclohexamide, geneticin (G148), hygromycin B, mitomycin C and combinations thereof. In one example, the antibiotic is penicillin. In another example, the antibiotic is streptomycin. In yet another example, the antibiotic is penicillin and streptomycin. In one example, the antibiotic is gentamicin.

In one example, the salt, buffering salt or agent is, but is not limited to, sodium chloride (NaCl), potassium chloride (KCl), sodium hydrogen phosphate ($Na_2HPO_4$), monosodium phosphate ($NaH_2PO_4$), monopotassium phosphate ($KH_2PO_4$), magnesium sulfate ($MgSO_4$), calcium chloride (CaCl$_2$), calcium chloride (CaCl$_2$×2 H$_2$O), dextrose, glucose, Sodium bicarbonate (NaHCO$_3$) and combinations thereof.

In another example, the supplement for cell proliferation is heparin.

In one example, the growth supplement is insulin.

In another example, the growth enhancer of stem cells is laminin.

In some examples, the culture medium as disclosed herein further comprises a basal cell growth medium at a percentage of about 40% to about 50%, a nutrient mixture at a percentage of about 40% to about 50%, a mixture of insulin, transferrin and sodium selenite at a percentage of about 0.5% to 3% or at about 1%, a cell growth a viability supplement at a percentage of about 0.5% to about 5% or at about 2%, a glutamine supplement at a concentration of about 0.5 to about 5 mM or at about 2 mM, a reducing agent at a concentration of about 50 to about 200 µM or at about 90 µM.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

The following examples illustrate methods by which aspects of the invention may be practiced or materials suitable for practice of certain embodiments of the invention may be prepared.

Examples 1—Generation of Induced Pluripotent Stem Cells

Human induced pluripotent stem cells (iPSCs) were generated by infecting fibroblasts of MRCS or BJ cells with four retroviruses encoding human Oct4, Sox2, KLF4 and c-Myc. GP2 cells were transfected with four factors and virus was harvested forty-eight hour post-transduction. Fibroblasts were infected with harvested virus. Five days after infection, infected MRCS cells were plated onto mouse embryonic fibroblast feeder cells treated with mitomycin C and cultured in human ES medium to generate iPSCs.

Figure 9:
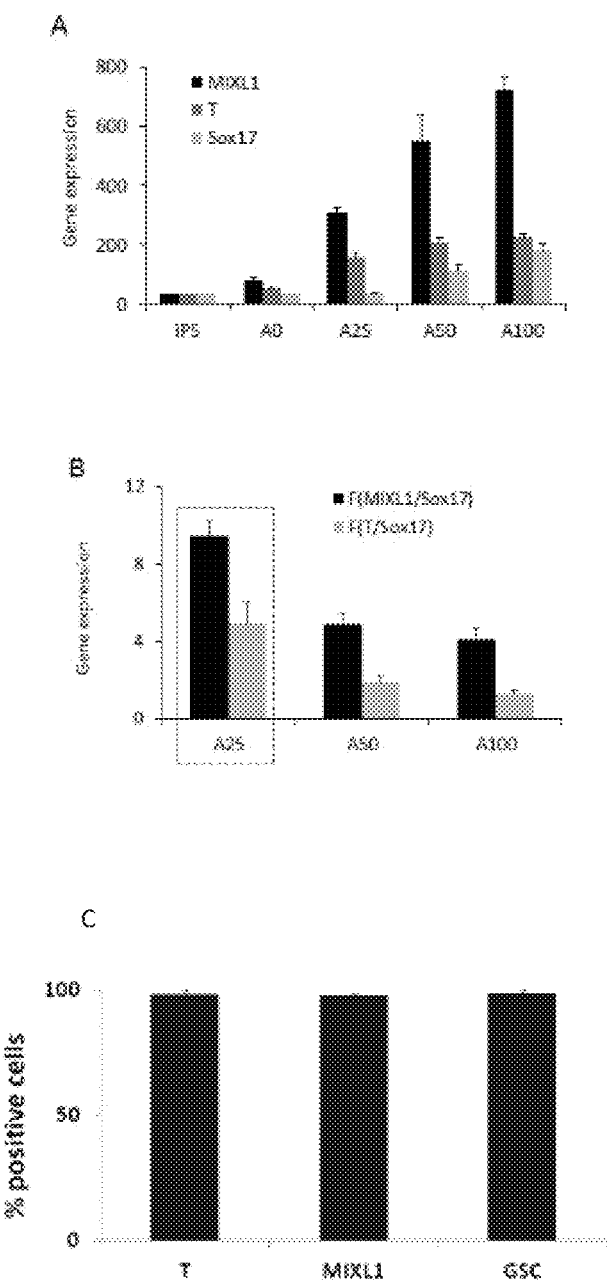
FIG. 9 shows the differentiation of human induced pluripotent stem cells (iPSCs) towards primitive streak (PS)-like mesendoderm cells.
Figure 9:
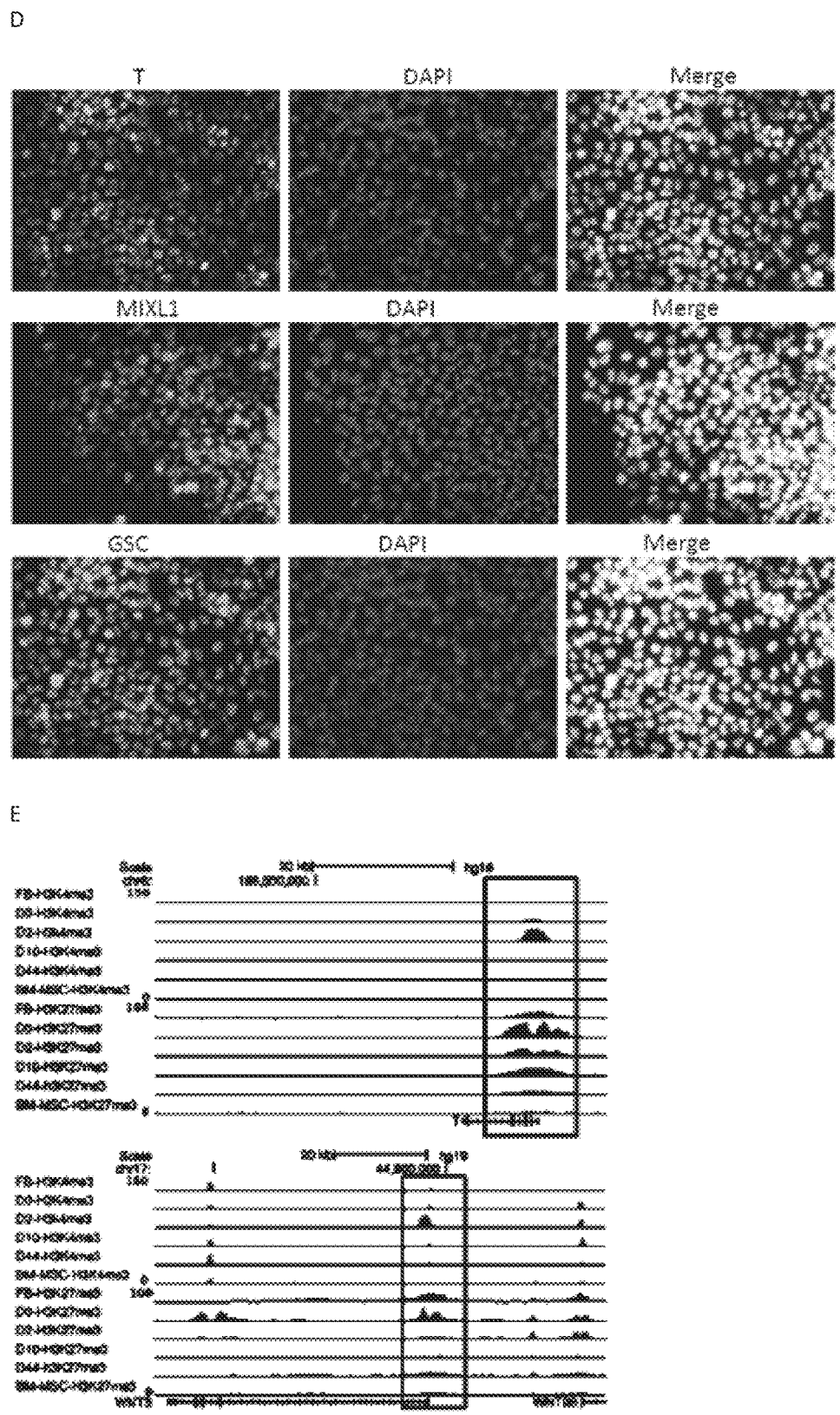
Figure 16:
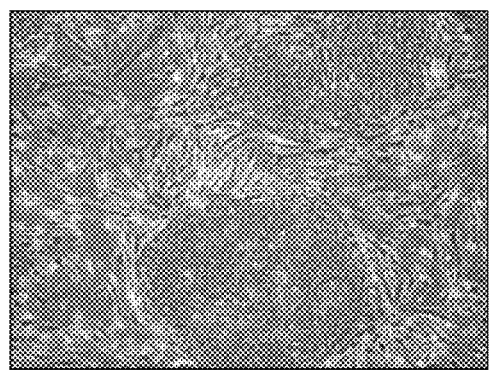
FIG. 16 shows the generation of iPSCs from human fibroblasts.
Figure 16:
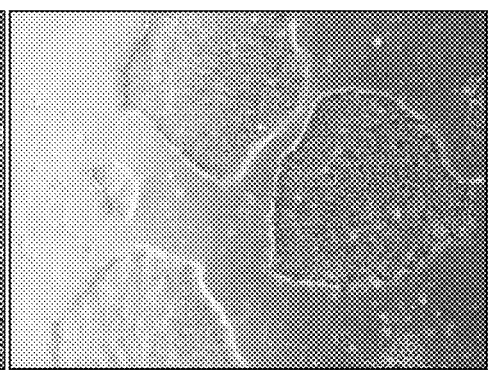
Figure 16:
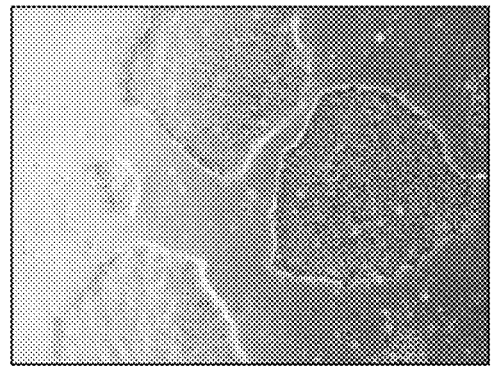
Figure 16:
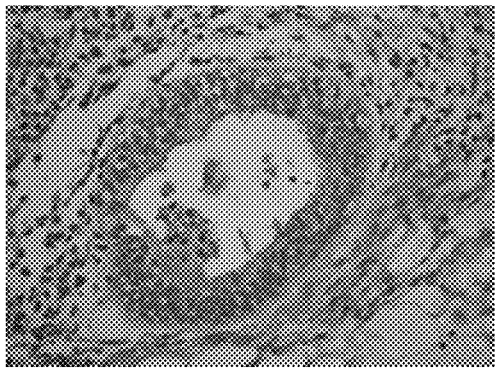
Figure 16:
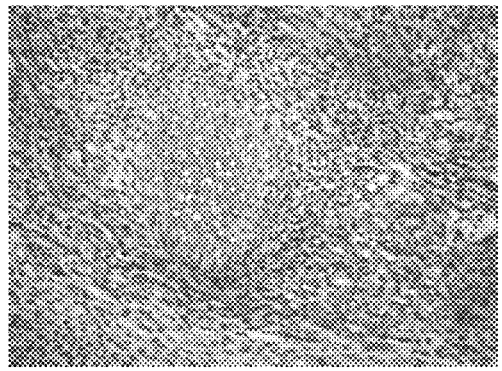
Figure 16:
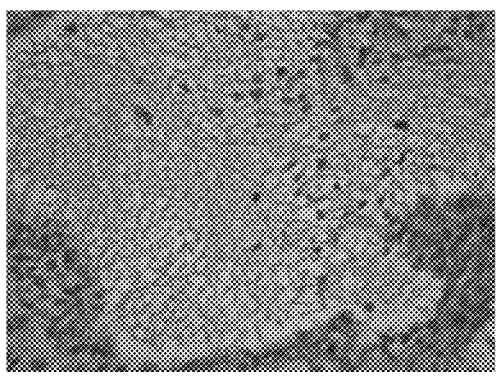
Figure 16:
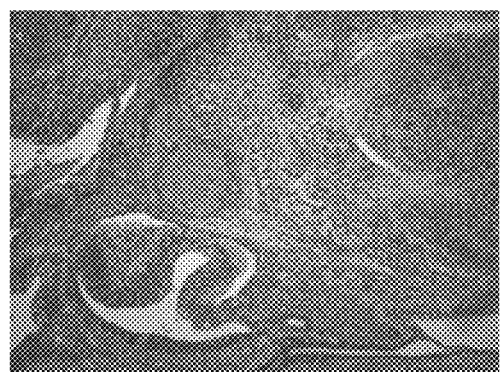
Figure 16:
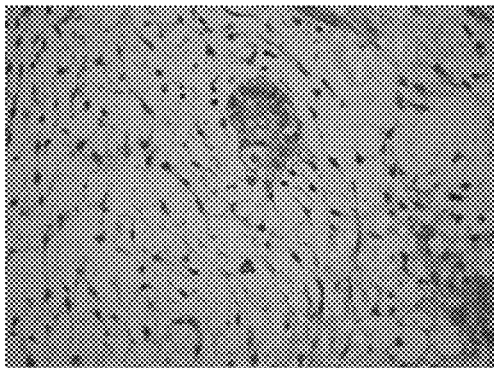
Figure 16:
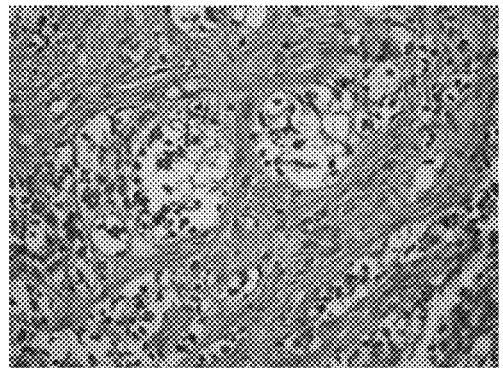

The iPSC colonies displayed typical ES-like morphology on the feeder (FIG. 16A) or feeder-free culture (FIG. 16B). Similar to hES cells, the colonies of iPSCs were AP positive (FIG. 16C), which were different from fibroblasts negative for AP stain. Immunostaining showed that iPSCs were positive for hES markers including Oct4, Nanog, Sox2, SSEA4, Tra-1-80 and Lin28 by immunocytochemistry staining (FIG. 9D). The generated iPSCs formed teratomas containing all three germ layers of tissues after subcutaneous injection into nude mice, including gut-like epithelial tissues (endoderm), cartilage (mesoderm), adipose tissue (mesoderm) and neural tissue (ectoderm) (FIG. 16C). These data showed that iPSCs from somatic cells were similar to human ES cells.

Example 2—Differentiation of Human Embryonic Stem Cells (hESC) or iPSCs and into Primitive Streak or Primitive Streak-Like Mesendoderm Cells iPSCs from MRCS or BJ cell lines, or hESCs were differentiated into primitive streak-like mesendoderm cells and primitive streak mesendoderm cells respectively. Feeder-free iPSCs were maintained in mTeSR (Stem Cell Technologies) before differentiation. To differentiate iPSCs, iPSCs were digested with 1 mg/ml collagenase IV for 5-10 min at 37° C. into small clumps and placed on a fibronectin (FN, 10 µg/ml)-coated surface in medium containing activin A (25 ng/ml) and CHIR99021 (3 µM) for 1 day in a basal medium (DMEM: F12, 1% ITS, 2% B27, 2 mM L-Glutamine, 90 uM ß-mercaptoethanol), followed by Activin A (25 ng/ml), CHIR99021 (3 µM) and FGF (20 ng/ml) for subsequent 24 hours to differentiate toward primitive streak (PS)-like mesendoderm.

Figure 8:
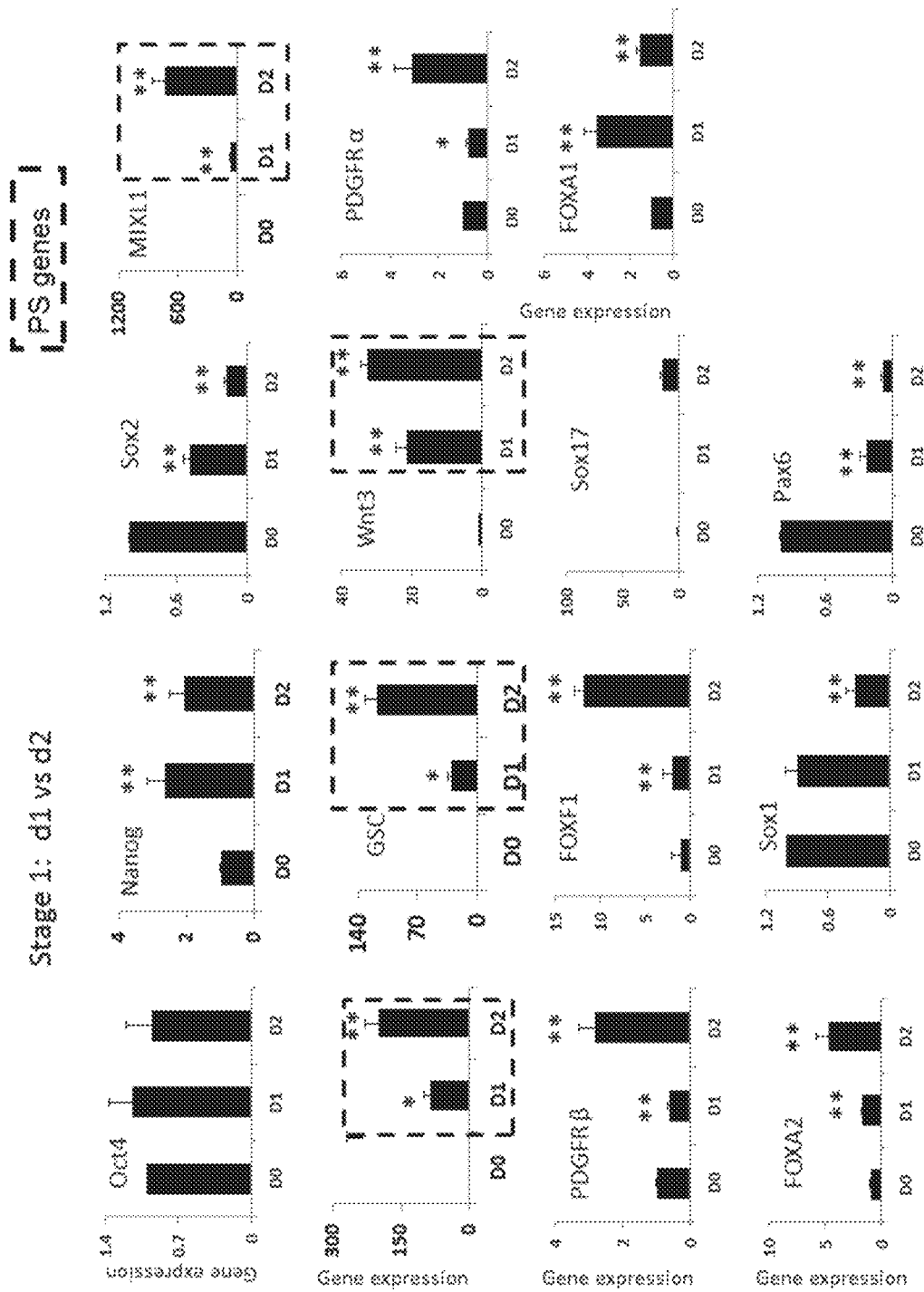
FIG. 8 shows that as compared to day 1, day 2 cells express significantly higher primitive streak/mesendoderm genes (MIXL1, T, GSC and Wnt3) under combination of Activin A, CHIR99021 and FGF for 2 days compared to other conditions, as measured by qPCR. Therefore, day 2 is used to differentiate induced pluripotent stem cells into primitive streak/mesendoderm.
Figure 17:
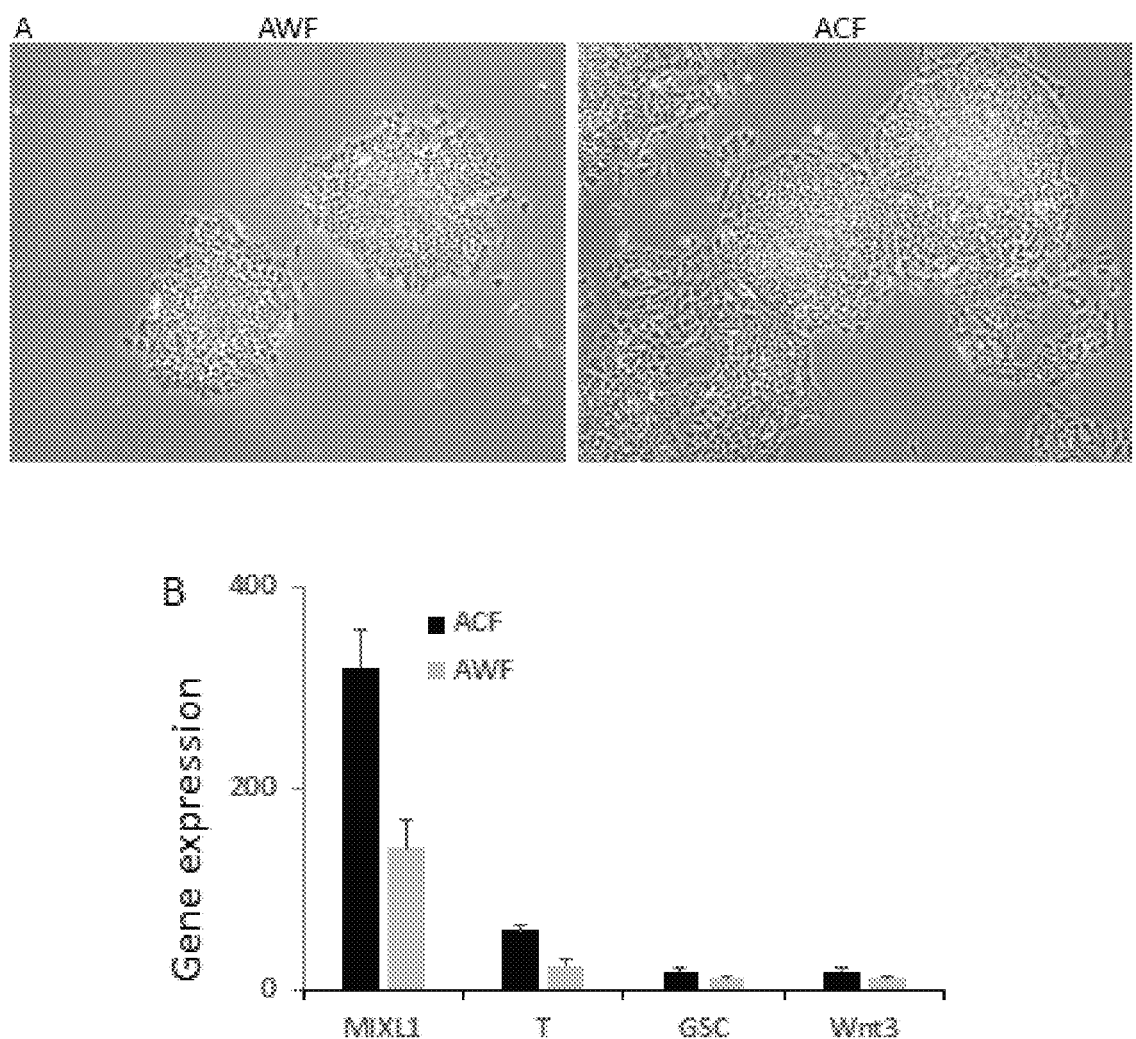

To ensure high efficiency of iPSCs toward PS or PS-like mesendoderm, low confluent iPSCs (around 20%) with small clumps were used. Compared with treatment for 1 day, treatment for 2 days greatly enhanced differentiation toward PS-like mesendoderm (FIG. 8). The results also show that activin A enhanced differentiation towards PS-like mesendoderm expressing T, MIXL1 and GSC. However, the expression of endodermal marker Sox17 was also increased with the dose of activin A (FIG. 9A). The ratio of increased MIXL1 or T to Sox17 was the highest at 25 ng/ml of activin A (FIG. 9B), 25 ng/ml activin A was therefore used in the study. The data also showed that Activin A and ChIR99021 greatly synergized differentiation iPSCs to obtain PS-like mesendoderm. Compared with wnt3a (ACF vs AWF), CHIR99021 promoted the adherence of iPSCs to the dish (FIG. 17A) as well as promoted differentiation toward PS-like mesendoderm (FIG. 17B). The replacement of growth factor wnt3a with small molecule CHIR99021 is very useful for clinical application due to the lower cost of CHIR99021. Although addition of FGF at day 2 did not further enhance differentiation toward PS-like mesendoderm, expression of mesoderm increased in the presence of FGF. The expression of mesoderm predisposed next stage of differentiation towards mesoderm.

In contrast to the undifferentiated iPSCs at day 0, most cells after day 2 of differentiation showed large nuclei and prominent nucleoi. The pluripotency genes Sox2 significantly decreased, while Oct4 and Nanog continued to be expressed at levels similar to those of iPSCs (FIG. 12C).

Figure 12:
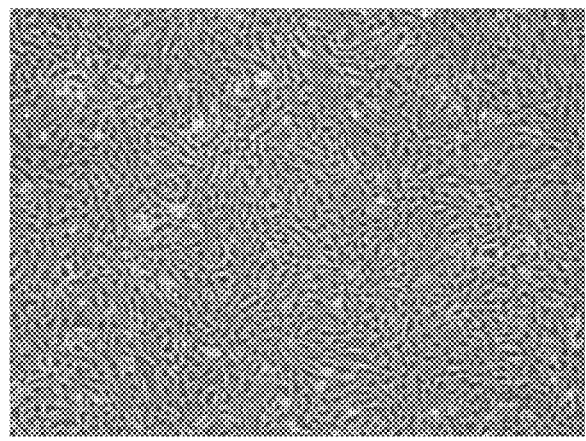
FIG. 12 shows the results of characterization of the cells obtained from induced pluripotent stem cells using the method of generating mature mesenchymal stem cells as disclosed herein (i.e. iPSC-MSC).
Figure 12:
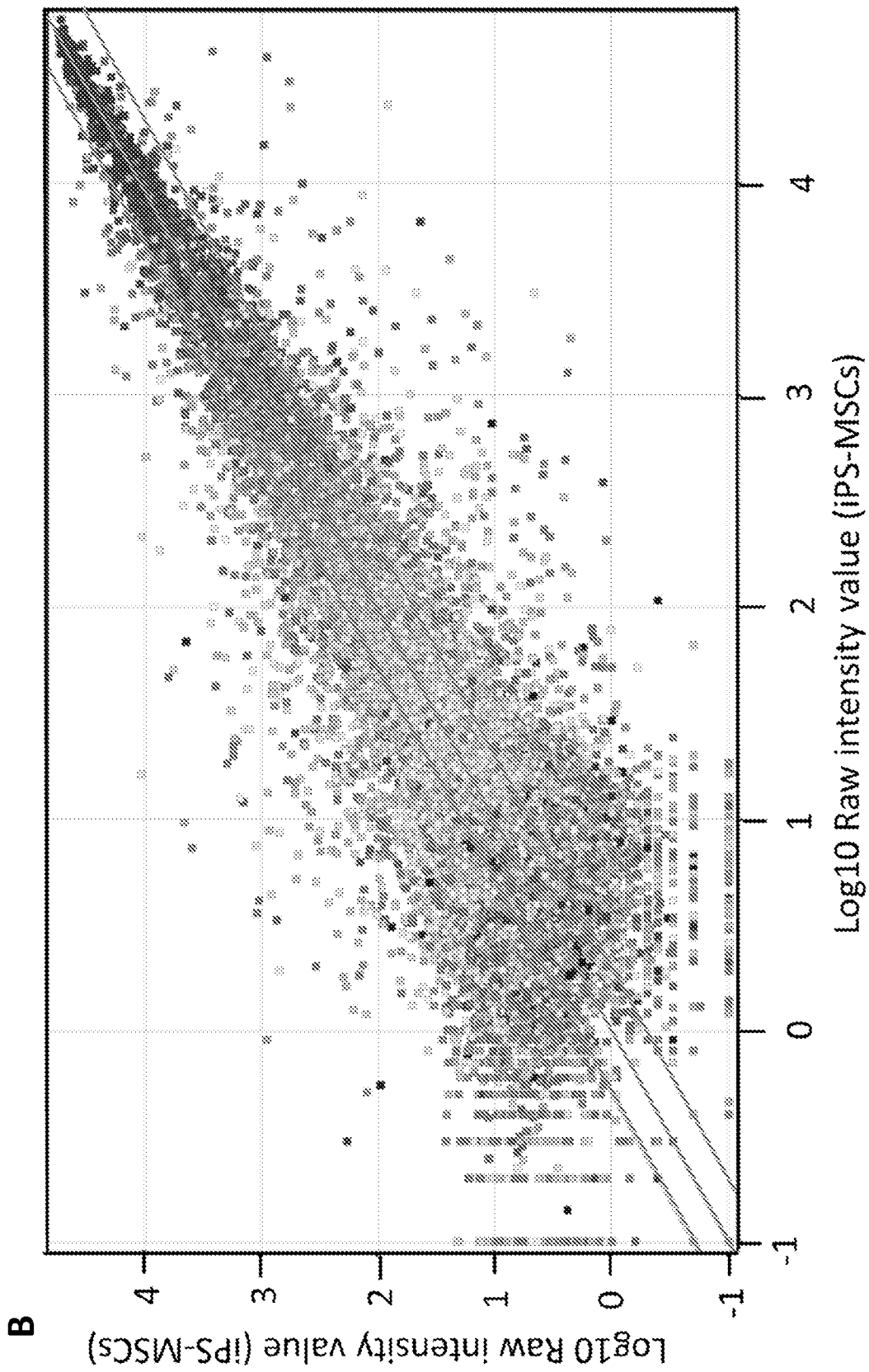
Figure 12:
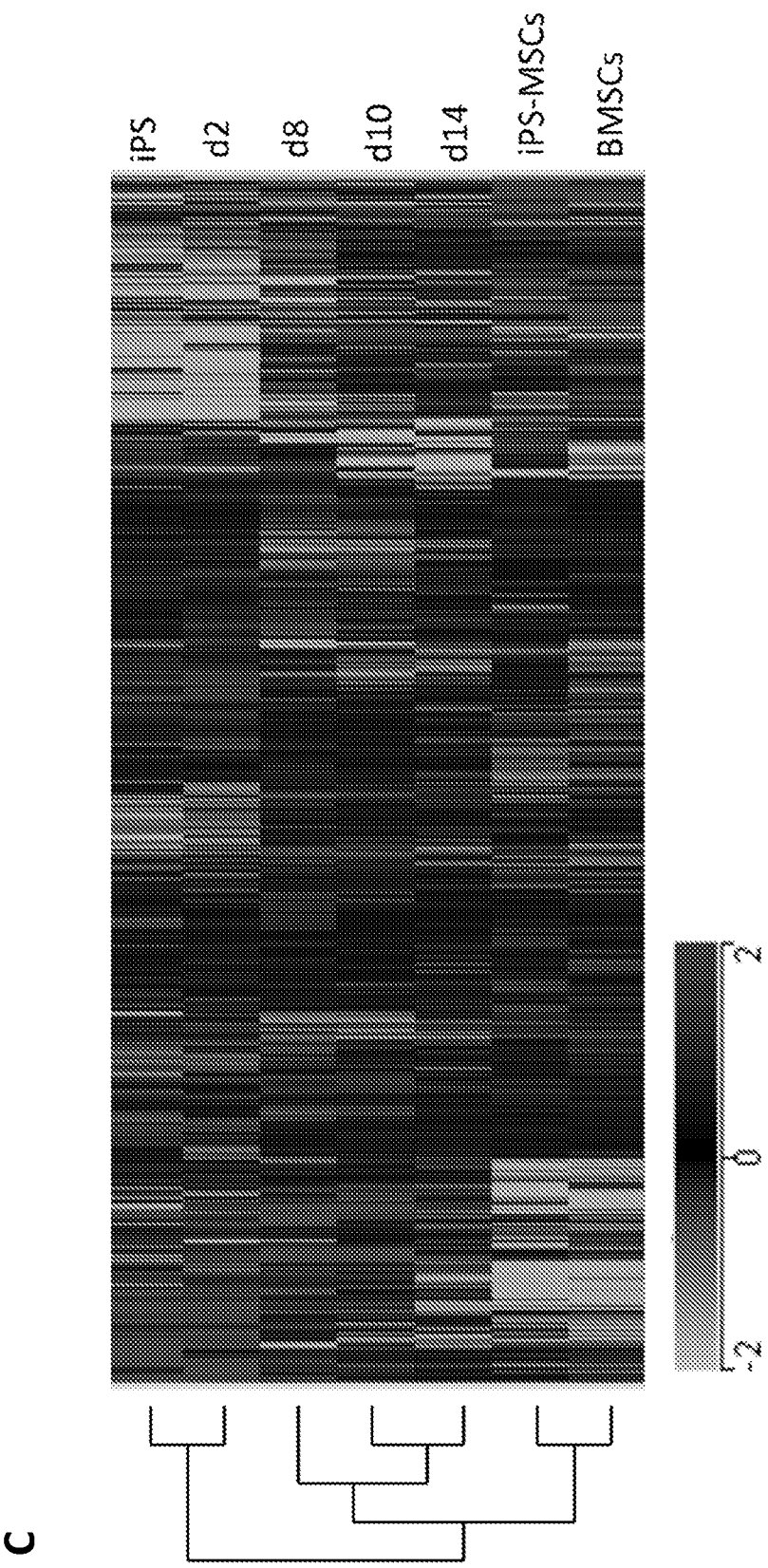
Figure 12:
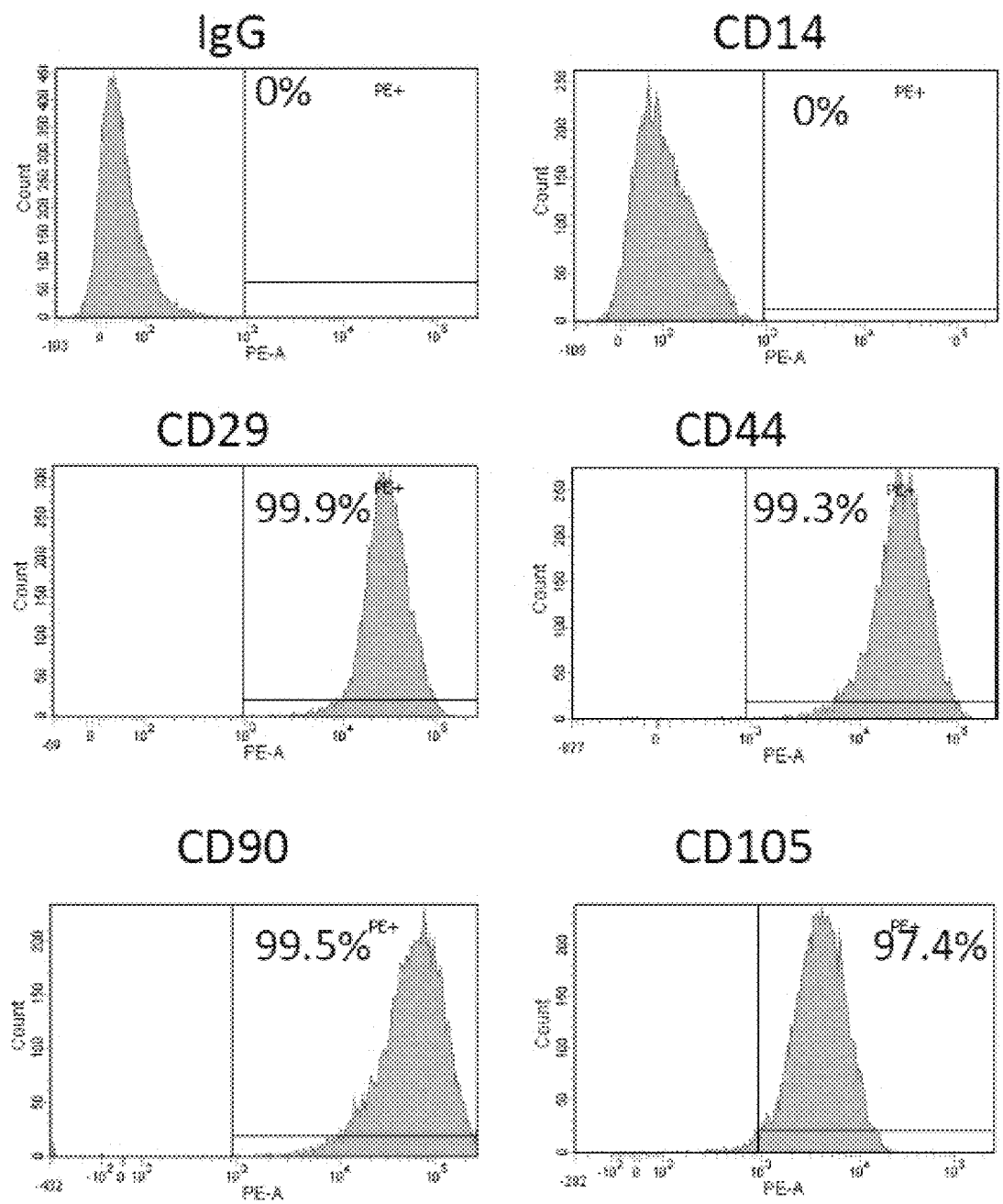
Figure 12:
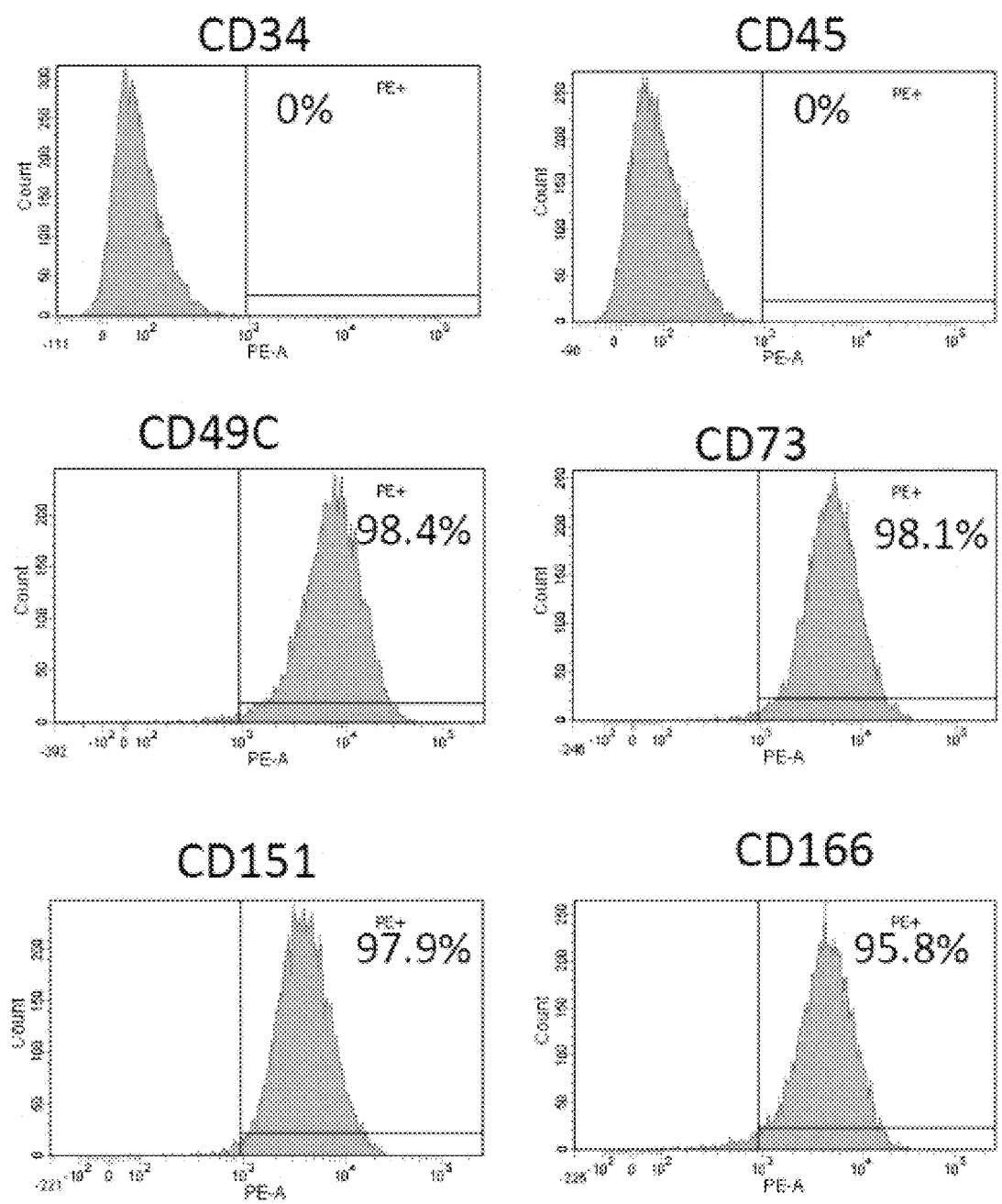
Figure 12:
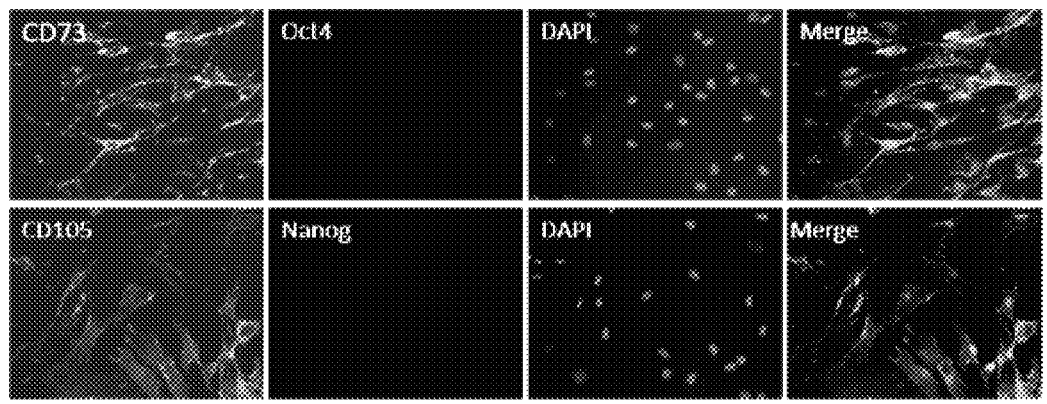
Figure 12:
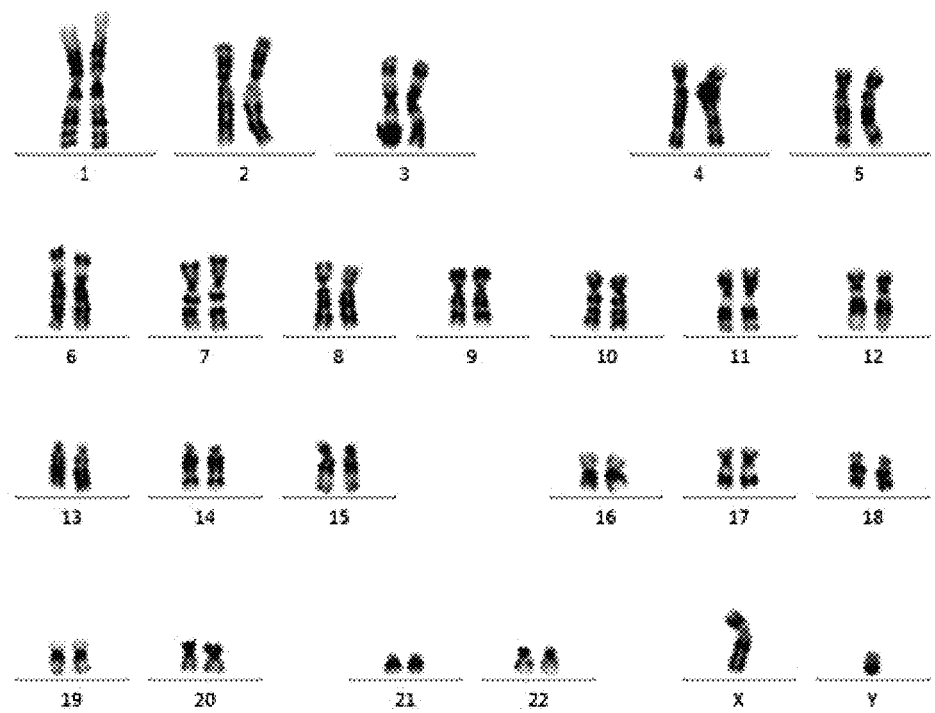
Figure 12:
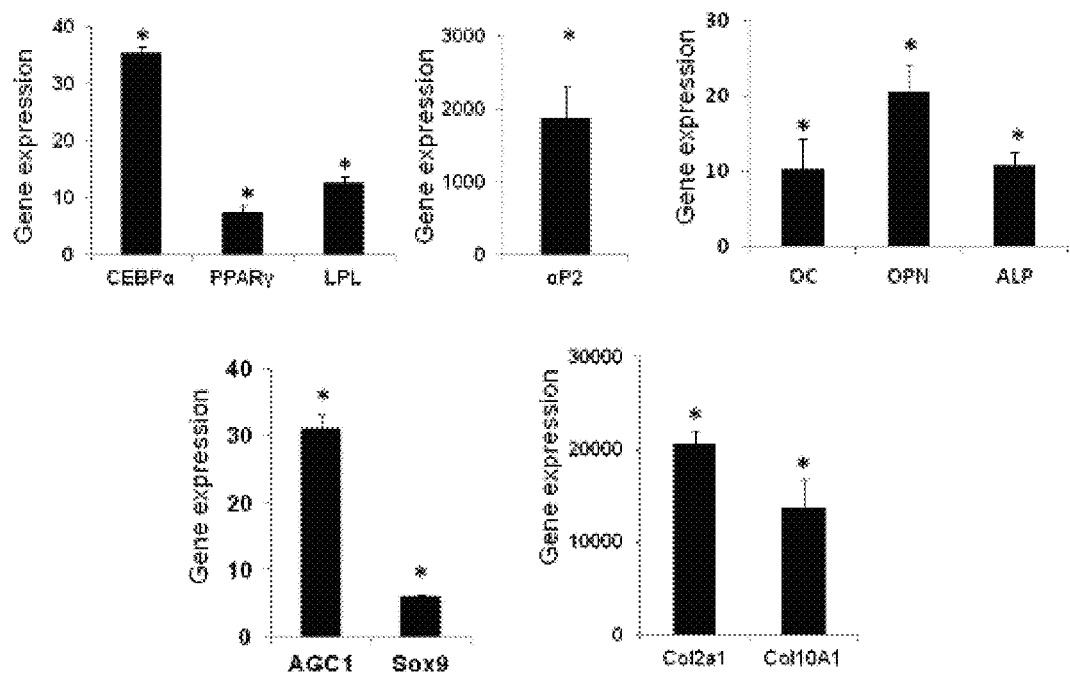
Figure 12:
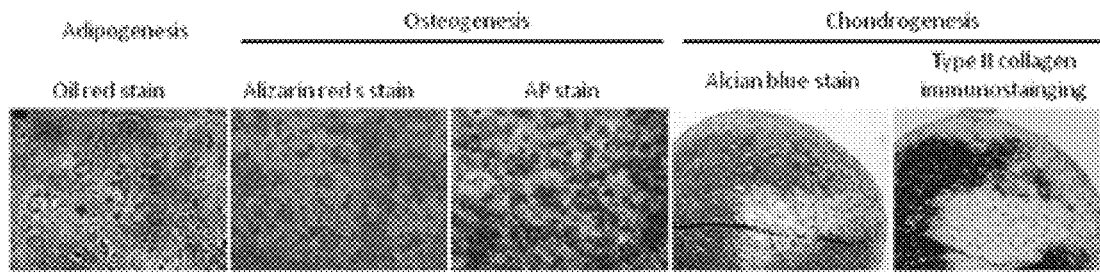

Brachyury (T), the target of the Wnt/f3-catenin signaling pathway peaked at day 2 with PS-mesendoderm genes MIXL1 and GSC, and decreased rapidly thereafter (FIG. 12C). FACS data showed that 98.13±1.7% brachyury (T), 97.53±0.7% MIXL1 and 98.77±1.13% GSC were yielded at day 2 (FIG. 9C). Immunofluorescence was consistent with FACS data (FIG. 9D). SP5 encodes a protein having a C-terminal C(2)H(2) zinc finger domain, which is regulated by Wnt3a in the PS and binds to the GC box present in the promoter of brachyury. The data of the present application showed that Sp5 peaked at day 2 and was not expressed in iPSC-MSCs. ChIP-seq showed that differentiated cells at day 2 were active in T and Wnt3 (FIG. 9E). These data demonstrated that iPSCs were efficiently differentiated toward PS-like mesendoderm at day 2.

Example 3—Differentiation of Primitive Streak or Primitive Streak-Like Mesendoderm Cells Towards Mesoderm Cells Mesoderm differentiation was induced with FGF (20 ng/ml), BMP4 (40 ng/ml), rock inhibitor Y27632 (5 μM, only used at the time of passage and remove the next day) and follistatin (100 ng/ml) for 8 days.

Figure 10:
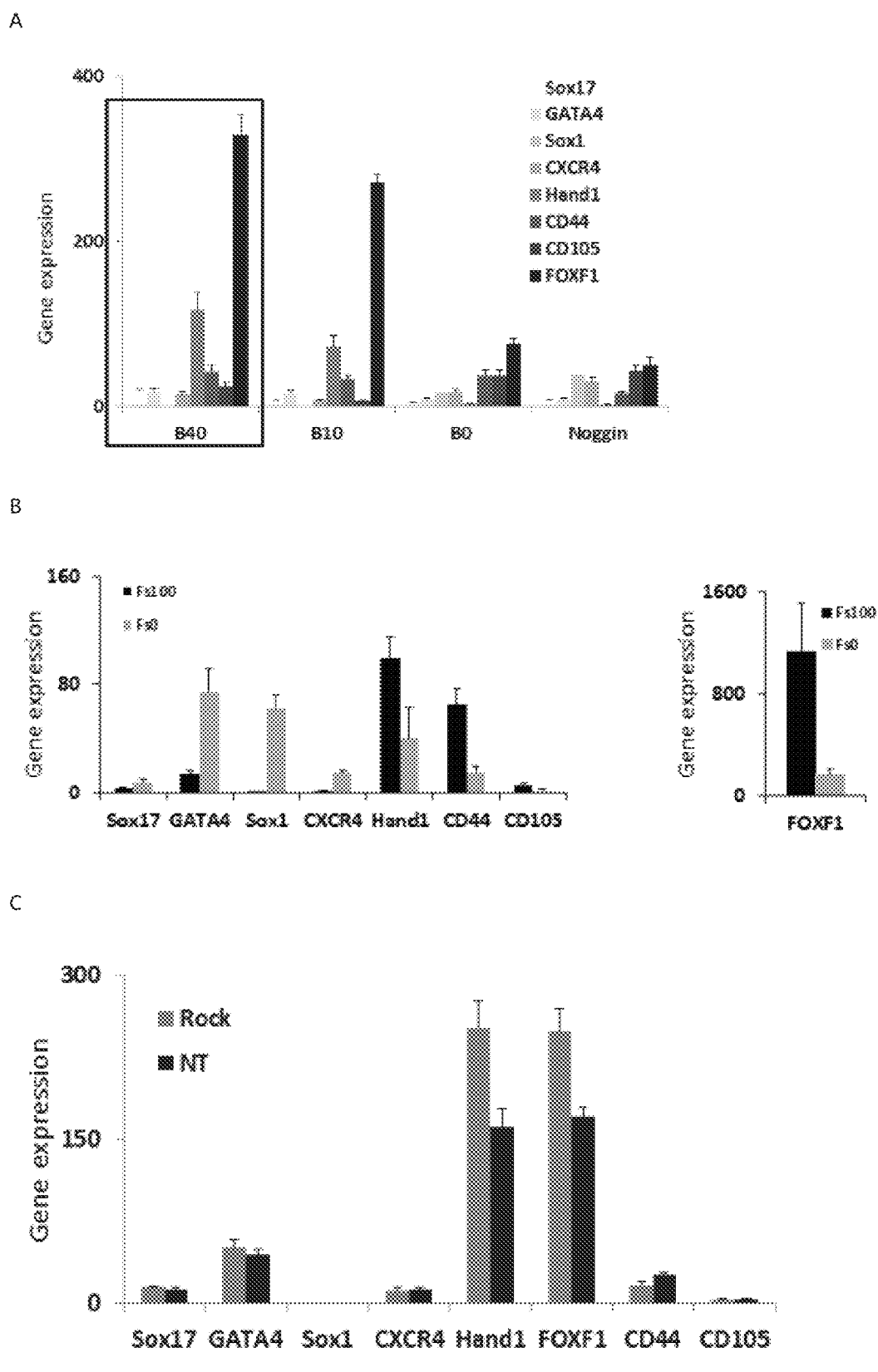
FIG. 10 shows the differentiation of primitive streak (PS)-like mesendoderm cells towards lateral plate-like mesoderm cells.
Figure 10:
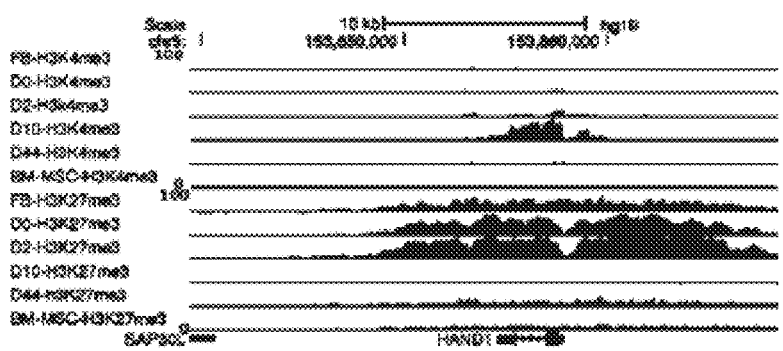

To determine concentrations of BMP4 for mesodermal differentiation, the present data showed that 40 ng/ml BMP4 led to the highest expression of lateral plate mesoderm markers. On the contrary, ectodermal gene Sox1 was also highly expressed in the absence of BMP4 or in the presence of noggin (38.65-fold) (FIG. 10A). The present data showed that follistatin inhibited endodermal differentiation Sox17 and FOXA1, while promoting mesodermal differentiation (FIG. 10B). To promote cell survival and reduce cell death, FGF and a ROCK inhibitor Y27632 were used. Compared with cytokine neurotrophi-4 (NT), ROCK inhibitor Y27632 increased cell number by 3.53±1.56 fold at day 10. At the same time, Y27632 increased the expression of lateral plate mesoderm genes Hand1 and FOXF1 (FIG. 10 C).

During embryogenesis, lateral plate mesoderm contributes to cartilage and bone of limb. Specification of lateral plate mesoderm requires higher concentration of BMP4. Under defined condition, pluripotency gene Oct4 decreased to 1.3% ($p<0.001$), Nanog and Sox2 decreased to 0.85% ($p<0.01$) and 0.77% ($p<0.001$). PS gene T decreased to the level similar to iPSCs. MIXL1 and GSC were significantly down-regulated to 3.64-fold and 2.59-fold relatively to iPSCs, respectively. Paraxial markers Tbx6, TCF15, MESP2 and MEOX2 were not upregulated at day 10, suggesting that paraxial mesoderm is achieved. By contrast, lateral plate markers, highly expressed FOXF1 (572.7-fold, $p=0.01$) and Hand1 (203-fold, $p=0.005$) were observed at day 10. It was consistent with active Hand1 by ChIP-seq at day 10 (FIG. 10D). APLNR was also highly expressed at day 10 (145.4-fold, $p=0.011$) (FIG. 12C). It was previously shown that APLNR was expressed in mesenchymoangioblast, a common precursor of mesenchymal and endothelial cells mesenchymoangioblast, which gives rise to mesoderm-derived MSCs.

Example 4—Differentiation of Mesoderm Cells Towards Mesenchymal Stem Cells

Referring to FIG. 1, stage 3 of the protocol aimed at induction and maturation of mesoderm toward MSCs using medium containing FGF, PDGF, EGF and ascorbic acid, and optionally TGFβ1. The maturation of MSCs is associated with step-wise acquisition of a specific lineage identity. Cells at day 10 were cultured in media containing FGF (5 ng/ml), PDGF-AB (5 ng/ml), TGFb1 (5 ug/ml), EGF (10 ng/ml) and Vc (50 ug/ml) for subsequent 11 days. Differentiated cells ware passaged with accutase (Millipore) and maintained under subconfluent condition.

Directed differentiation toward MSCs was assessed by quantitative PCR (qPCR) for expression of genes associated with pluripotent genes (Oct4, Nanog and Sox2), primitive streak-mesendodermal (MIXL1, T, GSC and Wnt3), mesodermal (FOXF1, Hand1, PDGFRα, PDGFRI3), endodermal (Sox17, GATA4, FOXA1 and FOXA2), neurectodermal (SOX1, PAXS), and MSC (CD44, CD73, CD105). The efficiency of differentiation was evaluated by Fluorescence-activated cell sorting (FACS).

Figure 11:
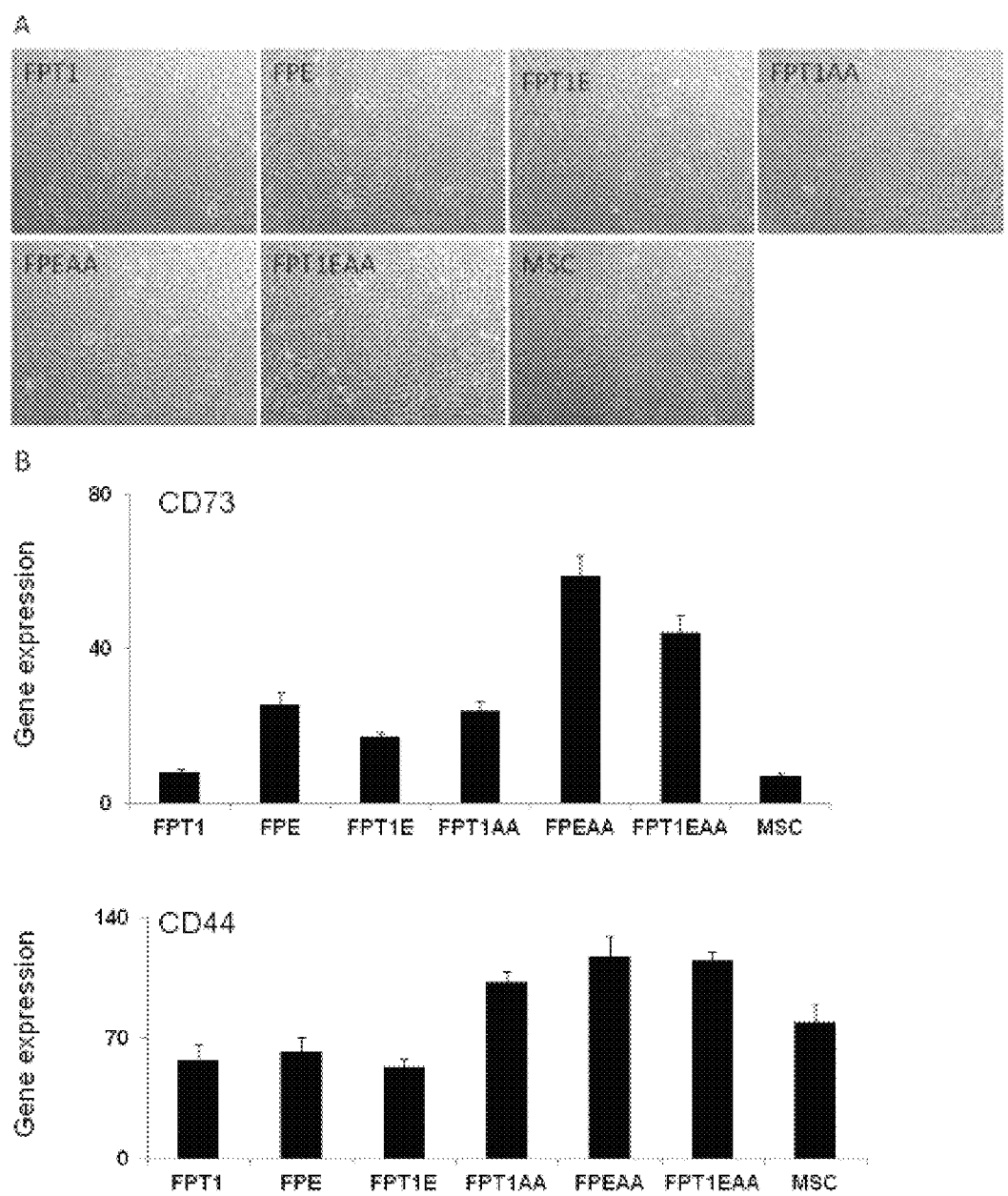
FIG. 11 shows the differentiation of lateral plate-like mesoderm cells towards mature mesenchymal stem cells.
Figure 11:
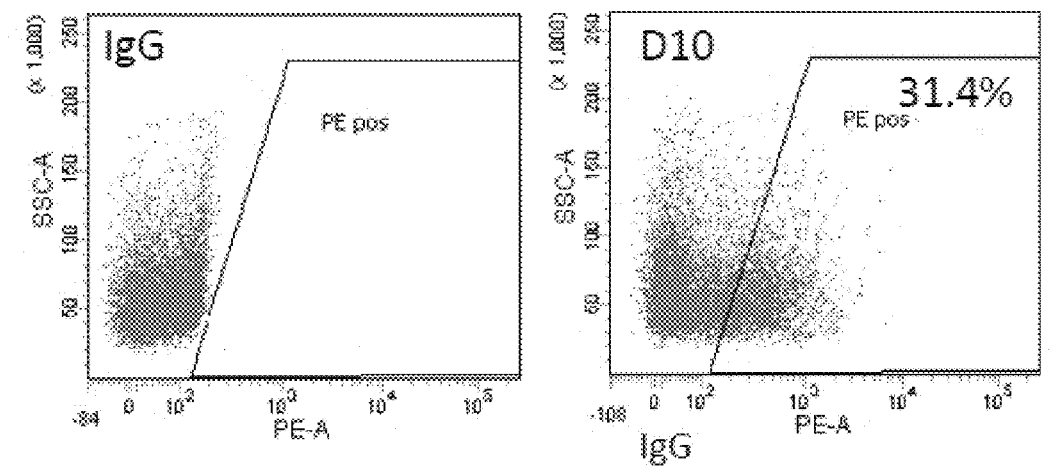
Figure 11:
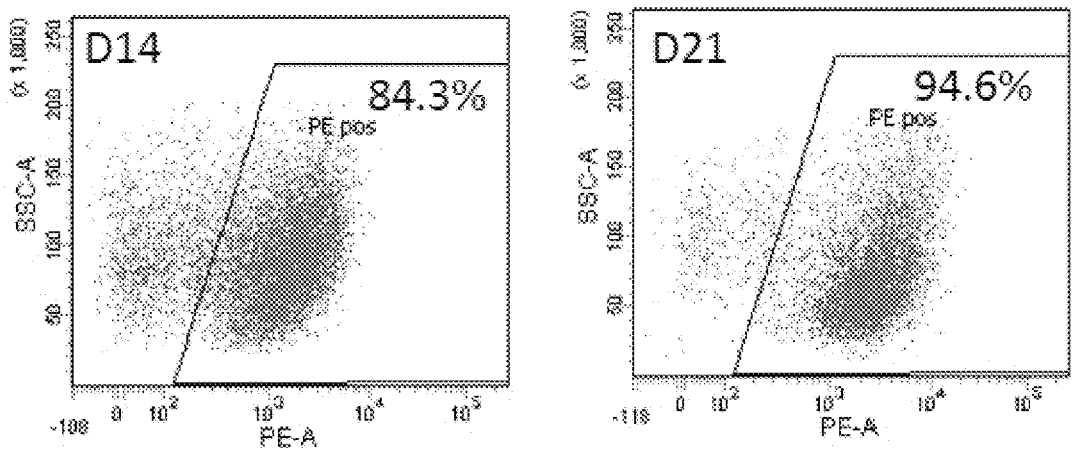
Figure 11:
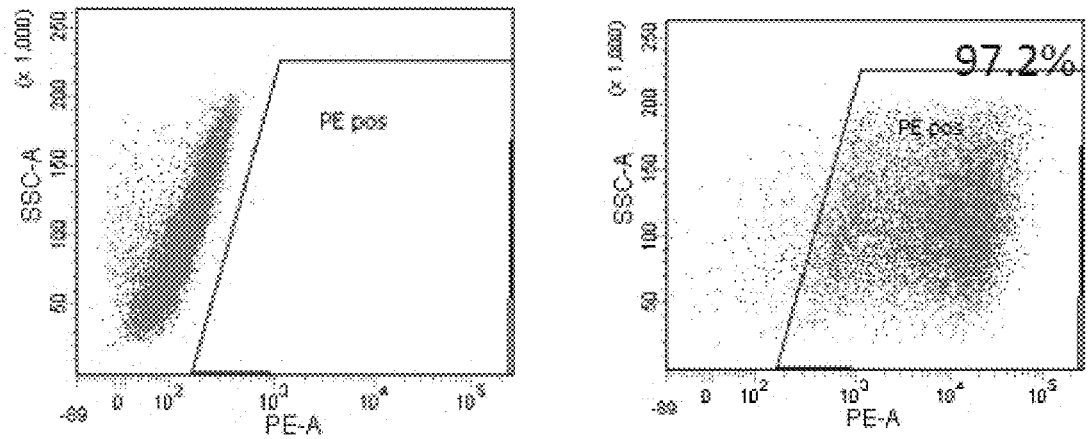
Figure 11:
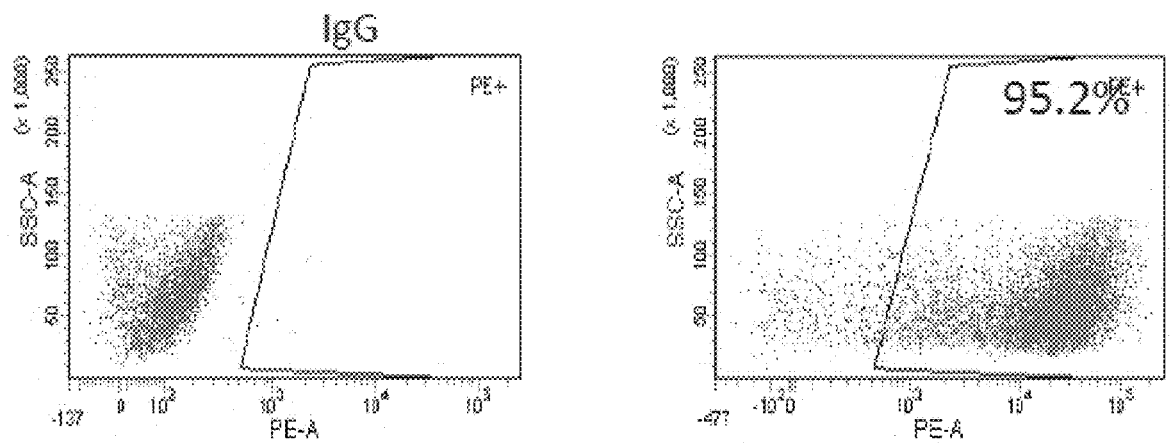
Figure 11:
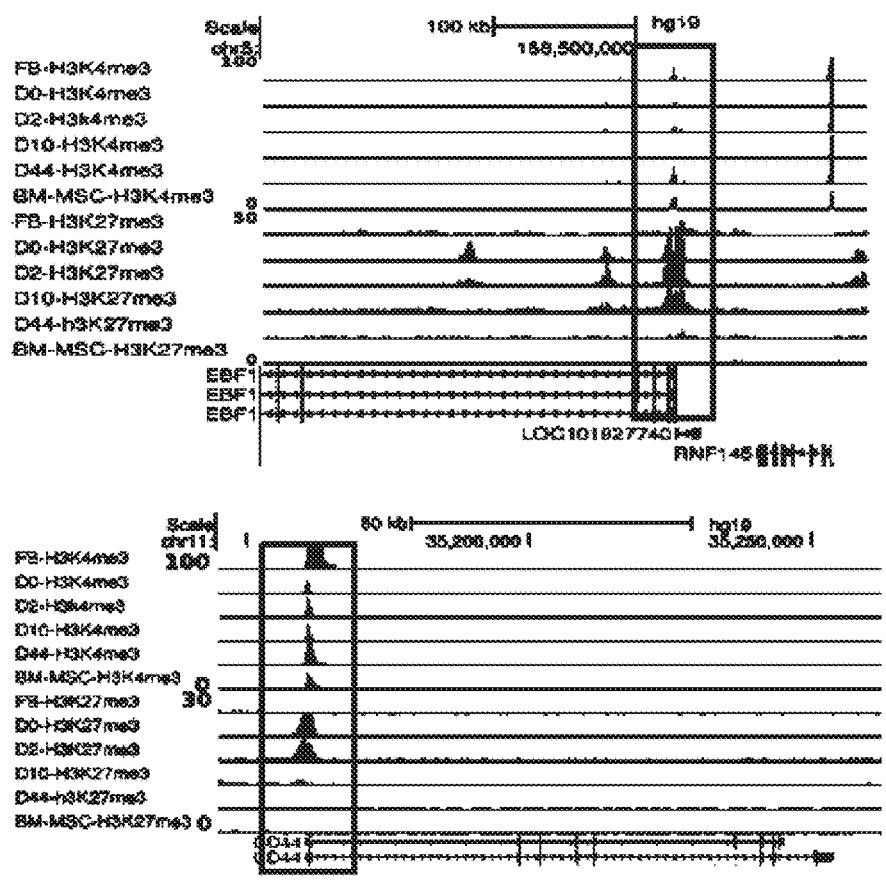

No significant morphological changes were observed between day 10 and 14. At day 21, cells became elongated and adopted morphology similar to primary MSCs from bone marrow (FIGS. 11A and 11B).

Figure 4:
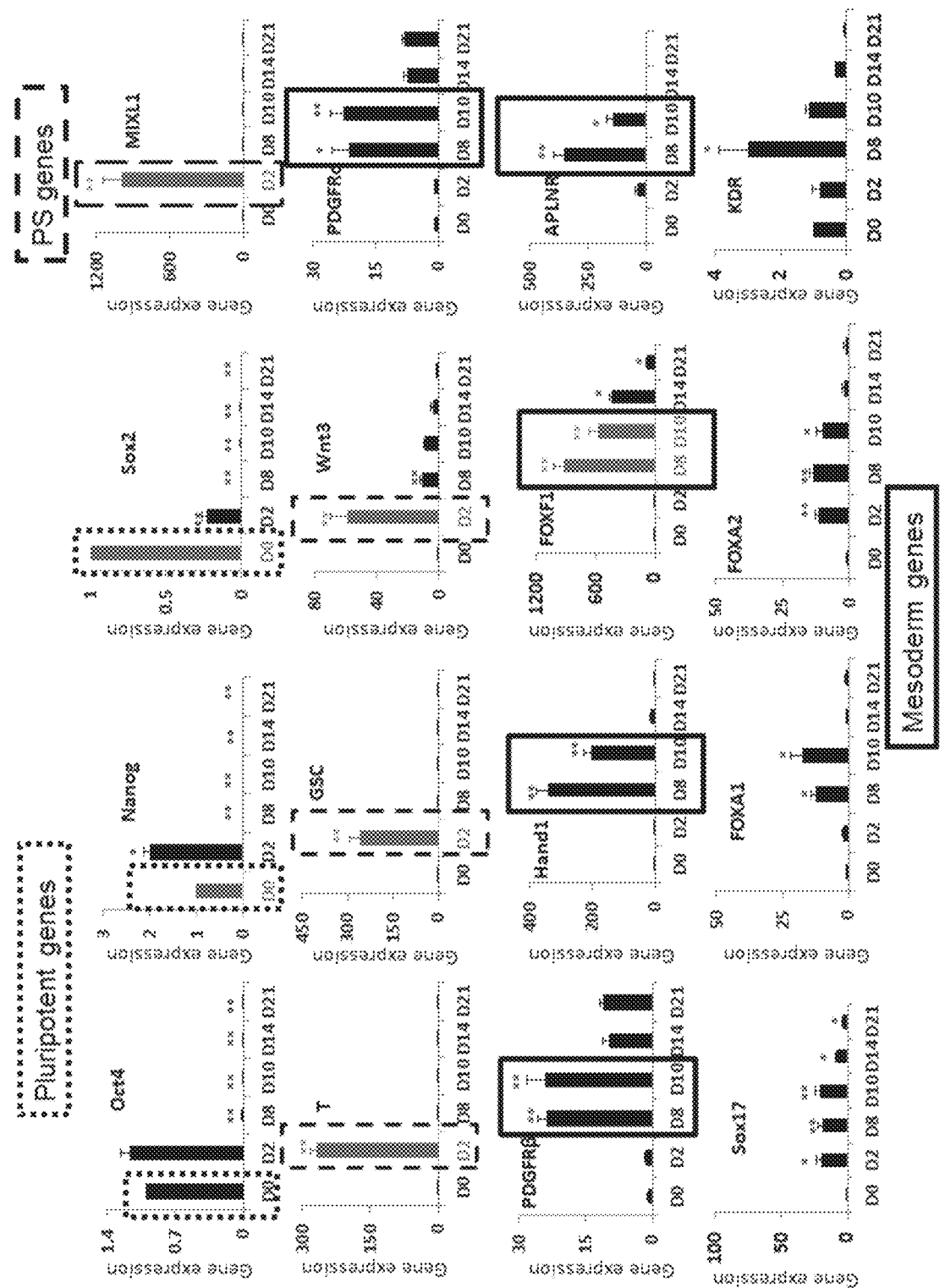
FIGS. 4 and 5 show stage specific gene expression measured by qPCR during differentiation from induced pluripotent stem cells to mesenchymal stem cells (MSCs) undergoing primitive streak/mesendoderm and mesoderm. Pluripotent genes include OCT4, Nanog and Sox2; primitive streak/mesendoderm genes include MIXL1, T, GSC and Wnt3; mesodermal genes include Hand1, FOXF1, APLNR; MSC genes include CD44, CD73 and CD105.
Figure 5:
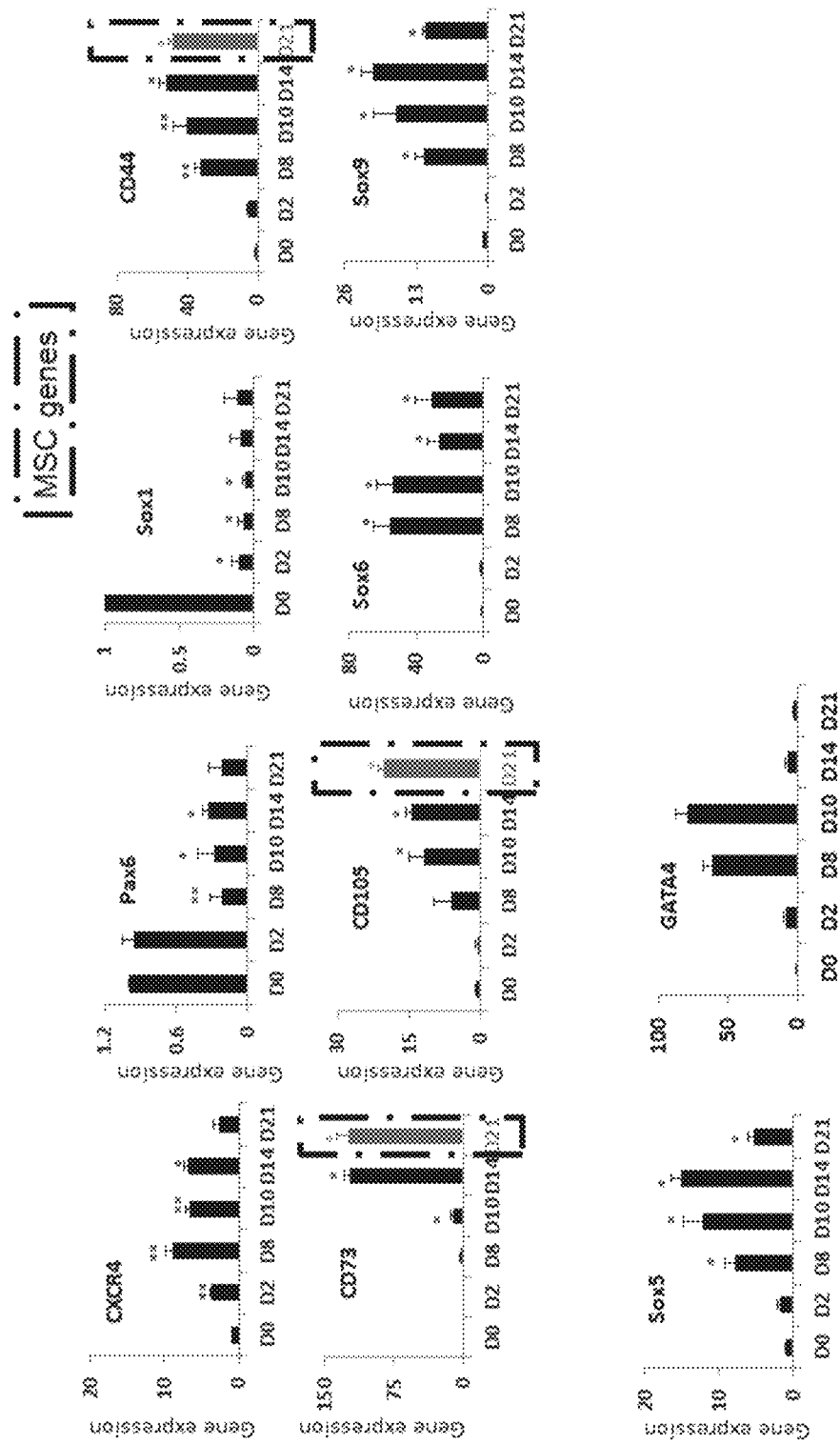
Figure 6:
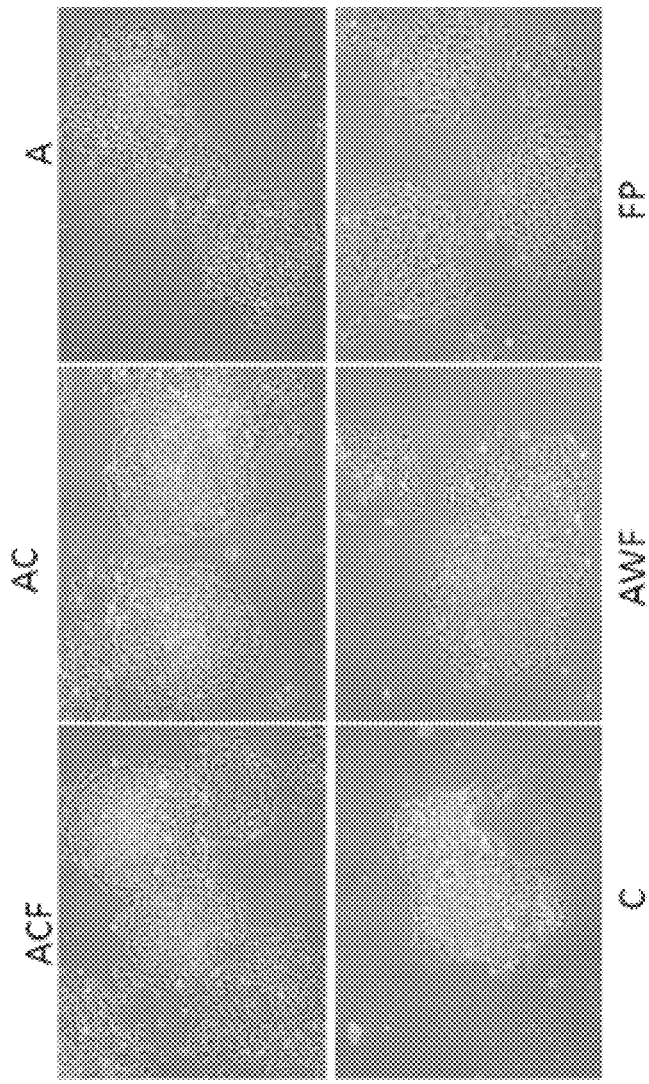
FIG. 6 shows that combination of Activin A, CHIR99021 and FGF can more effectively induce the differentiation of induced pluripotent stem cells to primitive streak/messemdoderm as compared to other combinations of growth factors, as shown by the differentiated morphology and cell number.
Figure 7:
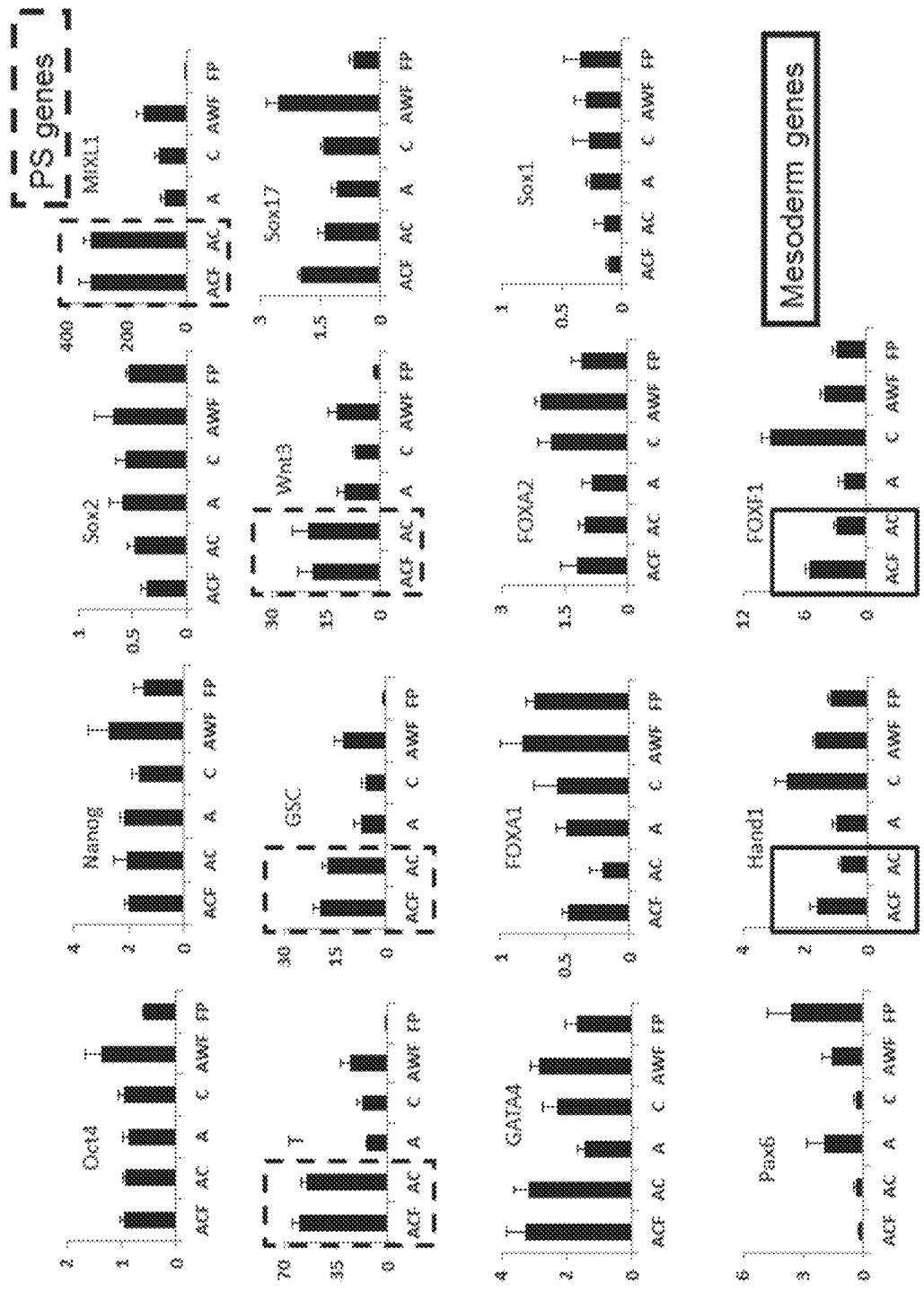
FIG. 7 shows that differentiated cells express higher primitive streak/mesendoderm genes (MIXL1, T, GSC and Wnt3) under combination of Activin A, CHIR99021 and FGF for 2 days compared with other conditions, as measured by qPCR.

The cells did not express the pluripotency genes Oct4, Nanog and Sox2 as well as PS-mesendoderm genes T, MIXL1 and GSC. Mesodermal genes PDGFRα and PDGFRβ decreased from day 14. Hand1 and FOXF1 continuously decreased over time whereas CD73 peaked at day 14, which makes it possible to isolate MSC precursors from already-established MSCs. Endodermal genes SOX17 continuously decreased, FOXA1 and FOXA2 decreased at day 14 and 21. CD105 continuously increased over time and CD44 increased until day 21 (FIG. 4 and FIG. 5). The FACS analysis showed that 84.3% cells were positive for CD73 at day 14 and 94.6% for day 21 (FIG. 11C). ChIP-seq data showed that CD44 was not suppressed, and EBF1 was active in MSCs (FIG. 11D). CD73 positive cells were sorted and expanded for characterization and cartilage repair.

Example 5—Characterization of iPSC-MSCs

Figure 18:
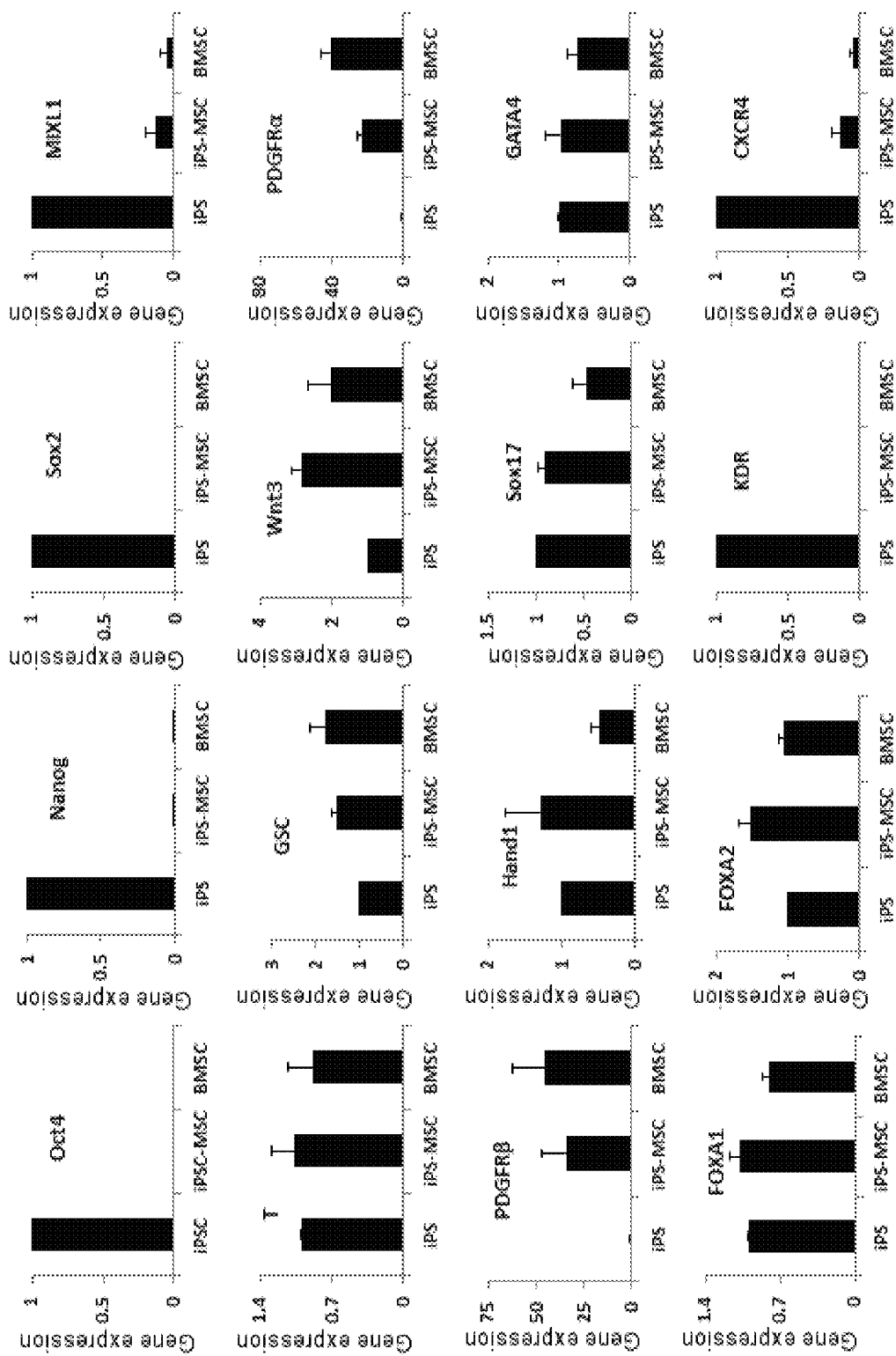
FIG. 18 shows that iPSC-MSCs displayed similar gene expression profile to primary MSCs, as measured by qPCR. iPSC-MSCs were absent for pluripotent genes (Oct4, Nanog and Sox2), primitive streak/mesendodermal genes (MIXL1, T, GSC and Wnt3), endodermal genes (Sox17, GATA4, FOXA1 and FOXA2), ectodermal genes (Pax6 and Sox1), but expressed MSC genes (CD44, CD73 and CD105) similar to the primary MSCs, as detected by RT-PCR.
Figure 18:
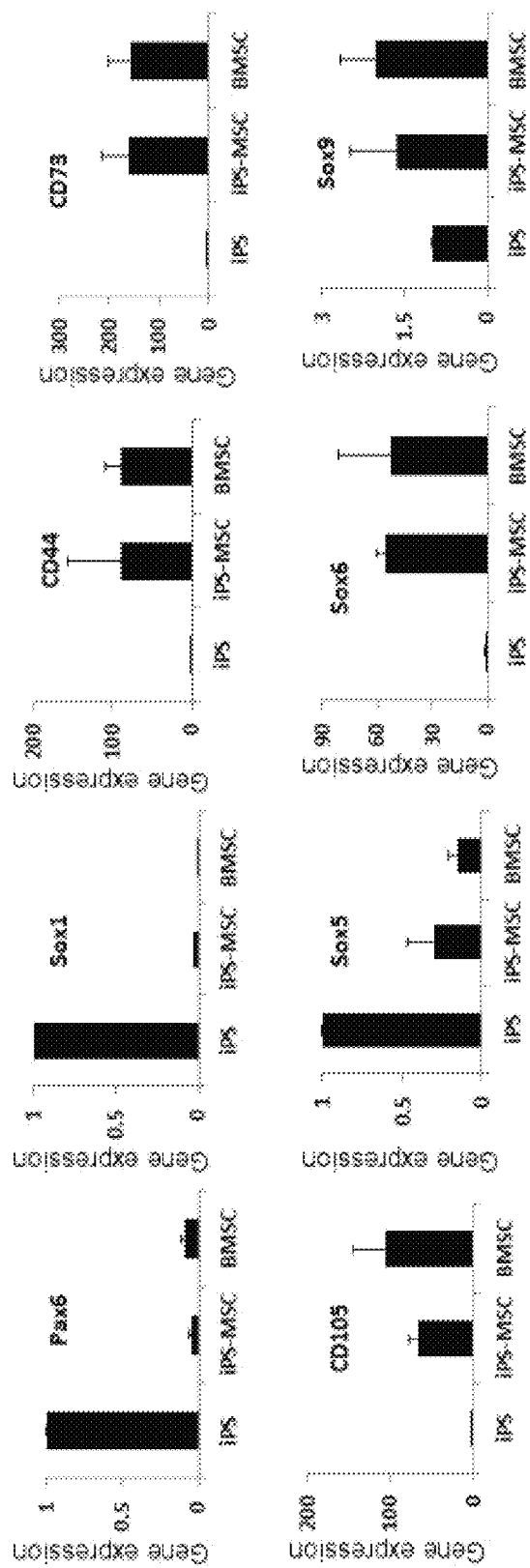

MSC obtained using the methods disclosed herein displayed fibroblast-like cells similar to primary MSCs (FIG. 12A). To understand the molecular difference between iPSC-MSCs and BMSCs, the gene expression profile of iPSC-MSCs was compared with that of BMSCs. Correlation coefficient between iPSC-MSCs and BMSCS was 0.954, and the gene expression profile of iPSC-MSCs is more closely clustered with that of BMSCs. These data showed that iPSC-MSCs displayed similar surface antigen profiles to primary MSCs (FIGS. 12B and 12C). iPSC-MSCs were absent for pluripotent genes (Oct4, Nanog and Sox2), endodermal genes (Sox17, GATA4, FOXA1 and FOXA2), ectodermal genes (Pax6 and Sox1) detected in by RT-PCR (FIG. 18). iPSC-MSCs were negative for CD14, CD34 and CD45, but positive for CD29, CD44, CD49C, CD90, CD105, CD151 and CD166 by FACS analysis, showing that iPSC-MSCs displayed similar surface antigen profile to BMSCs (FIG. 12D). Immunofluoresence was consistent with FACS (FIG. 12E). Karyotyping showed that iPSC-MSCs were normal (FIG. 12F). When iPSC-MSCs were subcutaneously transplanted into immunodeficient mice, no tumor was observed after 12 weeks.

Example 6—Osteoblast, Chondrocyte and Adipocyte Differentiation of iPSC-MSCs iPSC-MSCs were cultured under sub-confluent condition to prevent spontaneous differentiation. MSCs were induced to differentiate towards adipocytes in adipogenic medium and osteoblasts in osteogenic medium for 14 days. Pellet culture system was used for chondrocyte differentiation for 28 days. Cells in growth medium were used as control. Adipogenic medium contained 0.5 mM isobutyl-methylxanthine (IBMX), 1 µM dexamethasone, 10 µM insulin, 200 µM indomethacin and 1% antibiotic/antimycotic. Osteogenic medium contained 0.1 µM dexamethasone, 50 µM ascorbate-2-phosphate, 10 mM 0-glycerophosphate and 1% antibiotic/antimycotic. Chondrogenic media contained 10 ng/ml transforming growth factor (TGF)-β3, 0.1 µM dexamethasone, 50 m/ml ascorbate-2-phosphate, 40m/ml proline, 100 µg/ml pyruvate, and 50 mg/ml ITS+Premix (Becton Dickinson; 6.25 µg/ml insulin, 6.25m/ml transferrin, 6.25m/ml selenious acid, 1.25 mg/ml BSA, and 5.35 mg/ml linoleic acid). The supplements are purchased from Sigma, unless otherwise stated. The medium was replaced every 3-4 days. Differentiation of MSCs was evaluated by real-time RT-PCR and lineage specific staining. Oil red 0 stain for lipid deposits in adipogenesis, Alizarin red S stain for calcium deposits and AP stain for alkaline phosphatase in osteogenesis, Type II collagen immunostain for major collagen of cartilage and alcian blue stain for cartilage proteoglycans in chondrogenesis were used in this study.

The results show that after 2 weeks of adipogenesis, adipogenic markers CEBPa, PPARγ, LPL and αP2 were expressed in differentiated iPSC-MSCs under adipogenic medium (FIG. 12G). iPSC-MSCs were positive for oil red S staining for oil droplets (FIG. 12F). Similarly, iPSC-MSCs were induced into osteogenesis for 2 weeks, osteogenic markers OC, OPN and ALP were also upregulated (FIG. 12G). iPSC-MSCs were positive for alizarin red stain for calcium deposits and AP stain for alkaline phosphatase activity, showing that iPSC-MSCs have osteogenic differentiation potential (FIG. 12F). After 4 weeks of chondrogenesis under pellet cultures in chondrogenic medium, chondrogenic markers Col2A1, AGC1, the master regulator of chondrogenesis Sox9 and Col10A1 were highly expressed (FIG. 12G). iPSC-MSCs were consistently positive for Alcian blue stain for sulfated proteoglycan matrix and type II immunostaining for major collagen in cartilage (FIG. 12H). Collectively, the above data shows that iPSC-MSCs had three mesenchymal lineage differentiation potential.

Example 7—the Molecular Mechanisms Underlying MSC Development

Figure 13:
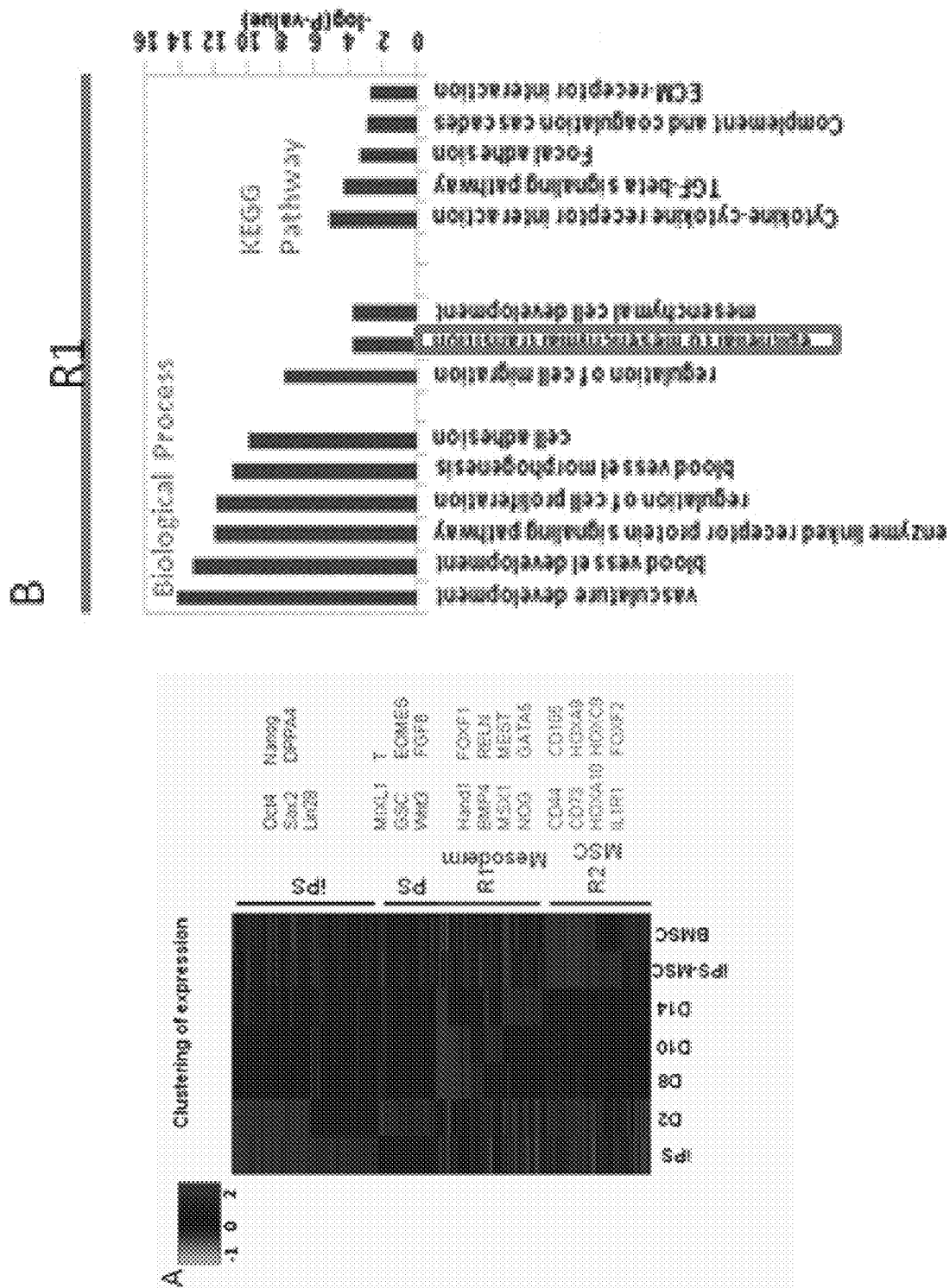
FIG. 13 shows that the epithelial-mesenchymal transition (EMT) is crucial for the development of mature mesenchymal stem cells.
Figure 13:
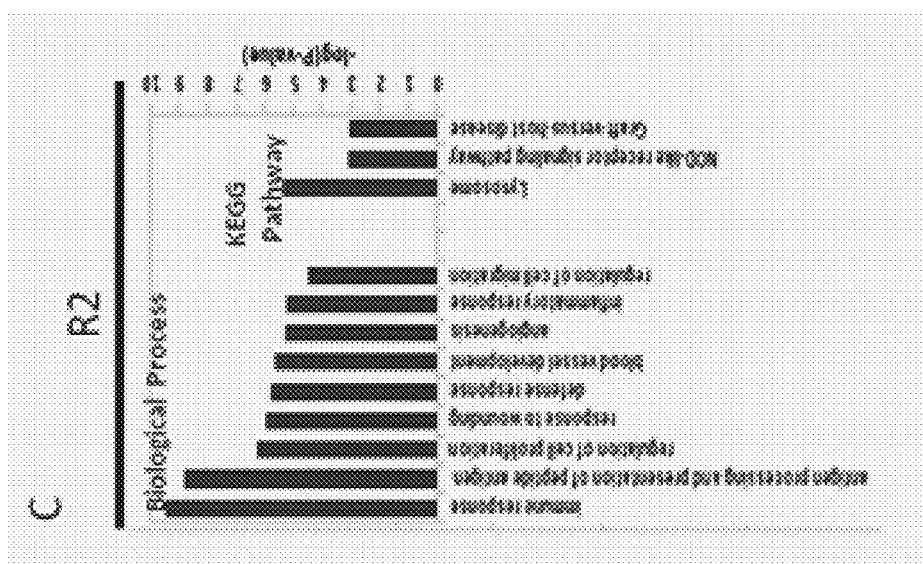
Figure 13:
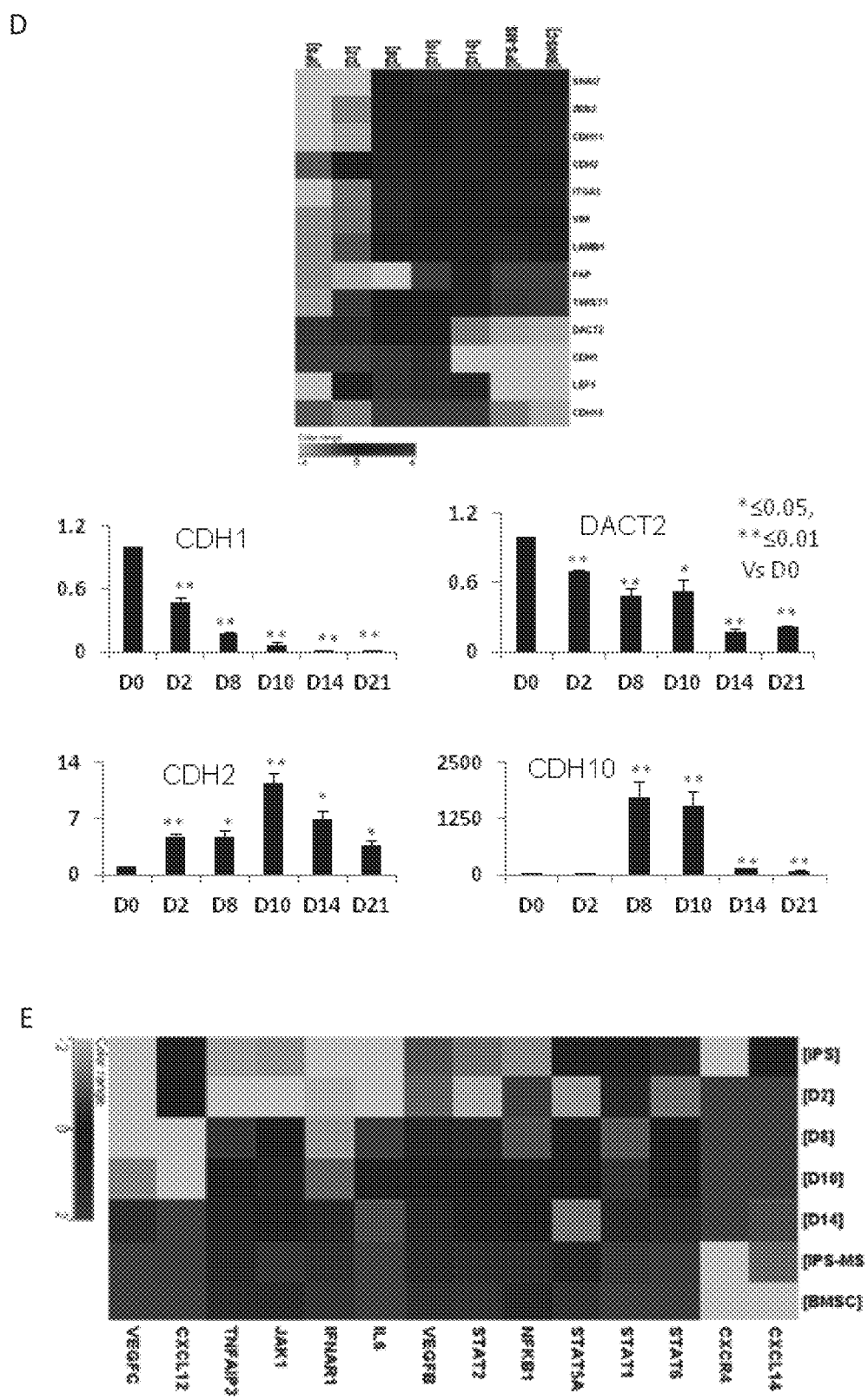

Although MSCs have been studied for many years, the molecular mechanisms underlying MSC development is poorly understood, including transcription regulation, especially at the chromatin level. To decipher the precise molecular events of MSC development, the defined differentiation protocol to recapitulate the major stage of MSC development is established. Clustering of gene-expression of BMSC and 6 stages of differentiation (namely Day-0 (iPS), Day-2, Day-8, Day-10, Day-14 and iPSC-MSC) were carried out. The microarray data showed that differentiation of iPSCs towards MSCs underwent primitive streak/mesendoderm, mesoderm and maturation of MSCs (FIG. 13A). Upon binary clustering, high similarity between iPSC-MSC and BMSC gene-expression profiles were shown. Interestingly, genes from day 8 to day 14 had significant enrichment of gene ontology term related to mesodermal subtypes such as epithelial to mesenchymal transformation and mesenchymal cell development (FIG. 13B). It is consistent that epithelial-mesenchymal transition (EMT) is a crucial process for specification and differentiation. Pathways enriched for those genes of MSCs (R2) are TGF-beta signaling, immune response, regulation of cell proliferation and Graft-versus-host disease (FIG. 13C).

In order to gain insight into changes in regulatory circuits during EMT stage and MSC formation, regression analysis was performed using motif occurrence and fold-change in expression at two stages. The change in expression between D8 and median of DO (iPSC) and D2 was first modelled. The top predictor motif during EMT related expression change (D8 Vs DO and D2) included IRF, GLI, SMAD3, Ap2-alpha, Foxp and Meisl. Some of these genes are already known to promote EMT—for example, GLI is known to promote EMT through HedgeHog pathway; SMAD3 promotes EMT as a downstream effector of the TGF-beta pathway. The inventors then modeled the ratio of expression of iPSC-MSC and median of expression during EMT (D8, D10, D14). The inventors found Ap-1, GATA-3, IRF2, STAT, ETS and FOXD1 as top predictor of higher expression in MSC compared to EMT stages.

During EMT, the loss of epithelia markers and acquisition of mesenchymal features are achieved through a well-orchestrated transcription program that involves snail, ZEB and bHLH families (such as Twist 1). Down-regulation of E-cadherin is a fundamental event of EMT. E-cadherin (CDH1) decreased over time during differentiation. Transforming growth factor β (TGF-β) induces the process of EMT through the Smad and JNK signaling. The present data showed that the main drivers TGFb2 (207.89-fold at day 8, 636-fold at day 10) and TGFb3 expression peaked (22-fold at day 8, 77.3-fold at day 10) at day 10, whereas ZEB2 (130.29-fold) and Smad3 (7.57-fold) expression peaked at day 14. NFκB was upregulated at day 10, which promote protein stabilization of snail 1 to prevent its phosphorylation by GSK3 and subsequent degradatio. The upregulation of EMT main driver genes down-regulated epithelial genes while up-regulated the mesenchymal genes. In contrast, FOXC2, the downstream of Twist and Snail was up-regulated at day 8 and 10, which induces mesenchymal properties. Fibronectin is cell-secreted glycoproteins that modulate cell attachment, spreading, migration, morphology, differentiation and oncogenic transformation. Fibronectin is activated during EMT as a hallmark of mesenchymal cells. The present data showed that fibronectin was highly up-regulated from day 8 to day 14. Vimentin peaked at day 14. Although Eomes was down-regulated from day 2, it was still expressed at some level at day 8 and day 10. This was consistent with that Eomes is important for gastrulation and EMT. LAMB1 expression peaked at day 14 whereas LEF1 expression peaked at day 8 (787-fold) and remained highly expressed at day 10 and 14. Interestingly, the present data showed that similar to CDH1, DACT2 expression decreased over time during differentiation. Similar to CDH2, CDH10 expressed from day 8 to 10 and peaked at day 10 (FIG. 13D). These data suggests CDH10 and DACT2 are good markers for EMT. MEIS1 and JUN was up-regulated from day 8, suggesting that MEIS1 and JUN also play a role during MSC development.

Pro-inflammatory gene such as IL6, JAK1, STAT1, STAT2, STATSA STAT6, VEGFB and IFNAR1 were also increased in iPSC-MSC and BMSCs (FIG. 13E), suggesting that the expression of these genes may play a role in MSCs.

Example 8—Epigenetic Dynamics During Differentiation Toward MSCs

Figure 14:
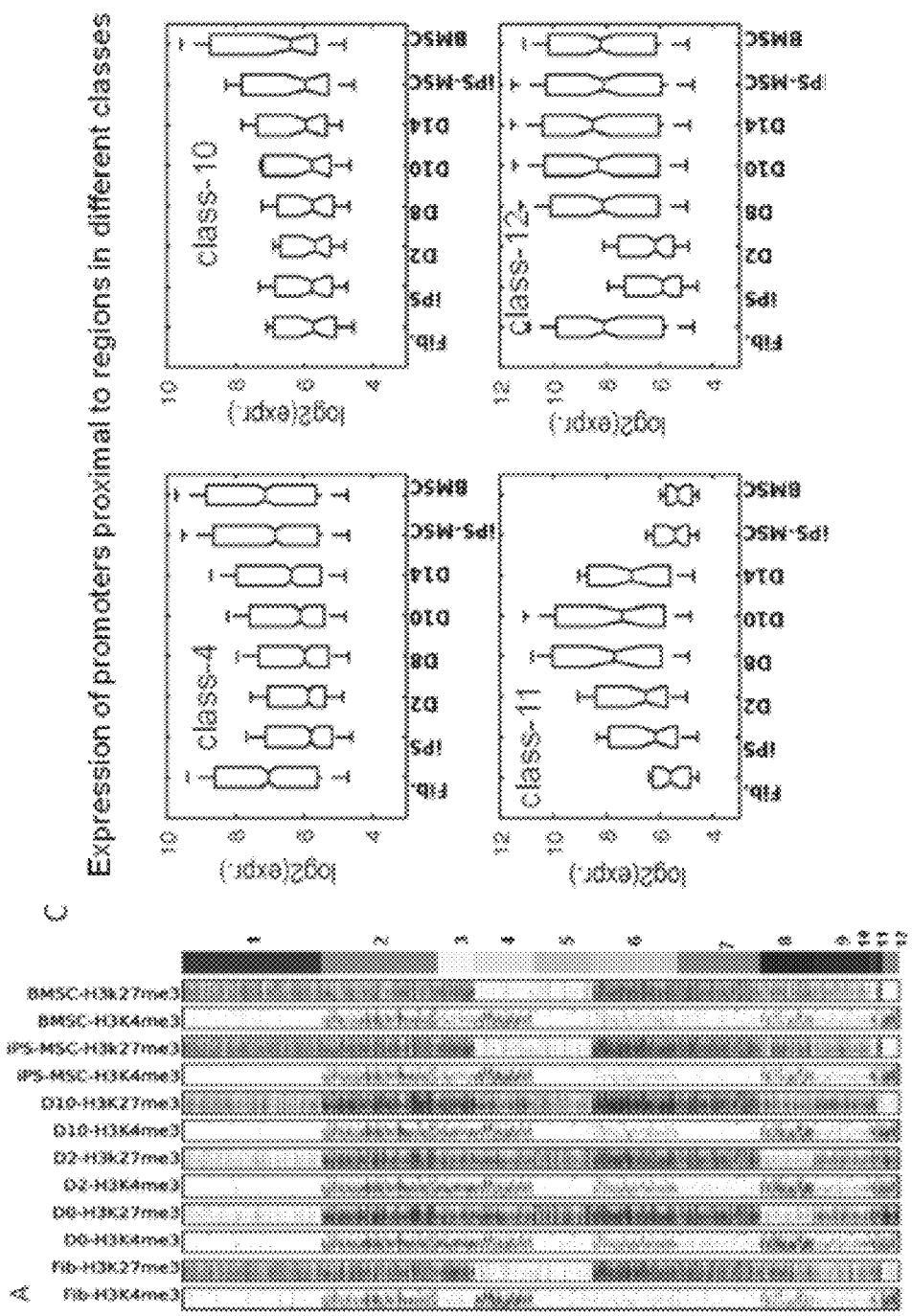
FIG. 14 shows the epigenetic dynamics during differentiation of iPSCs towards MSC.
Figure 14:
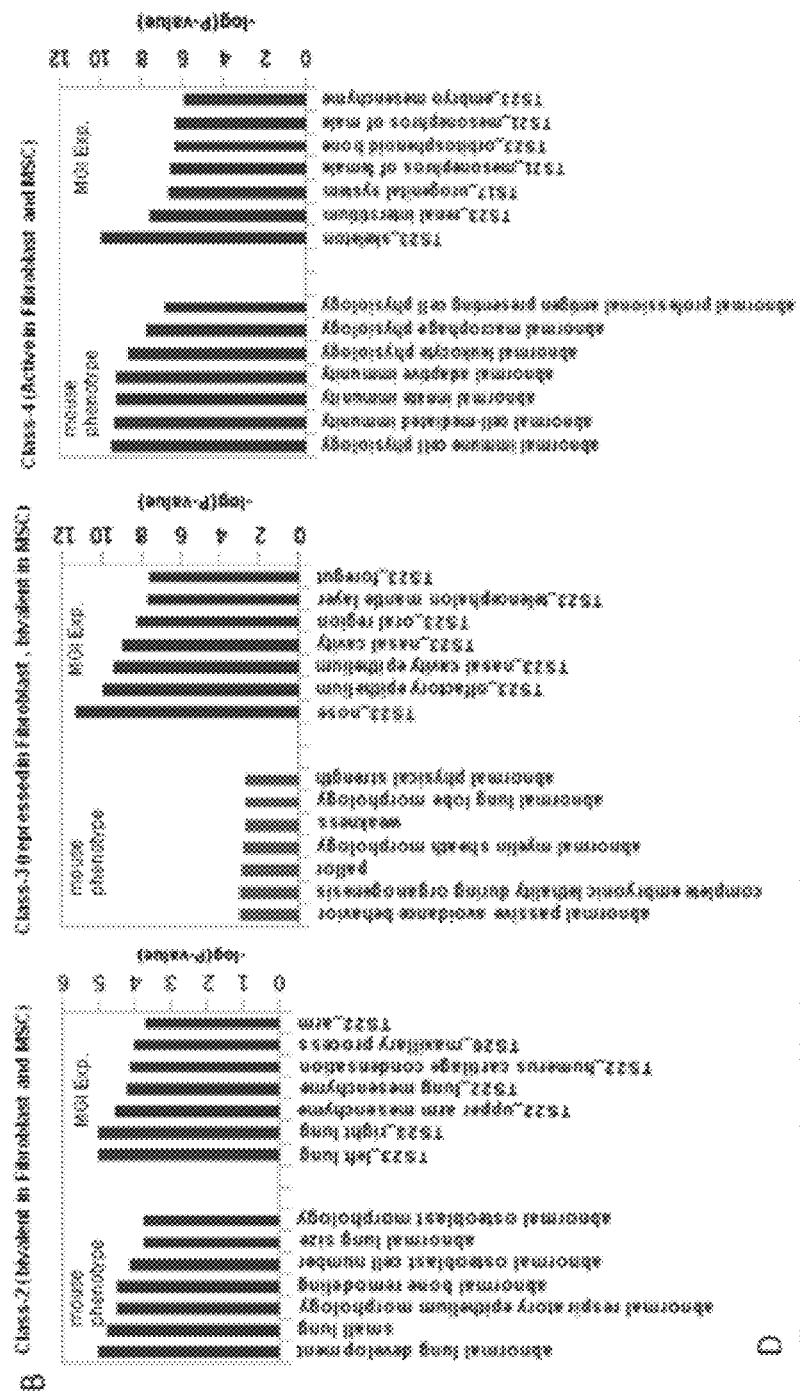

In order to decipher the molecular events of MSC development, ChIP-seq analysis was performed against H3K4me3 and H3K27me3 at 5 different stages and BMSC. This provides an overview of active and repressed promoters, which also corroborated with expression data. Enrichment of functional annotation of their proximal genes was done with GREAT for mouse phenotype and MGI expression as gene-perturbations have been studied more thoroughly in mouse. 12 classes of regions were obtained (FIG. 14A). Region belonging to class-2 were bivalent in both fibroblast and remained bivalent during differentiation and in MSC. Class-3 regions are repressed in fibroblast and bivalent in BMSC and iPSC-MSC. These regions could provide an explanation of higher multi-potency of MSC than fibroblast. Genes proximal to class-3 regions have expression in developing early brain and foregut and olfactory epithelium (FIG. 14B). There have been reports of similarity between BMSC and MSC in olfactory epithelium and potential of BMSC to differentiate towards few neuronal and foregut lineages Regions in class 4 are proximal to promoters which are active in MSC and fibroblast. The enriched mouse phenotype terms for class-4 shows the immunoregulatory property of MSC. Whereas the MGI expression is clearly in mesodermal lineage organ known to have MSCs. Most interesting trend came in class 10 regions which seem to be active in BMSC and bivalent or repressed in fibroblast. The mouse phenotype terms for class-10 regions clearly indicate that knockdown of their proximal genes tend to increas differentiation of MSC towards adipocytes and osteoblast. Those genes could be responsible for the maintenance of MSC and blocking their differentiation. Some of these genes specific to BMSC could also be expressed in nervous system as shown by MGI expression terms. Regions in class-11 are active specifically during EMT stage (D8 and D10) and had more terms enriched for cardiovascular system. These genes are repressed at MSC stage as they could be leading to differentiation of MSC towards the lineages shown in MGI expression term. Regions in class −12 active in fibroblast, EMT stage and MSC tend to be around genes expressed during early embryonic development and remain active during development mesodermal organs (FIG. 14C).

Different classes of bivalent and active regions during MSC formation also showed an interesting pattern in enrichment of TF motifs. Stat5a and Stat6 motif enrichment for class-2 clearly indicate and support the finding that they could be involved in activating and poising of genes in MSCs to differentiate towards different lineages. IRF motif was enriched in regions active in MSC and fibroblast (class-4) whereas NFκb motif was on top for class-10 sites which were specifically more active in MSC (FIG. 14D).

Example 9—Tumorigenicity Assay

Immunodeficient nude mice were maintained in pathogen-free conditions. iPSC-MSCs were harvested by trypsinization and washed twice with PBS, and viable cell number was determined by trypan blue exclusion. 2×10$^6$ iPSC-MSCs suspended in matrigel were subcutaneously transplanted into the flanks of 6-week-old nude mice per site, 6 mice were performed. Mice were observed for 12 weeks to monitor teratoma. No tumors were observed at 12 weeks after transplantation, whereas teratomas containing 3 germ layers of tissues were observed in the parental iPSCs.

Example 10—Transplantation of iPSC-MSCs into Rats for Cartilage Repair and Histological Evaluation iPSC-MSCs were transplanted into rats with cartilage defects. Bone marrow-derived MSCs (BMSCs) were used as control. Briefly, male Sprague Dawley (SD) rats (500 g) were anesthetized using an intraperitoneal injection of a mixture ketamine (10 mg/100 g) and xylazine (1 mg/100 g). An anterior midline incision was made through the skin of the knee. The knee joints were opened via a medial parapatellar approach and the patella was everted. An osteochondral defect (1.5 mm in diameter and 1.5 mm in depth) was created in the patellar groove of the distal femur. Pellets from iPSC-MSCs or BMSCs were transplanted into the defective cartilage, the defective cartilage without transplanted cells were used as empty control. The pellets from 3×10$^5$ iPSC-MSCs or BMSCs were pre-induced into chondrocyte differentiation in vitro for 1 week before transplantation as described. The recipient animals received daily subcutaneous injections of Cyclosporine (14 mg/kg, Novartis Pharma AG, Basel, Switherland) immediately after surgery.

At 6 weeks and 12 weeks after surgery, rats from each group were sacrificed. The distal femurs with defects were collected, fixed in 10% buffered formation. The tissues were decalcified and cut into 5 μm section. Staining was performed with hematoxylin/eosin, Col2A1 immunostaining for major collagen of cartilage and Alcian blue stain for sulfated proteoglycan matrix of cartilage. Each sample was graded according to the histological scale as described (Wakitani et al.,1994). The scale consisted of five categories: cell morphology, matrix staining, surface regularity, thickness of cartilage, and integration of donor with host cartilage. The scores ranged from 0 (normal articular cartilage) to 14 (no cartilaginous tissue). At least 10 defects from each group were assessed.

Figure 15:
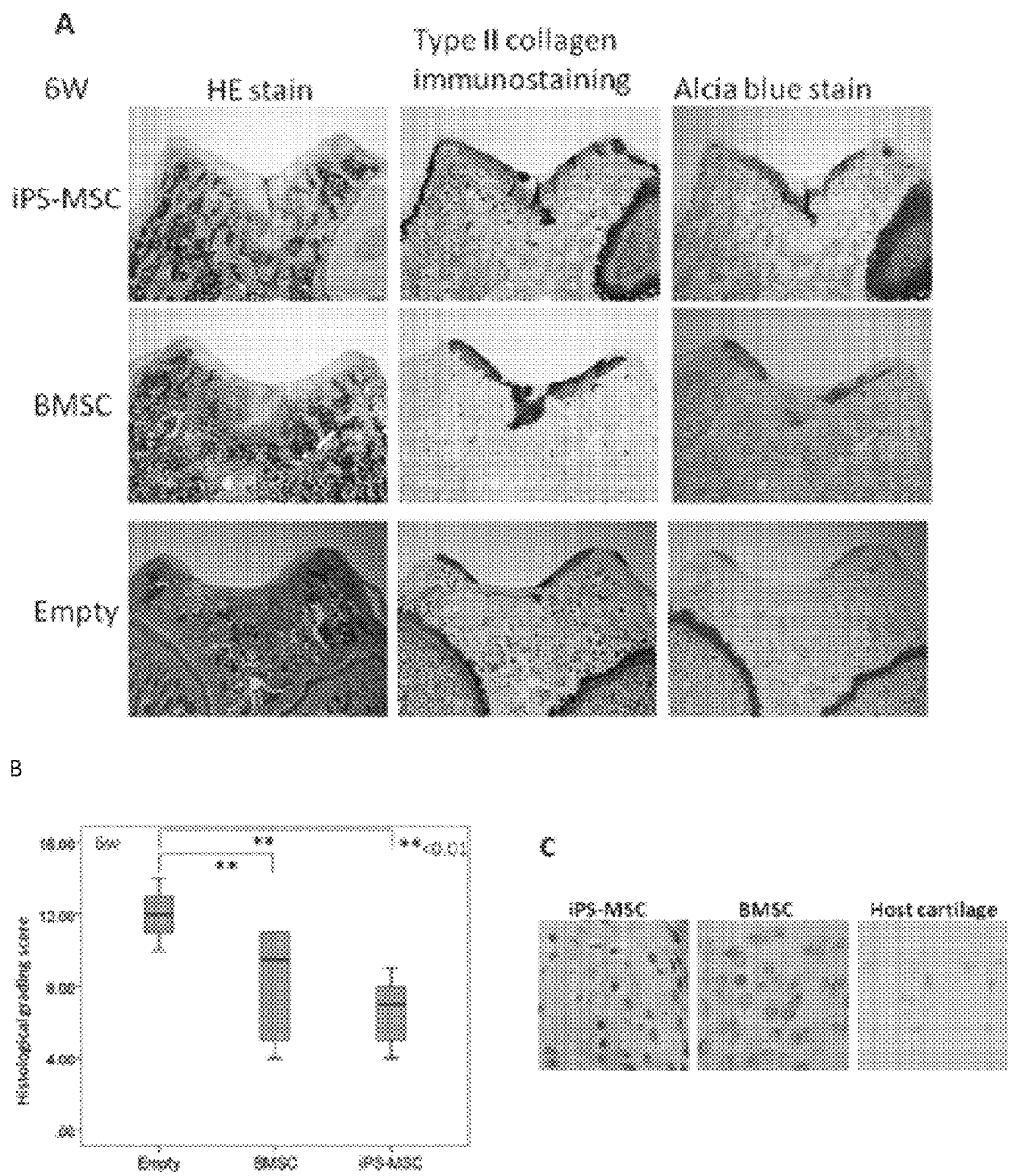
FIG. 15 shows that the mature mesenchymal stem cells obtained using the method as disclosed herein are capable of cartilage repair and regeneration.
Figure 15:
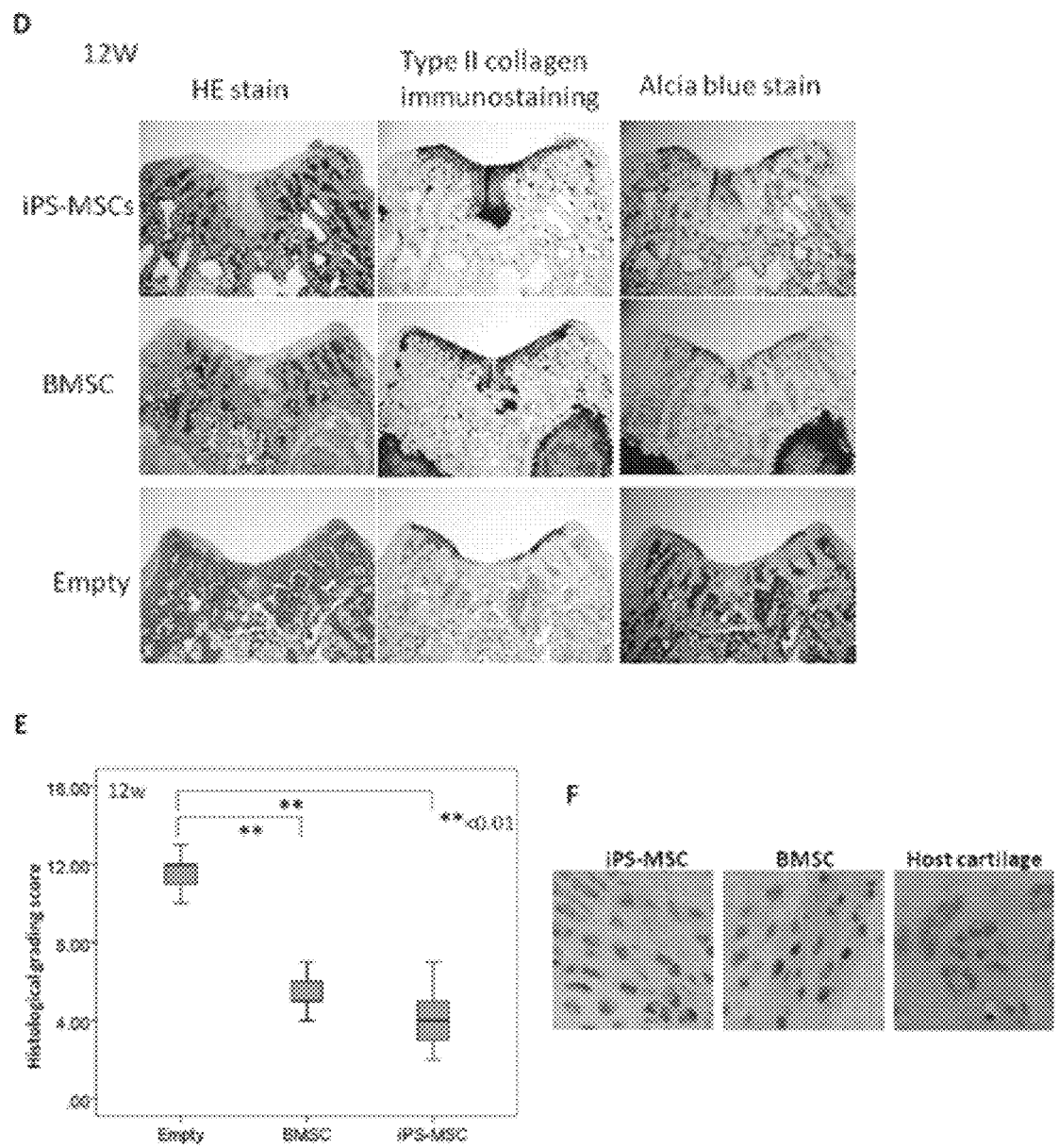

Six weeks after transplantation, the defective cartilages were filled with reparative tissue from transplanted pellets, cartilage from reparative tissues was positive for Alcian blue stain for sulfated proteoglycan matrix and collagen type II immunostaining for major collagen (FIG. 15A), showing that cartilage was formed similar to adjacent cartilage. Cartilage from iPSC-MSCs was able to integrate to the adjacent host cartilage. At higher magnification, the cells resembled well-differentiated chondrocytes and were surrounded by metachomatic matrix. However, the surface area of reparative tissues was negative for Alcian blue stain for sulfated proteoglycan matrix and collagen type II immunostaining for major collagen, suggesting that the repair of cartilage defects was not complete. In contrast, control group without transplanted MSCs were negative for Alcian blue stain for sulfated proteoglycan matrix and type II immunostaining for major collagen. Compared with iPSC-MSCs, similar reparative effects were observed in BMSC group. Histological grading score showed that there was significant difference between the control group and the iPSC-MSCs or BMSCs. There was no significant difference in histological grading score between iPSC-MSCs and BMSCs group (FIG. 15B). Immunostaining against human specific antigen Lamin A/C showed that transplanted cells integrated into neo-cartilage (FIG. 15C).

At week 12, reparative cartilage from iPSC-MSCs integrated well to both edges of the adjacent host cartilage. Most importantly, reparative tissues were mostly hyaline cartilage confirmed by positive Alcian blue stain for sulfated proteoglycan matrix and collagen type II immunostaining for major collagen, which was similar to BMSC group. In contrast, cartilage was not observed in the control group (FIG. 15D). Similar to 6 weeks, there was significant difference in histological grading score between the control group and the iPSC-MSCs or BMSCs (FIG. 15E). Immunostaining against human specific antigen Lamin A/C showed that transplanted cells integrated into neo-cartilage (FIG. 15F). Collectively, iPSC-MSCs are functional MSCs and able to fully repair cartilage defects. These data also suggest that iPSC-MSCs will provide alternative functional patient-specific source for cartilage repair and regeneration.

Example 12—Fluorescence-Activated Cell Sorting iPSC-MSCs were harvested in 0.25% trypsin/EDTA, washed with FACS buffer (PBS+0.5% BSA+5 mM EDTA), and then incubated for 30 min in dark in FACS buffer containing phycoerythrin (PE)-conjugated antibodies against the following surface antigens: CD14, CD34, CD45, CD29, CD44, CD49C, CD73, CD90, CD105, CD151 and CD166. Cells were washed and re-suspended in FACS buffer for analysis. Cells were stained with PE-conjugated nonspecific IgG to assess background fluorescence. CD73+ cells were sorted for further expansion and transplantation for cartilage repair.

Example 13—Real-Time RT-PCR

Quantitative real-time PCR was performed with Taqman expression assay using ABI PRISM 7900HT sequence Detection System (Applied Biosystems). Briefly, 0.5m of total RNA was converted to cDNA using high capacity cDNA archive kit in 30 µl and then diluted to 500 µl. Quantitative real-time PCR was done as follows: initial denaturation for 2 min at 50° C., 10 min at 95° C., following 40 cycles of PCR (95° C. for 15 s, 60° C. for 1 min) by using 5 µl of 2× Master mix, 0.5 µl of probe and 4.5 µl of cDNA. All probes were designed with a 5' fluoregenic 6-carboxylfluorescein, and a 3' quencher, tetramethyl-6-carboxyrhodamine. The expression of human GAPDH was used to normalize gene expression levels.

Example 14—Microarray Analysis

To determine the change in gene expression profile during differentiation of iPSCs toward MSCs, microarrays were performed by illumina. Total RNA was isolated using RNeasy mini-kit (Qiagen, Chatsworth, Calif.) per the manufacturer's protocol. In brief, 0.3m total RNA was used to synthesize cRNA (Illumina TotalPrep RNA amplification kit, Ambion). The data were analyzed using Software Genespring V12.5. A t test 0.05 on normalized intensity, followed by ratio change (ratio of normalized intensity ≥2 or ≤−2), to generate the gene list with significant change. It is confirmed that all details are MIAME compliant.

Example 15—ChIP-Seq

For ChIP-seq, MRCS, MRCS-iPSCs and differentiating iPSCs at different stages were formaldehyde fixed, lysed, sonicated and precleared. The chromatin was probed overnight using H3K4me3 and H3K27me3 antibodies (abcam) conjugated to Protein G Dynabeads (Invitrogen). Subsequently, chromatin was precipitated, rigorously washed and decross-linking overnight at 65° C. Ten nanograms of chromatin were used to generate libraries (TruSeq kit, Illumina) for Hi-Seq 2000 Sequencing (illumina, 72 bp single-end reads). Reads were aligned to hg19.

Example 16—Karyotyping

Karyptyping was performed using a standard technique. Briefly, dividing cells were treated with 10 µg/ml colcemid to enrich the population of metaphase cells, then harvested and treated briefly with 0.075 M KCl hypotonic solution to make the nuclei swell osmotically. The swollen cells in fixative were fixed, dropped onto a microscope slide, dried and stained.

Example 17—Statistical Analysis

Comparisons of histological scores for cartilage repair were performed using the Mann-Whitney U test for non-parametric analyses. Otherwise, statistical analyses were performed using Student's unpaired 2-tailed t-tests. P values less than 0.05 were considered statistically significant.

What is claimed is:

1. A method of generating mature mesenchymal stem cells from lateral plate mesoderm cells, comprising culturing the lateral plate mesoderm cells on an extracellular matrix in a mesenchymal stem cell culture medium comprising:
   fibroblast growth factor;
   platelet-derived growth factor (PDGF);
   epidermal growth factor (EGF) family protein; and
   ascorbic acid,
   wherein the method further comprises, before culturing the lateral plate mesoderm cells:
   culturing primitive streak mesendoderm cells on an extracellular matrix to obtain lateral plate mesoderm cells, wherein culturing the primitive streak mesendoderm further comprises:
   (i) culturing the primitive streak mesendoderm on an extracellular matrix in a first lateral plate mesoderm cell culture medium; and
   (ii) subsequently culturing the primitive streak mesendoderm from (i) on an extracellular matrix in a second lateral plate mesoderm cell culture medium,
   wherein the first lateral plate mesoderm cell culture medium comprises:
   fibroblast growth factor;
   bone morphogenetic protein;
   Rho-associated protein kinase (ROCK) inhibitor; and
   follistatin,
   and wherein the second lateral plate mesoderm cell culture medium comprises:
   fibroblast growth factor;
   bone morphogenetic protein; and
   follistatin.

2. The method of claim 1, wherein the primitive streak mesendoderm cells to be cultured in the first lateral plate mesoderm cell culture medium are characterized by any one or more or all of the following markers: MIXL1, T, GSC and Wnt3.

3. The method of claim 1, wherein the fibroblast growth factor is FGF2.

4. The method of claim 1, wherein the bone morphogenetic protein is BMP4.

5. The method of claim 1, wherein the ROCK inhibitor is Y27632 (R)-(+)-trans-4-(1-Aminoethyl)-N-(4-Pyridyl)cyclohexanecarboxamide dihydrochloride.

6. A method of generating mature mesenchymal stem cells from lateral plate mesoderm cells, comprising culturing the lateral plate mesoderm cells on an extracellular matrix in a mesenchymal stem cell culture medium comprising:
   fibroblast growth factor;
   platelet-derived growth factor (PDGF);
   epidermal growth factor (EGF) family protein; and
   ascorbic acid, wherein the method further comprises, before culturing the lateral plate mesoderm cells: culturing primitive streak mesendoderm cells on an extracellular matrix to obtain lateral plate mesoderm cells; and before culturing the primitive streak mesendoderm cells: culturing pluripotent stem cells on an extracellular matrix to obtain primitive streak mesendoderm cells, wherein culturing the pluripotent stem cells on an extracellular matrix further comprises:

(i) culturing the pluripotent stem cells on an extracellular matrix in a first primitive streak mesendoderm cell culture medium; and (ii) subsequently culturing the pluripotent stem cells from (i) on an extracellular matrix in a second primitive streak mesendoderm cell culture medium, wherein the first primitive streak mesendoderm cell culture medium comprises:

activin; and

WNT-signaling activator;

and wherein the second primitive streak mesendoderm cell culture medium comprises:

activin;

WNT-signaling activator; and fibroblast growth factor.

7. The method of claim 6, wherein the activin is Activin A.

8. The method of claim 6, wherein the WNT-signaling activator is CHIR-99021 6-[2-[[4-(2,4-dichlorophenyl)-5-(5-methyl-1H-imidazol-2-yl)pyrimidin-2-yl]amino]ethyl-amino]pyridine-3-carbonitrile.

9. The method of claim 6, wherein the fibroblast growth factor is FGF2.

* * * * *